(12) United States Patent
Henn et al.

(10) Patent No.: US 11,464,812 B2
(45) Date of Patent: Oct. 11, 2022

(54) SYNERGISTIC BACTERIAL COMPOSITIONS AND METHODS OF PRODUCTION AND USE THEREOF

(71) Applicant: Seres Therapeutics, Inc., Cambridge, MA (US)

(72) Inventors: Matthew R. Henn, Somerville, MA (US); Geoffrey von Maltzahn, Boston, MA (US); Anthony Mario D'Onofrio, Northborough, MA (US); Kevin Daniel Litcofsky, Boston, MA (US); David Arthur Berry, Brookline, MA (US); David N. Cook, Brookline, MA (US); Noubar B. Afeyan, Lexington, MA (US); John Grant Aunins, Doylestown, PA (US)

(73) Assignee: Seres Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/120,671

(22) Filed: Dec. 14, 2020

(65) Prior Publication Data

US 2021/0169949 A1 Jun. 10, 2021

Related U.S. Application Data

(60) Division of application No. 16/223,008, filed on Dec. 17, 2018, now Pat. No. 10,864,235, which is a continuation of application No. 15/359,439, filed on Nov. 22, 2016, now abandoned, which is a continuation of application No. 14/592,481, filed on Jan. 8, 2015, now Pat. No. 9,533,014, which is a continuation of application No. 14/221,190, filed on Mar. 20, 2014, now Pat. No. 9,028,841, which is a division of application No. 14/091,201, filed on Nov. 26, 2013, now Pat. No. 8,906,668, which is a continuation of application No. PCT/US2013/071758, filed on Nov. 25, 2013.

(60) Provisional application No. 61/729,515, filed on Nov. 23, 2012, provisional application No. 61/729,517, filed on Nov. 23, 2012, provisional application No. 61/729,518, filed on Nov. 23, 2012, provisional application No. 61/729,519, filed on Nov. 23, 2012, provisional application No. 61/729,520, filed on Nov. 23, 2012, provisional application No. 61/729,521, filed on Nov. 23, 2012, provisional application No. 61/729,522, filed on Nov. 23, 2012, provisional application No. 61/729,524, filed on Nov. 23, 2012, provisional application No. 61/729,525, filed on Nov. 23, 2012, provisional application No. 61/729,526, filed on Nov. 23, 2012, provisional application No. 61/729,527, filed on Nov. 23, 2012.

(51) Int. Cl.

| | |
|---|---|
| *A61K 39/02* | (2006.01) |
| *A61K 35/742* | (2015.01) |
| *A61K 35/74* | (2015.01) |
| *A23L 33/10* | (2016.01) |
| *A23L 33/135* | (2016.01) |
| *A61K 38/13* | (2006.01) |
| *A23P 10/30* | (2016.01) |
| *A61K 9/00* | (2006.01) |
| *A61K 9/48* | (2006.01) |
| *A61K 45/06* | (2006.01) |

(52) U.S. Cl.
CPC .......... *A61K 35/742* (2013.01); *A23L 33/127* (2016.08); *A23L 33/135* (2016.08); *A23P 10/30* (2016.08); *A61K 9/0053* (2013.01); *A61K 9/4891* (2013.01); *A61K 35/74* (2013.01); *A61K 38/13* (2013.01); *A61K 45/06* (2013.01); *A23V 2002/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 3,009,861 A | 11/1961 | Gordon et al. | |
| 3,009,864 A | 11/1961 | Webb | |
| 3,228,838 A | 1/1966 | Rinfret et al. | |
| 3,608,030 A | 9/1971 | Tint | |
| 4,077,227 A | 3/1978 | Larson | |
| 4,205,132 A | 5/1980 | Sandine et al. | |
| 4,655,047 A | 4/1987 | Temple et al. | |
| 4,689,226 A | 8/1987 | Nurmi et al. | |
| 4,839,281 A | 6/1989 | Gorbach et al. | |
| 5,196,205 A | 3/1993 | Borody | |
| 5,425,951 A | 6/1995 | Goodrich, Jr. et al. | |
| 5,436,002 A | 7/1995 | Payne et al. | |
| 5,443,826 A | 8/1995 | Borody | |
| 5,599,795 A | 2/1997 | McCann et al. | |

(Continued)

FOREIGN PATENT DOCUMENTS

| | | |
|---|---|---|
| CN | 102131928 A | 7/2011 |
| CN | 102940652 A | 2/2013 |

(Continued)

OTHER PUBLICATIONS

14th International Congress of Immunology, Kobe, Japan, International Immunology, Aug. 2010, 3 pages, vol. 22, Issue Suppl 1 Pt 3.

(Continued)

*Primary Examiner* — Jennifer E Graser
(74) *Attorney, Agent, or Firm* — Sterne, Kessler, Goldstein & Fox P.L.L.C.

(57) ABSTRACT

Provided are therapeutic compositions containing Ecobiotic™ populations for prevention, treatment and reduction of symptoms associated with a dysbiosis of a mammalian subject such as a human.

20 Claims, 1 Drawing Sheet

Specification includes a Sequence Listing.

(56) References Cited

U.S. PATENT DOCUMENTS

| | | |
|---|---|---|
| 5,648,206 A | 7/1997 | Goodrich, Jr. et al. |
| 5,951,977 A | 9/1999 | Nisbet et al. |
| 5,965,128 A | 10/1999 | Doyle et al. |
| 6,589,771 B1 | 7/2003 | Marshall |
| 6,645,530 B1 | 11/2003 | Borody |
| 7,326,551 B2 | 2/2008 | Maupin-Furlow et al. |
| 7,427,398 B2 | 9/2008 | Baillon et al. |
| 7,628,982 B2 | 12/2009 | Klaviniskis et al. |
| 7,632,520 B2 | 12/2009 | Khandelwal |
| 7,708,988 B2 | 5/2010 | Farmer |
| 7,731,976 B2 | 6/2010 | Cobb et al. |
| 7,763,420 B2 | 7/2010 | Stritzker et al. |
| 7,981,411 B2 | 7/2011 | Nadeau et al. |
| 7,998,473 B2 | 8/2011 | Boileau et al. |
| 8,021,654 B2 | 9/2011 | Rehberger et al. |
| 8,034,601 B2 | 10/2011 | Boileau et al. |
| 8,039,006 B2 | 10/2011 | Prato |
| 8,147,482 B2 | 4/2012 | Shimizu et al. |
| 8,187,590 B2 | 5/2012 | Farmer |
| 8,236,508 B2 | 8/2012 | Mutharasan et al. |
| 8,388,996 B2 | 3/2013 | Gehling et al. |
| 8,460,648 B2 | 6/2013 | Borody |
| 8,906,668 B2 | 12/2014 | Henn et al. |
| 8,968,721 B2 | 3/2015 | Harel |
| 9,011,834 B1 | 4/2015 | McKenzie et al. |
| 9,028,841 B2 | 5/2015 | Henn et al. |
| 9,180,147 B2 | 11/2015 | McKenzie et al. |
| 9,408,872 B2 | 8/2016 | Borody |
| 9,446,080 B2 | 9/2016 | McKenzie et al. |
| 9,533,014 B2 | 1/2017 | Henn et al. |
| 9,585,921 B2 | 3/2017 | McKenzie et al. |
| 9,610,307 B2 | 4/2017 | Berry et al. |
| 9,808,519 B2 | 11/2017 | Honda et al. |
| 9,855,303 B2 | 1/2018 | McKenzie et al. |
| 9,956,282 B2 | 5/2018 | Cook et al. |
| 10,064,900 B2 | 9/2018 | Von Maltzahn et al. |
| 10,064,901 B2 | 9/2018 | McKenzie et al. |
| 10,076,546 B2 | 9/2018 | Henn et al. |
| 10,238,694 B2 | 3/2019 | Honda et al. |
| 10,258,655 B2 | 4/2019 | Henn et al. |
| 10,864,235 B2 | 12/2020 | Henn et al. |
| 10,881,696 B2 | 1/2021 | Henn et al. |
| 10,967,011 B2 | 4/2021 | McKenzie et al. |
| 10,973,861 B2 | 4/2021 | Afeyan et al. |
| 11,185,562 B2 | 11/2021 | Cook et al. |
| 11,266,699 B2 | 3/2022 | Henn et al. |
| 2001/0036453 A1 | 11/2001 | Reid et al. |
| 2004/0028689 A1 | 2/2004 | Borody |
| 2004/0170617 A1 | 9/2004 | Finegold |
| 2005/0048515 A1 | 3/2005 | Garner |
| 2005/0180962 A1 | 8/2005 | Raz et al. |
| 2006/0046246 A1 | 3/2006 | Zeng et al. |
| 2006/0067924 A1 | 3/2006 | Lee et al. |
| 2006/0188523 A1 | 8/2006 | Pei et al. |
| 2006/0233830 A1 | 10/2006 | Wong et al. |
| 2007/0141139 A1 | 6/2007 | Vandenberg |
| 2008/0213752 A1 | 9/2008 | Stave et al. |
| 2009/0197249 A1 | 8/2009 | Gillevet |
| 2010/0074872 A1 | 3/2010 | Blaser et al. |
| 2010/0215745 A1 | 8/2010 | Lazzari et al. |
| 2011/0081320 A1 | 4/2011 | Westall et al. |
| 2011/0113863 A1 | 5/2011 | Fuhrmann et al. |
| 2011/0189132 A1 | 8/2011 | Garner et al. |
| 2011/0280840 A1 | 11/2011 | Blaser et al. |
| 2011/0280847 A1 | 11/2011 | Sorg et al. |
| 2012/0020950 A1 | 1/2012 | Davis et al. |
| 2012/0021429 A1 | 1/2012 | Rublee et al. |
| 2012/0021921 A1 | 1/2012 | Scott et al. |
| 2012/0058094 A1 | 3/2012 | Blaser et al. |
| 2012/0064592 A1 | 3/2012 | O'Mullan et al. |
| 2012/0128633 A1 | 5/2012 | Veiga et al. |
| 2012/0128634 A1 | 5/2012 | Veiga et al. |
| 2012/0148629 A1 | 6/2012 | Holvoet et al. |
| 2012/0149584 A1 | 6/2012 | Olle et al. |
| 2012/0165215 A1 | 6/2012 | Andersen et al. |
| 2012/0177650 A1 | 7/2012 | Borody |
| 2012/0207726 A1 | 8/2012 | Lipkin et al. |
| 2012/0238468 A1 | 9/2012 | Tuk et al. |
| 2012/0264637 A1 | 10/2012 | Wiener-Kronish et al. |
| 2012/0276149 A1 | 11/2012 | Littman et al. |
| 2012/0276201 A1 | 11/2012 | Trachtman |
| 2012/0315249 A1 | 12/2012 | Olmstead |
| 2013/0017999 A1 | 1/2013 | Fremont et al. |
| 2013/0022575 A1 | 1/2013 | Cassity |
| 2013/0045274 A1 | 2/2013 | Hlavka |
| 2013/0045874 A1 | 2/2013 | Ehrlich |
| 2013/0065862 A1 | 3/2013 | Johnson |
| 2013/0115232 A1 | 5/2013 | Ferrara et al. |
| 2013/0121968 A1 | 5/2013 | Quay |
| 2013/0149339 A1 | 6/2013 | Honda et al. |
| 2013/0149375 A1 | 6/2013 | Geall |
| 2013/0195820 A1 | 8/2013 | Wacklin et al. |
| 2013/0266539 A1 | 10/2013 | Borody |
| 2014/0045744 A1 | 2/2014 | Gordon et al. |
| 2014/0135398 A1 | 5/2014 | Matar et al. |
| 2014/0147417 A1 | 5/2014 | Sadowsky et al. |
| 2014/0147425 A1 | 5/2014 | Henn et al. |
| 2014/0199281 A1 | 7/2014 | Henn et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2015/0011415 A1 | 1/2015 | Levin et al. |
| 2015/0093360 A1 | 4/2015 | McKenzie et al. |
| 2015/0190435 A1 | 7/2015 | Henn et al. |
| 2016/0271188 A1 | 9/2016 | Berry et al. |
| 2017/0165302 A1 | 6/2017 | Henn et al. |
| 2021/0169946 A1 | 6/2021 | Henn et al. |
| 2021/0169948 A1 | 6/2021 | Henn et al. |
| 2021/0169949 A1 | 6/2021 | Henn et al. |
| 2021/0252079 A1 | 8/2021 | Matthew et al. |

FOREIGN PATENT DOCUMENTS

| | | |
|---|---|---|
| DE | 102006062250 A1 | 6/2008 |
| EA | 006847 B1 | 4/2006 |
| EP | 0033584 A3 | 4/1982 |
| EP | 0446069 A1 | 9/1991 |
| EP | 0456418 A2 | 11/1991 |
| EP | 0433299 A4 | 4/1992 |
| EP | 0479820 B1 | 9/1994 |
| EP | 1107772 B1 | 4/2006 |
| EP | 1631312 B1 | 9/2008 |
| EP | 2337569 A2 | 6/2011 |
| EP | 2338989 A1 | 6/2011 |
| EP | 2519108 A1 | 11/2012 |
| EP | 2626076 A1 | 8/2013 |
| EP | 2684469 A1 | 1/2014 |
| EP | 2750682 B1 | 5/2016 |
| JP | H0656679 A | 3/1994 |
| JP | 2007332083 A | 12/2007 |
| JP | 2010539179 A | 12/2010 |
| JP | 5019563 B2 | 9/2012 |
| RU | 2035186 C1 | 5/1995 |
| RU | 2439145 C2 | 1/2012 |
| WO | WO-9001335 A1 | 2/1990 |
| WO | WO-9408598 A1 | 4/1994 |
| WO | WO-9708598 A1 | 3/1997 |
| WO | WO-9709886 A1 | 3/1997 |
| WO | WO-9826787 A1 | 6/1998 |
| WO | WO-0010582 A2 | 3/2000 |
| WO | WO-0193904 A1 | 12/2001 |
| WO | WO-0207741 A1 | 1/2002 |
| WO | WO-0243649 A2 | 6/2002 |
| WO | WO-2005017095 A2 | 2/2005 |
| WO | WO-2005110445 A2 | 11/2005 |
| WO | WO-2006012586 A2 | 2/2006 |
| WO | WO-2007036230 A1 | 4/2007 |
| WO | WO-2007136553 A2 | 11/2007 |
| WO | WO-2008076696 A2 | 6/2008 |
| WO | WO-2008077614 A2 | 7/2008 |
| WO | WO-2008083157 A2 | 7/2008 |
| WO | WO-2010030997 A1 | 3/2010 |
| WO | WO-2010062369 A2 | 6/2010 |

(56) References Cited

FOREIGN PATENT DOCUMENTS

| | | |
|---|---|---|
| WO | WO-2010124387 A1 | 11/2010 |
| WO | WO-2010151842 A2 | 12/2010 |
| WO | WO-2011005756 A1 | 1/2011 |
| WO | WO-2011022542 A1 | 2/2011 |
| WO | WO-2011022660 A1 | 2/2011 |
| WO | WO-2011033310 A1 | 3/2011 |
| WO | WO-2011043654 A1 | 4/2011 |
| WO | WO-2011046616 A2 | 4/2011 |
| WO | WO-2011060123 A1 | 5/2011 |
| WO | WO-2011094027 A1 | 8/2011 |
| WO | WO-2011103123 A2 | 8/2011 |
| WO | WO-2011107481 A2 | 9/2011 |
| WO | WO-2011107482 A2 | 9/2011 |
| WO | WO-2011113801 A1 | 9/2011 |
| WO | WO-2011152566 A2 | 12/2011 |
| WO | WO-2012009712 A2 | 1/2012 |
| WO | WO-2012016287 A2 | 2/2012 |
| WO | WO-2012033814 A2 | 3/2012 |
| WO | WO-2012045150 A1 | 4/2012 |
| WO | WO-2012064981 A2 | 5/2012 |
| WO | WO-2012108830 A1 | 8/2012 |
| WO | WO-2012116289 A1 | 8/2012 |
| WO | WO-2012122478 A1 | 9/2012 |
| WO | WO-2012122522 A2 | 9/2012 |
| WO | WO-2012142605 A1 | 10/2012 |
| WO | WO-2012148991 A1 | 11/2012 |
| WO | WO-2012159023 A2 | 11/2012 |
| WO | WO-2013016636 A1 | 1/2013 |
| WO | WO-2013019896 A1 | 2/2013 |
| WO | WO-2013032328 A1 | 3/2013 |
| WO | WO-2013037067 A1 | 3/2013 |
| WO | WO-2013037068 A1 | 3/2013 |
| WO | WO-2013050792 A1 | 4/2013 |
| WO | WO-2013053836 A1 | 4/2013 |
| WO | WO-2013080561 A1 | 6/2013 |
| WO | WO-2013166031 A1 | 11/2013 |
| WO | WO-2013171515 A1 | 11/2013 |
| WO | WO-2013176774 A1 | 11/2013 |
| WO | WO-2013177596 A2 | 11/2013 |
| WO | WO-2014082050 A1 | 5/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014145958 A2 | 9/2014 |
| WO | WO-2014153194 A2 | 9/2014 |
| WO | WO-2014177667 A1 | 11/2014 |
| WO | WO-2015018307 A1 | 2/2015 |
| WO | WO-2015077794 A1 | 5/2015 |
| WO | WO-2015095241 A2 | 6/2015 |
| WO | WO-2017091783 A2 | 6/2017 |
| WO | WO-2017102816 A1 | 6/2017 |
| WO | WO-2017160711 A1 | 9/2017 |
| WO | WO-2019089643 A1 | 5/2019 |

OTHER PUBLICATIONS

Aas, J., et al., "Recurrent Clostridium difficile Colitis: Case Series Involving 18 Patients Treated with Donor Stool Administered via a Nasogastric Tube," Clinical Infectious Diseases 36(5):580-585, Oxford University Press, United States (Mar. 2003).

Abrams, R.S., "Open-label, Uncontrolled Trial of Bowel Sterilization and Repopulation With Normal Bowel Flora for Treatment of Inflammatory Bowel Disease," Current Therapeutic Research 58(12):1001-1012, (Dec. 1997).

Abt, M.C., et al., "Commensal Bacteria Calibrate the Activation Threshold of Innate Antiviral Immunity," Immunity, 37(1):158-170, Cell Press, United States, (Jul. 2012 ).

Abubucker, S.,et al., "Metabolic Reconstruction for Metagenomic Data and Its Application to the Human Microbiome.," Plos Computational Biology, 8(6):1002358, Public Library of Science,United States, (2012).

Accoceberry, I., et al., "One-step Purification of Enterocytozoon Bieneusi Spores From Human Stools by Immunoaffinity Expanded-bed Adsorption," Journal of Clinical Microbiology, 39(5):1947-1951, American Society for Microbiology, United States (May 2001).

Achtman, M., and Wagner, M, "Microbial Diversity and the Genetic Nature of Microbial Species," Nature Reviews. Microbiology, 6(6):431-440, Nature Publication Group, United Kingdom (Jun. 2008).

Ahern et al., "The interleukin-23 axis m intestinal inflammation," Immunological Reviews 226:147-159 (2008).

Ahmad, T., et al., "Biomarkers of Myocardial Stress and Fibrosis as Predictors of Mode of Death in Patients With Chronic Heart Failure.," Jacc. Heart Failure, 2(3):260-268, Elsevier,United States, (Jun. 2014).

Allen-Vercoe, E., et al., "A Canadian Working Group Report on Fecal Microbial Therapy: Microbial Ecosystems Therapeutics," Canadian Journal of Gastroenterology, 26(7):457-462, Pulsus Group, Canada (Jul. 2012).

Allen-Vercoe, E., Strauss, J., and Chadee, K. (2011). Fusobacterium nucleatum: an emerging gut pathogen? Gut Microbes 2(5), 294-298.

Anderson, K.F., et al., "Evaluation of Methods to Identify the Klebsiella Pneumoniae Carbapenemase in Enterobacteriaceae," Journal of Clinical Microbiology, 45(8):2723-2725, American Society for Microbiology, United States (Aug. 2007).

Andoh, A., et al., "Terminal Restriction Fragment Polymorphism Analyses of Fecal Microbiota in Five Siblings Including Two with Ulcerative Colitis," Gastroenterology 2(5):343-345, Springer Japan (Oct. 2009).

Anonymous, "Ecobiotic Drugs," Seres Therapeutics, Oct. 22, 2015,http://web.archive.org/web/20151 022091731 /http://web.archive.org/web/20151ecobiotic-drugs, retrieved Mar. 7, 2017 (3 pages).

Anonymous, "Microbiome Therapeutics Platform," Seres Therapeutics, Retrieved on [Oct. 23, 2015], Retrieved from (http:/ /web.arch ive.org/web/20 151023063153/), Retrieved from (http://www.serestherapeutics.com/ou rscience/ microbiome-therapeutics-platform), Retrieved on [Mar. 7, 2017], 3 pages.

Anonymous, "Product Pipeline," Seres Therapeutics, Oct. 22, 2015], Retrieved from (<http:web.="" arch="" ive.org="" web="" 20="" 151="" 022091722=" http:=" <a= href=>www.serestherapeutics.com/pipeline/products)</http:>, Retrieved on [Mar. 7, 2017], (3 pages).

Application as Filed WO 2011/152566, Filed Jun. 3, 2011, 151 pages.

Arpaia, N., et al., "Metabolites Produced by Commensal Bacteria Promote Peripheral Regulatory T-cell Generation," Nature 504(7480):451-455, Nature Publishing Group, United Kingdom (Dec. 2013).

Arumugam, M., et al., "Enterotypes of the Human Gut Microbiome," Nature, 473(7346):174-180, Macmillan Journals Limited, United Kingdom (May 2011).

ASBMT RFI 2016—Disease Classifications Corresponding to CIBMIR Classifications. 2016.

Atarashi, K., et al., "Induction of Colonic Regulatory T Cells by Indigenous Clostridium Species," Science 331(6015):337-341, American Association for the Advancement of Science, United States (Jan. 2011) including supplemental data.

Atarashi, K., et al., "Treg Induction by a Rationally Selected Mixture of Clostridia Strains From the Human Microbiota," Nature 500(7461):232-236, Nature Publishing Group, United Kingdom (Aug. 2013) including supplemental data.

Australian First Examination Report, Australian Application No. 2013347805, dated Apr. 13, 2017, 3 pages.

Australian First Examination Report, Australian Application No. 2014212004, dated Sep. 21, 2017, 6 pages.

Australian First Examination Report, Australian Application No. 2014232370, dated Oct. 19, 2017, 4 pages.

Autoimmune Disease List, There Are More Than 100 Autoimmune Diseases, American Autoimmune Related Diseases Association, AARDA, Inc., 2014, 4 pages.

Babel, N.et al., "Analysis ofT Cell Receptor Repertoire by Newly Established CDR3 High-Throughput Sequencing Allows for Monitoring/ Tracing of Antigen-Specific T Cells in Peripheral Blood and Tis-

(56) References Cited

OTHER PUBLICATIONS sue," pp. 063-40, 14th ICI Abstract Book, 14th International Congress of Immunology, 2010, 3 pages.
Bacigalupo, A., et al., "Defining the Intensity of Conditioning Regimens: Working Definitions.," Biology of Blood and Marrow Transplantation : Journal of the American Society for Blood and Marrow Transplantation, 15(12):1628-1633, Carden Jennings Publishing, United States, (Dec. 2009).
Backhed, F., et al., "The Gut Microbiota as an Environmental Factor That Regulates Fat Storage," Proceedings of the National Academy of Sciences of the United States of America, 101(44):15718-15723, National Academy of Sciences, United States (Nov. 2004).
Bader, J., Albin, A., and Stahl, U. (2012). Spore-forming bacteria and their utilisation as probiotics. Benef Microbes 3(1), 67-75.
Bajaj, J.S.,et al., "Colonic Mucosal Microbiome Differs From Stool Microbiome in Cirrhosis and Hepatic Encephalopathy and is Linked to Cognition and Inflammation.," American Journal of Physiology. Gastrointestinal and Liver Physiology, 303(6):75-85, American Physiological Society, United States, (Sep. 2012).
Bakken, J.S., et al., "Treating Clostridium Difficile Infection With Fecal Microbiota Transplantation," Clinical Gastroenterology and Hepatology 9(12):1044-1049, Saunders for the American Gastroenterological Association, United States (Dec. 2011).
Bakken, J.S., "Fecal Bacteriotherapy for Recurrent Clostridium Difficile Infection," Anaerobe 15(6):285-289, Academic Press, United Kingdom (Dec. 2009).
Barrasa, J.I., et al., "Bile Acids in the Colon, From Healthy to Cytotoxic Molecules.," Toxicology in Vitro : an International Journal Published in Association With Bibra, 27(2):964-977, Pergamon Press , United Kingdom (Mar. 2013).
Barreau, M., et al., "Improving the Identification of Anaerobes in the Clinical Microbiology Laboratory Through MALDI-TOF Mass Spectrometry," Anaerobe, 22:123-125, Academic Press, United Kingdom (Aug. 2013).
Barrell, C.,et al., "Reduced-intensity Conditioning Allogeneic Stem Cell Transplantation in Pediatric Patients and Subsequent Supportive Care.," Oncology Nursing Forum, 39(6):451-458, Oncology Nursing Society,United States, (Nov. 2012).
Bartlett, J.G., et al., "Antibiotic-associated Pseudomembranous Colitis Due to Toxin-Producing Clostridia," The New England journal of medicine, 298(10):531-534, Massachusetts Medical Society, United States , (Mar. 1978 ).
Basler, M., et al., "Tit-for-tat: Type Vi Secretion System Counterattack During Bacterial Cell-cell Interactions," Cell, 152(4):884-894, Cell Press, United States, (Feb. 2013 ).
Basler, M., et al., "Type Vi Secretion Requires a Dynamic Contractile Phage Tail-like Structure," Nature, 483(7388):182-186, Nature Publishing Group, United Kingdom (Feb. 2012 ).
Bauer, T.M., et al., "Derivation and Validation of Guidelines for Stool Cultures for Enteropathogenic Bacteria Other Than Clostridium Difficile in Hospitalized Adults," JAMA, 285(3:313-319, American Medical Association, United States (Jan. 2001).
Beelen et al., "Influence of Intestinal Bacterial Decontamination Using Metronidazole and Ciprofloxacin or Ciprofloxacin Alone on the Development of Acute Graft-Versus-Host Disease After Marrow Transplantation in Patients with Hematologic Malignancies: Final Results and Long-Term Follow-Up of an Open-Label Prospective Randomized Trial," Blood 93(10):3267-3275 (1999).
Belkaid, Y, and Rouse, B,T., "Natural Regulatory T Cells in Infectious Disease," Nature Immunology 6(4):353-360, Nature America Inc, United States (Apr. 2005).
Ben-Amor, K., et al., "Genetic Diversity of Viable, Injured, and Dead Fecal Bacteria Assessed by Fluorescence-activated Cell Sorting and 16S rRNA Gene Analysis," Applied and Environmental Microbiology, 71(8):4679-4689, American Society for Microbiology, United States (Aug. 2005).
Bernstein, H., et al., "Bile Acids as Carcinogens in Human Gastrointestinal Cancers.," Mutation research, 589(1):47-65, Elsevier, Netherlands, (Jan. 2005).

Berst AD, A., et al., "Fecal Fat Determination With a Modified Titration Method," Scandinavian Journal of Gastroenterology, 45(5):603-607, Informa Healthcare, United Kingdom (May 2010).
Bhatia, A. et al., "Proionibacterium Acnes and Chronic Diseases," The Infectious Etiology of Chronic Diseases: Defining the Relationship, Enhancing the Research, and Mitigating the Effects: Workshop Summary., Knobler, S.L. et al. (eds.), 2004, pp. 74-80, may be downloaded at (URL:http://www.nap.edu/catalog/11026.html).
Bidawid, S., et al., "Heat Inactivation of Hepatitis a Virus in Dairy Foods," Journal of Food Protection, 63(4):522-528, International Association for Food Protection, United States (Apr. 2000).
Bloedt, K., et al., "Evaluation of New Selective Culture Media and a Rapid Fluorescence in Situ Hybridization Assay for Identification of Clostridium Difficile From Stool Samples," Journal of Medical Microbiology, 58(7):874-877, Microbiology Society, United Kingdom (Jul. 2009).
Bokulich, N.A., et al., "Quality-filtering Vastly Improves Diversity Estimates From Illumina Amplicon Sequencing," Nature Methods, 10(1):57-59, Nature Publications Group, United States (Jan. 2013).
Bolger, A.M.,et al., "Trimmomatic: a Flexible Trimmer for Illumina Sequence Data.," Bioinformatics (Oxford, England), 30(15):2114-2120, Oxford University Press, United Kingdom (Aug. 2014).
Bolivar, I., et al., "Bacterial Diversity in Oral Samples of Children in Niger With Acute Noma, Acute Necrotizing Gingivitis, and Healthy Controls," Plos Neglected Tropical Diseases, 6(3):e1556, Public Library of Science, United States (2012).
Borody, T.J., and Khoruts, A, "Fecal Microbiota Transplantation and Emerging Applications," Nature Reviews. Gastroenterology & Hepatology, 9(2):88-96, Nature Publication Group, United Kingdom (Feb. 2012).
Borody, T.J. et al. (2011). Fecal microbiota transplantation (FMT) in multiple sclerosis. Poster abstract at American College of Gastroenterology Annual Scientific Meeting and Postgraduate Course Oct. 28, 2011.
Borody, T.J., et al., "Treatment of Ulcerative Colitis Using Fecal Bacteriotherapy," Journal of Clinical Gastroenterology 37(1):42-47, Wolters Kluwer Health, Inc, United States (Jul. 2003).
Borriello, S.P., and Barclay, F.E, "An In-Vitro Model of Colonisation Resistance to Clostridium Difficile Infection," Journal of Medical Microbiology, 21(4):299-309, Microbiology Society, United Kingdom (Jun. 1986).
Borriello, S.P., and Barclay, F.E, "Protection of Hamsters Against Clostridium Difficile Ileocaecitis by Prior Colonisation With Nonpathogenic Strains," Journal of Medical Microbiology, 19(3):339-350, Microbiology Society, United Kingdom (Jun. 1985).
Borriello, S.P., and Honour, P, "Simplified Procedure for the Routine Isolation of Clostridium Difficile From Faeces," Journal of Clinical Pathology, 34(10):1124-1127, BMJ Publication Group, United Kingdom (Oct. 1981).
Borriello, S.P., "The Influence of the Normal Flora on Clostridium Difficile Colonisation of the Gut," Annals of Medicine,, 22(1):61-67, Informa Healthcare, United Kingdom (Feb. 1990).
Boyles, W.A., and Lincoln, R.E, "Separation and Concentration of Bacterial Spores and Vegetative Cells by Foam Flotation," Applied Microbiology, 6(5):327-334, American Society For Microbiology, United States (Sep. 1958).
Brandl et al., "Vancomycin-resistant enterococci exploit anti biotic-induced innate immune deficit,". Nature 455(7214):804-807 (2008).
Brandt, L.J., et al., "Long-term Follow-up of Colonoscopic Fecal Microbiota Transplant for Recurrent Clostridium Difficile Infection," The American Journal of Gastroenterology, 107(7):1079-1087, Wolters Kluwer Health, United States (Jul. 2012).
Brandt, L.J., "Fecal Transplantation for the Treatment of Clostridium Difficile Infection," Gastroenterology & Hepatology, 8(3):191-194, Gastro-Hep Communications, United States (Mar. 2012).
Brauniger, S., et al., "Further Studies on Thermal Resistance of Bovine Parvovirus Against Moist and Dry Heat," International Journal of Hygiene and Environmental Health, 203(1):71-75, Urban & Fischer, Germany (Mar. 2000).
Britton, R. A., et al., "Role of the Intestinal Microbiota in Resistance to Colonization by Clostridium Difficile," Gastroenterology 146(6):1547-1553, W.B. Saunders, United States (May 2014).

(56) References Cited

OTHER PUBLICATIONS

Broda, D.M., et al., "Efficacy of Heat and Ethanol Spore Treatments for the Isolation of Psychrotrophic *Clostridium* Spp. Associated With the Spoilage of Chilled Vacuum-packed Meats," International Journal of Food Microbiology, 39(1-2):61-68, Elsevier Science Publishers, Netherlands (Jan. 1998).

Brosius, J., et al., "Complete Nucleotide Sequence of a 16S Ribosomal RNA Gene From *Escherichia coli*," Proceedings of the National Academy of Sciences of the United States of America, 75(10):4801-4805, National Academy of Sciences, United States (Oct. 1978).

Browne, H,P., et al., "Culturing of 'unculturable' Human Microbiota Reveals Novel Taxa and Extensive Sporulation," Nature 533(7604):543-546, Nature Publishing Group, United Kingdom (May 2016).

Bueche, M., et al., "Quantification of Endospore-forming Firmicutes by Quantitative PCR With the Functional Gene Spo0A," Applied and Environmental Microbiology 79(17):5302-5312, American Society for Microbiology, United States (Sep. 2013).

Buffie, C. G., et al., "Precision Microbiome Reconstitution Restores Bile Acid Mediated Resistance to Clostridium Difficile," Nature 517(7533):205-208, Nature Publishing Group, United Kingdom (Jan. 2015).

Buffie, C.G. and Pamer, E.G., "Microbiota-mediated Colonization Resistance Against Intestinal Pathogens," Nature Reviews. Immunology 13(11):790-801, Nature Pub. Group, United Kingdom (Nov. 2013).

Buffie, C.G., et al., "Profound Alterations of Intestinal Microbiota Following a Single Dose of Clindamycin Results in Sustained Susceptibility to Clostridium Difficile-induced Colitis," Infection and Immunity, 80(1):62-73, American Society For Microbiology, United States, (Jan. 2012 ).

Burke, C.J., et al., "Formulation, Stability, and Delivery of Live Attenuated Vaccines for Human Use," Critical Reviews in Therapeutic Drug Carrier Systems, 16(1):1-83, Begell House, United States (1999).

Cani, P.D., et al., "Changes in Gut Microbiota Control Inflammation in Obese Mice Through a Mechanism Involving Glp-2-driven Improvement of Gut Permeability," Gut, 58(8):1091-1103, British Medical Association, United Kingdom (Aug. 2009).

Caporaso, J.G., et al., "QIIME Allows Analysis of High-throughput Community Sequencing Data," Nature Methods, 7(5):335-336, Nature Publishing Group, United States, (May 2010 ).

Caporaso, J.G., et al., "Ultra-High-Throughput Microbial Community Analysis on the Illumina Hiseq and Miseq Platforms," The Isme Journal, 6(8):1621-1624, Nature Publishing Group, United Kingdom (Aug. 2012).

Carlier, J.P., et al., "Proposal to Unify Clostridium Orbiscindens Winter et al. 1991 and Eubacterium Plautii (Séguin 1928) Hofstad and Aasjord 1982, With Description of *Flavonifractor plautii* Gen. Nov., Comb. Nov., and Reassignment of Bacteroides Capillosus to *Pseudoflavonifractor capillosus* Gen. Nov., Comb. Nov.," International Journal of Systematic and Evolutionary Microbiology 60(Pt 3):585-590, Microbiology Society, United Kingdom (Mar. 2010).

Carvalho, A. S., et al., "Effects of Various Sugars Added to Growth and Drying Media Upon Thermotolerance and Survival Throughout Storage of Freeze-dried *Lactobacillus delbrueckii* SSP Bulgaricus," Biotechnology Progress, 20(1):248-254, Wiley-Blackwell, United States (Jan. 2004).

Cato, E.P., et al., "Clostridium Oroticum Comb. Nov. Amended Description," International Journal of Systematic and Evolutionary Microbiology 17(1):9-13, (Jan. 1968).

Certified translation of second priority document, PCT/JP2010/071746, 79 pages, Dec. 27, 2017.

Champagne, C.P., et al., "Effect of Polymers and Storage Temperature on the Stability of Freeze-dried Lactic Acid Bacteria," Food Research International, 29(5-6):555-562 (Jun.-Aug. 1996).

Chang, J.Y., et al., "Decreased Diversity of the Fecal Microbiome in Recurrent Clostridium Difficile-Associated Diarrhea," The Journal of Infectious Diseases 197(3):435-438, Oxford University Press, United States (Feb. 2008).

Chapman, C.M.C., et al., "In Vitro Evaluation of Single- and Multi-strain Probiotics: Interspecies Inhibition Between Probiotic Strains, and Inhibition of Pathogens," Anaerobe, 18(4):405-413, Academic Press, United Kingdom (Aug. 2012).

Chen, W.,et al., "Human Intestinal Lumen and Mucosa-associated Microbiota in Patients With Colorectal Cancer.," Plos One, 7(6):39743, Public Library of Science,United States, (2012).

Chen, X., et al., "A Mouse Model of Clostridium Difficile-associated Disease," Gastroenterology, 135(6):1984-1992, W.B. Saunders, United States (Dec. 2008).

Chen, X., et al., "Overview of Clostridium Difficile Infection: Implications for China," Gastroenterology Report, 1(3):153-158, Oxford University Press and Science Digestive, United Kingdom (Nov. 2013).

English translation of Chinese First Office Action, Chinese Application No. 201380071190X, Jul. 4, 2018, 11 pages (with a concise explanation of relevance).

Chinese First Office Action, Chinese Application No. 201480019395.8, dated Jul. 17, 2017, 29 pages.

Chinese Second Office Action, Chinese Application No. 201480019395.8, dated Apr. 4, 2018 (with concise explanation of relevance), 14 pages.

Chiu, C-H. and Ou, J-T, "Rapid Identification of *Salmonella serovars* in Feces by Specific Detection of Virulence Genes, Inva and Spvc, by an Enrichment Broth Culture-multiplex Per Combination Assay," Journal of Clinical Microbiology, 34(10):2619-2622, American Society for Microbiology, United States (Oct. 1996).

Chow, J., Tang, H., and Mazmanian, S.K, "Pathobionts of the Gastrointestinal Microbiota and Inflammatory Disease," Current opinion in immunology, 23(4):473-480, Elsevier, United Kingdom (Aug. 2011).

Chromek, M.,et al., "The Antimicrobial Peptide Cathelicidin Protects Mice From *Escherichia coli* O157:h7-mediated Disease.," Plos One, 7(10):46476, Public Library of Science,United States, (2012).

Chung, H., et al., "Gut Immune Maturation Depends on Colonization With a Host-specific Microbiota," Cell 149(7):1578-1593, Cell Press, United States (Jun. 2012).

Claesson, M.J., et al., "Comparison of Two Next-generation Sequencing Technologies for Resolving Highly Complex Microbiota Composition Using Tandem Variable 16S rRNA Gene Regions," Nucleic Acids Research, 38(22):e200, Oxford University Press, United Kingdom (Dec. 2010).

Clemente, J.C., et al., "The Impact of the Gut Microbiota on Human Health: an Integrative View," Cell, 148(6):1258-1270, Cell Press, United States (Mar. 2012).

Clifford, R.J.,et al., "Detection of Bacterial 16s Rrna and Identification of Four Clinically Important Bacteria by Real-time Pcr.," Plos One, 7(11):48558, Public Library of Science,United States, (2012).

Cohen, Statistical Power Analysis for the Behavioral Sciences, Second Edition (Routledge, Hillsdale, NJ, 1988).

Coleman, W.H., "Mechanism of Killing of Spores of Bacillus Cereus and Bacillus Megaterium by Wet Heat," Letters in Applied Microbiology, 50(5):507-514, Blackwell Scientific Publications, United Kingdom (May 2010).

Collins, M,D., et al., "The Phylogeny of the Genus *Clostridium*: Proposal of Five New Genera and Eleven New Species Combinations," International Journal of Systematic Bacteriology 44(4):812-826, Society for General Microbiology, United Kingdom (Oct. 1994).

Cooke et al., "LPS antagonism reduces graft-versus-host disease and preserves graftversus-leukemia activity after experimental bone marrow transplantation," J. Clin. Invest. 107:1581-1589 (2001).

Cooke, K.R.,et al., "An Experimental Model of Idiopathic Pneumonia Syndrome After Bone Marrow Transplantation: I. The Roles of Minor H Antigens and Endotoxin.," Blood, 88(8):3230-3239, American Society of Hematology,United States, (Oct. 1996).

Copelan, E.,et al., "A Scheme for Defining Cause of Death and Its Application in the T Cell Depletion Trial.," Biology of Blood and Marrow Transplantation : Journal of the American Society for Blood and Marrow Transplantation, 13(12):1469-1476, Carden Jennings Publishing,United States, (Dec. 2017).

(56) References Cited

OTHER PUBLICATIONS

Cover Page of Science, Jan. 21, 2011, 1 page.
Cruz, M. C., et al., "Immunosuppressive and Nonimmunosuppressive Cyclosporine AnalogsAre Toxic to the Opportunistic Fungal Pathogen Cryptococcus neoformans via Cyclophilin-Dependent Inhibition of Calcineurin," Antimicrob. Agents Chemother. 44(1):143-149, American Society for Microbiology (2000).
Current Uses and Outcomes of Hematopoietic Stem Cell Transplantation 2012 CIBMTR Summary Slides, 2012.
Dabard J., et al., "Ruminococcin A, a New lantibiotic Produced by a Ruminococcus Gnavus Strain Isolated from Human Feces," Applied and Environmental Microbiology, 67(9):4111-4118, American Society for Microbiology, United States (Sep. 2001).
Das et al., "Blockade ofinterleukin-23 signaling results in targeted protection ofthe colon and allows for separation of graft-versus-host and graft-versus-leukemia responses," Blood 115(25):5249-5258 (2010).
Das, R.,et al., "Interleukin-23 Secretion by Donor Antigen-presenting Cells is Critical for Organ-specific Pathology in Graft-versus-host Disease.," Blood, 113(10):2352-2362, American Society of Hematology,United States, (Mar. 2009).
David, L.A., Maurice, C.F., Carmody, R.N., Gootenberg, D.B., Button, J.E., Wolfe, B.E., Ling, A.V., Devlin, A.S., Varma, Y., Fischbach, M.A., et al. (2013). Diet rapidly and reproducibly alters the human gut microbiome. Nature advance online publication.
De Aguiar Vallim, T.Q., et al., "Pleiotropic Roles of Bile Acids in Metabolism," Cell Metabolism, 17(5):657-669, Cell Press, United States, (May 2013).
Deangelis, M., et al., "Fecal Microbiota and Metabolome of Children With Autism and Pervasive Developmental Disorder Not Otherwise Specified," PloS One, 8(10):e76993, Public Library of Science, United States (Oct. 2013).
Defined Fecal Microbiota Transplantation for Clostridium Difficile Diarrhea. (http://clinicaltrials.gov/ct2/show/NCT01868373); Accessed Mar. 26, 2014.
Dendukuri, N., "Probiotic Therapy for the Prevention and Treatment of Clostridium Difficile-associated Diarrhea: A Systematic Review," Canadian Medical Association Journal, 173(2):167-170, Canadian Medical Association, Canada (Jul. 2005).
Derrien, M., "*Akkermansia muciniphila* Gen. Nov., Sp. Nov., a Human Intestinal Mucin-degrading Bacterium," International Journal of Systematic and Evolutionary Microbiology, 54(5):1469-1476, Microbiology Society, United Kingdom (Sep. 2004).
Derrien, M.,et al., "Modulation of Mucosal Immune Response, Tolerance, and Proliferation in Mice Colonized by the Mucin-degrader Akkermansia Muciniphila.," Frontiers in Microbiology, 2:166, Frontiers Research Foundation,Switzerland., (Aug. 2011).
Derrien, M.,et al., "Mucin-bacterial Interactions in the Human Oral Cavity and Digestive Tract.," Gut Microbes, 1(4):254-268, PA : Taylor & Francis, United States, (Jul. 2010).
Desantis, T.Z.,et al., "Greengenes, A Chimera-Checked 16S RRNA Gene Database and Workbench Compatible With ARB.," Applied and Environmental Microbiology, 72(7):5069-5072, American Society for Microbiology,United States, (Jul. 2006).
Dethlefsen, L., et al., "Incomplete Recovery and Individualized Responses of the Human Distal Gut Microbiota to Repeated Antibiotic Perturbation," Proceedings of the National Academy of Sciences of the United States of America, 108 Suppl 1:4554-4561, National Academy of Sciences, United States, (Mar. 2011).
Dethlefsen, L., "The Pervasive Effects of an Antibiotic on the Human Gut Microbiota, as Revealed by Deep 16S rRNA Sequencing," PLoS Biology, 6(11):e280, Public Library of Science, United States (Nov. 2008).
Detmer, A., and Glenting, J., "Live Bacterial Vaccines—A Review and Identification of Potential Hazards," Microbial Cell Factories, 5:23, BioMed Central, United Kingdom (Jun. 2006).
Devos, W.M., "Fame and Future of Faecal Transplantations-developing Next-generation Therapies With Synthetic Microbiomes," Microbial Biotechnology, 6(4):316-325, Wiley-Blackwell, United States (Jul. 2013).

Dewhirst, F.E., et al., "Phylogeny of the Defined Murine Microbiota: Altered Schaedler Flora," Applied and Environmental Microbiology 65(8):3287-3292, American Society for Microbiology, United States (Aug. 1999).
Dezfulian, M., et al., "Selective Medium for Isolation of Clostridium Botulinum From Human Feces," Journal of Clinical Microbiology, 13(3):526-531, American Society for Microbiology, United States (Mar. 1981).
Dharmani, P., et al., "The Probiotic Mixture VSL#3 Accelerates Gastric Ulcer Healing by Stimulating Vascular Endothelial Growth Factor," PloS One , 8(3):e58671, Public Library of Science, United States (Mar. 2013).
Diehl, G.E., et al., "Microbiota Restricts Trafficking of Bacteria to Mesenteric Lymph Nodes by Cx(3)crl(Hi) Cells," Nature, 494(7435):116-120, Nature Publishing Group, United Kingdom (Feb. 2013).
Dietrich, G., Collioud, A., and Rothen, S.A. (2008). Developing and Manufacturing Attenuated Live Bacterial Vaccines. (http://www.biopharminternational.com/biopharm/Vaccine+Manufacturing+Articles/Developing-and-Manufacturing-Attenuated-Live-Bacte/ArticleStandard/Article/detail/557306) Accessed Mar. 25, 2014.
D'Souza, D.H., and Su, X, "Efficacy of Chemical Treatments Against Murine Norovirus, Feline Calicivirus, and MS2 Bacteriophage," Foodborne Pathogens and Disease, 7(3):319-326, Mary Ann Liebert, incorporated, United States (Mar. 2010).
Dowell, V.R., et al., "Coproexammation for Botulinal Toxin and Clostridium Botulinum. A New Procedure for Laboratory Diagnosis of Botulism," JAMA, 238(17):1829-1832, American Medical Association, United States (Oct. 1977).
Dragon, D.C., and Rennie, R.P, "Evaluation of Spore Extraction and Purification Methods for Selective Recovery of Viable Bacillus Anthracis Spores," Letters in Applied Microbiology, 33(2):100-105, Blackwell Scientific Publications, United Kingdom (Aug. 2001).
Duan, J., et al., "Microbial Colonization Drives Expansion of Il-1 Receptor 1-expressing and Il-17-producing Gamma/delta T Cells," Cell host & microbe, 7(2):140-150, Cell Press, United States, (Feb. 2010).
Duc, L., et al., "Germination of the Spore in the Gastrointestinal Tract Provides a Novel Route for Heterologous Antigen Delivery," Vaccine, 21(27-30):4215-4224, Elsevier Science, Netherlands (Oct. 2003).
Duc, L.H., et al., "Bacterial Spores as Vaccine Vehicles," Infection and Immunity, 71(5):2810-2818, American Society For Microbiology, United States (May 2003).
Dumas, M.E., et al., "Metabolic Profiling Reveals a Contribution of Gut Microbiota to Fatty Liver Phenotype in Insulin-resistant Mice," Proceedings of the National Academy of Sciences of the United States of America, 103(33):12511-12516, National Academy of Sciences, United States (Aug. 2006).
Duncker, S.C.,et al., "The D-alanine Content of Lipoteichoic Acid is Crucial for Lactobacillus Plantaram-mediated Protection From Visceral Pain Perception in a Rat Colorectal Distension Model.," Neurogastroenterology and Motility : the Official Journal of the European Gastrointestinal Motility Society, 20(7):843-850, Blackwell Scientific Publications, c1994, United Kingdom (Jul. 2008).
Dutta, S.K., et al., "Efficacy of Combined Jejunal and Colonic Fecal Microbiota Transplantation for Recurrent Clostridium Difficile Infection," Clinical Gastroenterology and Hepatology, 12(9):1572-1576, W.B. Saunders for the American Gastroenterological Association, United States (Sep. 2014).
Edgar, R.C., et al., "Uchime Improves Sensitivity and Speed of Chimera Detection," Bioinformatics, 27(16):2194-2200, Oxford University Press, United Kingdom (Aug. 2011).
Edwards, A.D., and Slater, N.K.H, "Formulation of a Live Bacterial Vaccine for Stable Room Temperature Storage Results in Loss of Acid, Bile and Bile Salt Resistance," Vaccine, 26(45):5675-5678, Elsevier Science, Netherlands (Oct. 2008).
Eeckhaut, V., et al., "The Anaerobic Butyrate-producing Strain Butyricicoccus Pullicaecorum Decreases Colonic Inflammation and Ulceration in a Tnbs-induced Colitis Rat Model," 5th Probiotics, Prebiotics and New Foods Congress, 2009,1 page.

(56) References Cited

OTHER PUBLICATIONS

Eiseman, B., et al., "Fecal Enema as an Adjunct in the Treatment of Pseudomembranous Enterocolitis," Surgery, 44(5):854-859, St. Louis, MO : Mosby, United States (Nov. 1958).
Elhage, R. et al., "Emerging Trends in "Smart Probiotics": Functional Consideration for the Development of Novel Health and Industrial Applications," Frontiers in Microbiology, Sep. 2017, pp. 1-11, vol. 8, Article 1889.
El-Houssieny, R., et al., "Recovery and Detection of Microbial Contaminants in Some Non-Sterile Pharmaceutical Products," Archives of Clinical Microbiology, 4(6):1-14, Ain Shams University, Egypt (2013).
Elving, J., et al., "Composting for Avian Influenza Virus Elimination," Applied and Environmental Microbiology, 78(9):3280-3285, American Society for Microbiology, United States (May 2012).
Emanuelsson, F., et al., "Faecal Microbiota Transplantation and Bacteriotherapy for Recurrent Clostridium Difficile Infection: A Retrospective Evaluation of 31 Patients," Scandinavian Journal of Infectious Diseases, 46(2):89-97, Informa Healthcare, United Kingdom (Feb. 2014).
Endt, K., et al., "The Microbiota Mediates Pathogen Clearance From the Gut Lumen After Non-Typhoidal *Salmonella* Diarrhea," PLoS Pathogens, 6(9):e1001097, Public Library of Science, United States (Sep. 2010).
Eriguchi et al., "Graft versus-host disease disrupts intestinal microbial ecology by inhibiting Paneth cell production of a-defensins," Blood 120(1):223-231 (2012).
European Examination Report for EP Application No. EP 11728077.6, dated Sep. 18, 2015, 4 pages.
European Examination Report for EP Application No. EP 13856249.1, dated May 23, 2018, 6 pages.
European Examination Report for EP Application No. EP 14745749.3, dated Oct. 31, 2017, 3 pages.
European Examination Report for EP Application No. EP 14745792.3, dated Dec. 21, 2017, 6 pages.
European Examination Report for EP Application No. EP 14746341.8, dated Jun. 13, 2017, 11 pages.
European Examination Report for EP Application No. EP 14746341.8, dated Apr. 18, 2018, 7 pages.
European Examination Report for EP Application No. EP 14746455.6, dated Oct. 31, 2017, 6 pages.
European Examination Report for EP Application No. EP 14763266.5, dated Nov. 13, 2017, 4 pages.
European Examination Report for EP Application No. EP 14768281.9 dated Dec. 18, 2017, 4 pages.
European Examination Report for EP Application No. EP 14821918.1, dated Jan. 29, 2018, 4 pages.
European Extended Search Report, EP Application No. EP 14746455.6, dated Nov. 24, 2016, 9 pages.
European Extended Search Report for EP Application No. EP 13856249.1, dated Jan. 26, 2017, 22 pages.
European Extended Search Report for EP Application No. EP 14745749.3, dated Jan. 23, 2017, 13 pages.
European Extended Search Report for EP Application No. EP 14745792.3, dated Dec. 23, 2016, 17 pages.
European Extended Search Report for EP Application No. EP 14746341.8, dated Sep. 28, 2016, 9 pages.
European Extended Search Report for EP Application No. EP 14763266.5, dated Aug. 16, 2016, 7 pages.
European Extended Search Report for EP Application No. EP 14768281.9, dated Jul. 18, 2016, 9 pages.
European Extended Search Report for EP Application No. EP 14870947.0, dated Oct. 17, 2017, 11 pages.
European Partial Supplementary Report for EP Application No. EP 14745749.3, dated Oct. 14, 2016, 6 pages.
European Partial Supplementary Report for EP Application No. EP 14745792.3, dated Sep. 20, 2016, 10 pages.
European Partial Supplementary Search Report for EP Application No. EP 14870947.0, dated Jul. 11, 2017, 13 pages.
European Summons to Attend Oral Proceedings Pursuant to Rule 115(1) EPC for EP Application No. EP 14768281.9, mailed on Jul. 11, 2018, 10 pages.
Everard, A., et al., "Cross-talk Between Akkermansia Muciniphila and Intestinal Epithelium Controls Diet-Induced Obesity," Proceedings of the National Academy of Sciences of the United States of America, 110(22):9066-9071, National Academy of Sciences, United States (May 2013).
Evidence of Effects of Probiotics Against Antimicrobial-Related Diarrhea, Pharmacy, Paper, 12 pages, (2011).
Fairhead, H., et al., "Small, Acid-soluble Proteins Bound to DNA Protect Bacillus Subtilis Spores From Being Killed by Freeze-Drying.," Applied and Environmental Microbiology, 60(7):2647-2649, American Society for Microbiology, United States (Jul. 1994).
Faith, J.J., et al., "Identifying Gut Microbe-host Phenotype Relationships Using Combinatorial Communities in Gnotobiotic Mice," Science Translational Medicine, 6(220):220ra11, American Association for the Advancement of Science, United States (Jan. 2014).
Fakhry, S., et al., "Characterization of Spore Forming Bacilli Isolated From the Human Gastrointestinal Tract," Journal of Applied Microbiology, 105(6):2178-2186, Blackwell Science, United Kingdom (Dec. 2008).
Farache, J., et al., "Luminal Bacteria Recruit Cd103+ Dendritic Cells Into the Intestinal Epithelium to Sample Bacterial Antigens for Presentation," Immunity, 38(3):581-595, Cell Press, United States, (Mar. 2013).
Faust, et al., "Microbial Co-occurrence Relationships in the Human Microbiome," Plos Computational Biology, 8(7):e1002606, Public Library of Science, United States (Jul. 2012).
Fell Jr., N.F., et al., "Mitigating Phosphate Interference in Bacterial Endospore Detection by Tb Dipicolinate Photoluminescence," Analytica Chimica Acta, 426(11):43-50, Elsevier (Jan. 2001).
Ferreira, R.B., et al., "The Intestinal Microbiota Plays a Role in *Salmonella*-induced Colitis Independent of Pathogen Colonization," Plos One, 6(5):e20338, Public Library of Science, United States, (May 2011).
Fichtel, J., et al., "Spore Dipicolinic Acid Contents Used for Estimating the Number of Endospores in Sediments," FEMS Microbiology Ecology, 61(3):522-532, Elsevier Science Publishers on behalf of the Federation of European Microbiological Societies, United Kingdom (Sep. 2007).
Final Office Action dated Nov. 1, 2019, in U.S. Appl. No. 16/054,864, Gregory McKenzie et al., filed Aug. 3, 2018, 10 pages.
Final Office Action dated Dec. 7, 2017, in U.S. Appl. No. 14/765,812, Afeyan, N.B., et al., filed Aug. 4, 2015.
Final Office Action dated Jan. 8, 2018, in U.S. Appl. No. 14/765,810, Maltzahn, G.V., et al., filed Aug. 4, 2015.
Final Office Action dated May 11, 2017, in U.S. Appl. No. 14/777,252, Henn, M.R., et al., filed Sep. 15, 2015.
Final Office Action dated Jan. 25, 2018, in U.S. Appl. No. 14/765,810, Maltzahn, G.V., et al., filed Aug. 4, 2015.
Final Office action dated Dec. 11, 2019, in U.S. Appl. No. 14/765,812, Afey An; N. et al., filed Aug. 4, 2015, 10 pages.
Final Office action dated Jan. 18, 2019, in U.S. Appl. No. 14/765,814, Cook; D. et al., filed Aug. 4, 2015, 14 pages.
Final Office Action dated Jun. 12, 2018, in U.S. Appl. No. 15/039,007, 9 pages.
Final Office Action dated Jun. 22, 2018, in U.S. Appl. No. 14/776,676, 15 pages.
Final Office Action dated May 5, 2020, in U.S. Appl. No. 14/765,814, Cook, D. et al., filed Aug. 4, 2015, 16 pages.
Fischbach, M.A., et al., "Cell-based Therapeutics: The Next Pillar of Medicine," Science Translational Medicine, 5(179):179ps7, American Association for the Advancement of Science, United States (Apr. 2013).
Fitzpatrick, L.R., "Probiotics for the treatment of Clostridium difficile associated disease", World Journal of Gastrointestinal Pathophysiology, 4(3): 47-52, Baishideng Publishing Group, United States (Aug. 2013).
Foditsch, C., et al., "Isolation and Characterization of Faecalibacterium prausnitzii from Calves and Piglets," PLOS One, 9(12):e116465, Public Library of Science, United States (Dec. 31, 2014).

(56) References Cited

OTHER PUBLICATIONS

Fonseca, F., et al., "Operating Conditions That Affect the Resistance of Lactic Acid Bacteria to Freezing and Frozen Storage," Cryobiology, 43(3):189-198, Elsevier, Netherlands (Nov. 2001).
Frank, D.N., et al., "Molecular-phylogenetic Characterization of Microbial Community Imbalances in Human Inflammatory Bowel Diseases," Proceedings of the National Academy of Sciences of the United States of America 104(34):13780-13785, National Academy of Sciences, United States (Aug. 2007).
Franz, C.M.A.P., et al., "Enterococci as Probiotics and Their Implications in Food Safety," International Journal of Food Microbiology, 151(2):125-140, Elsevier Science Publishers, Netherlands (Dec. 2011).
Freifeld et al., "Clinical Practice Guideline for the Use of Antimicrobial Agents in Neutropenic Patients with Cancer: 2010 Update by the Infectious Diseases Society of America," Clinical Infectious Diseases 52(4):e56-e93 (2011).
Friedman-Moraco, R.J., et al., "Fecal Microbiota Transplantation for Refractory Clostridium Difficile Colitis in Solid Organ Transplant Recipients.," American Journal of Transplantation, 14(2):477-480, Wiley-Blackwell on behalf of the American Society of Transplant Surgeons and the American Society of Transplantation, United States (Feb. 2014).
Fuentes, S., Van Nood, E., Tims, S., Heikamp-De Jong, I., Ter Braak, C.J., Keller, J.J., Zoetendal, E.G., and Devos, W.M. (2014). Reset of a critically disturbed microbial ecosystem: faecal transplant in recurrent Clostridium difficile infection. The ISME Journal.
Furusawa, Y., et al., "Commensal Microbe-derived Butyrate Induces the Differentiation of Colonic Regulatory T Cells ," Nature 504(7480):446-450, Nature Publishing Group, United Kingdom (Dec. 2013).
Gaboriau-Routhiau, V., et al., "The Key Role of Segmented Filamentous Bacteria in the Coordinated Maturation of Gut Helper T Cell Responses," Immunity 31(4):677-689, Cell Press, United States (Oct. 2009).
Gallo, R.L and Hooper, L.V, "Epithelial Antimicrobial Defence of the Skin and Intestine," Nature Reviews Immunology , 12(7):503-516, Nature Publishing Group, United Kingdom (Jun. 2012).
Ganesh et al., "Commensal Akkermansia muciniphila Exacerbates Gut Inflammation in *Salmonella typhimurium*-Infected Gnotobiotic Mice," PLoS ONE 8(9):e74963 (2013).
GenBank: Accession No. NR 118589.1, accessed on Jun. 20, 2020.
GenBank HQ819637, "Uncultured Organism Clone ELU0180-T56-SNIPCRAMgANa_ 000311 Small Subunit Ribosomal RNA Gene, Partial Sequence," Jul. 30, 2012, 1 page, [Online] [Retrieved on Aug. 21, 2014] Retrieved from the Internet (URL:http://www.ncbi.nlm.nih.gov/nuccore/HQ819637).
Geuking, M.B., et al., "Intestinal Bacterial Colonization Induces Mutualistic Regulatory T Cell Responses," Immunity 34(5):794-806, Cell Press, United States (May 2011).
Gevers, D., et al., "The Treatment-naive Microbiome in New-Onset Crohn's Disease," Cell Host & Microbe, 15(3):382-392, Cell Press, United States (Mar. 2014).
Giel, J.L., et al., "Metabolism of Bile Salts in Mice Influences Spore Germination in Clostridium Difficile," Plos One, 5(1):e8740, Public Library of Science, United States, (Jan. 2010).
Gilligan, P.H. (2013). Identification of Pathogens by Classical Clinical Tests. In The Prokaryotes, E. Rosenberg, E.F. Delong, S. Lory, E. Stackebrandt, and F. Thompson, eds. (Springer Berlin Heidelberg), pp. 57-89.
Goldberg et al., "T Cell-Depleted Stem Cell Transplantation for Adults with High-Risk Acute Lymphoblastic Leukemia: Long-Term Survival for Patients in First Complete Remission with a Decreased Risk of Graft-versus-Host Disease," Biol. Blood Marrow Transplant 19:208-213 (2013).
Goodman, N.S., et al., "Biphasic System for Separation of Spores and Crystals of Bacillus Thuringiensis," Journal of Bacteriology, 94(2):485, American Society for Microbiology, United States (Aug. 1967).

Goodman,A.L., et al., "Extensive Personal Human Gut Microbiota Culture Collections Characterized and Manipulated in Gnotobiotic Mice," Proceedings of the National Academy of Sciences of the United States of America 108(15):6252-6257, National Academy of Sciences, United States (Apr. 2011).
Gough, E., et al., "Systematic Review of Intestinal Microbiota Transplantation (Fecal Bacteriotherapy) for Recurrent Clostridium Difficile Infection," Clinical Infectious Diseases, 53(10):994-1002, The University of Chicago Press, United States (Nov. 2011).
Gould, G.W., and Sale, A.J, "Initiation of Germination of Bacterial Spores by Hydrostatic Pressure," Journal of General Microbiology, 60(3):335-346, Society for General Microbiology, United Kingdom (Mar. 1970).
Grabow, W.O., et al., "Elimination of Viruses, Phages, Bacteria and Cryptosporidium by a New Generation Aquaguard Point-of-use Water Treatment Unit," International Journal of Hygiene and Environmental Medicine, 202(5):399-410, Gustav Fischer Verlag, Germany (Sep. 1999).
Grangette et al., "Enhanced antiinflammatory capacity of a Lactobacillus plantarum mutant synthesizing modified teichoic acids," PNAS 102(29): 10321-10326 (2005).
Greenway, F., et al., "A Novel Cobiotic Containing a Prebiotic and an Antioxidant Augments the Glucose Control and Gastrointestinal Tolerability of Metformin: A Case Report," Beneficial Microbes, 5(1):29-32, Wageningen Academic Publishers, Netherlands (Mar. 2014).
Grehan, M.J., et al., "Durable Alteration of the Colonic Microbiota by the Administration of Donor Fecal Flora," Journal of Clinical Gastroenterology 44(8):551-561, Wolters Kluwer Health, Inc, United States (Sep. 2010).
Grimoud, J., et al., "In Vitro Screening of Probiotic Lactic Acid Bacteria and Prebiotic Glucooligosaccharides to Select Effective Synbiotics," Anaerobe, 16(5):493-500, Academic Press, United Kingdom (Oct. 2010).
Gupta, R.K., et al., "Differentiation Between Heat Resistance and Octyl Alcohol Resistance of the Cells of Bacillus Cereus T," Biochemical and Biophysical Research Communications, 38(1):23-30, Elsevier, United States (Jan. 1970).
Gut definition. Merriam Webster Dictionary. https://www.merriamwebster. com/dictionary/gut, retrieved Mar. 9, 2020.
Hahn et al., "Risk factors for Acute Graft-Versus-Host Disease after Human Leukocyte Antigen-Identical Sibling Transplants for Adults With Leukemia," J Clin. Oncol. 26(35):5728-5734 (2008).
Hall, B.G., et al., "Building Phylogenetic Trees From Molecular Data With Mega," Molecular biology and Evolution, 30(5):1229-1235, Oxford University Press, United States, (May 2013).
Halmann, M., et al., "Stages in Germination of Spores of Bacillus Licheniformis," Journal of Bacteriology, 84(6):1187-1193, American Society for Microbiology, United States (Dec. 1962).
Hamil Ton, M.J., et al., "Standardized Frozen Preparation for Transplantation of Fecal Microbiota for Recurrent Clostridium Difficile Infection," The American Journal of Gastroenterology, 107(5):761-767, Wolters Kluwer Health, United States (May 2012).
Hamilton, M.J., et al., "High-throughput Dna Sequence Analysis Reveals Stable Engraftment of Gut Microbiota Following Transplantation of Previously Frozen Fecal Bacteria," Gut Microbes, 4(2):125-135, Philadelphia, United States, (Mar.-Apr. 2013).
Hand, T.W., et al., "Acute Gastrointestinal Infection Induces Long-lived Microbiota-specific T Cell Responses," Science, 337(6101):1553-1556, American Association for the Advancement of Science, United States, (Sep. 2012).
Hansen, A.K. et al., "Handbook of Laboratory Animal Bacteriology," Second Edition, CRC Press, 2015, p. 158 (3 total pages).
Harmsen, H. J. M., et al., "Comparison of Viable Cell Counts and Fluorescence in Situ Hybridization Using Specific rRNA-based Probes for the Quantification of Human Fecal Bacteria," FEMS Microbiology Letters, 183(1):125-129, Oxford Oxford University Press, United Kingdom (Feb. 2000).
Harrison, F, "Bacterial Cooperation in the Wild and in the Clinic: Are Pathogen Social Behaviours Relevant Outside the Laboratory?," BioEssays , 35(2):108-112, Wiley, United States (Feb. 2013).

(56) References Cited

OTHER PUBLICATIONS

Hasan, J.A., et al., "In Vitro Production of Clostridium Difficile Spores for Use in the Efficacy Evaluation of Disinfectants: a Precollaborative Investigation," Journal of AOAC International, 94(1):259-272, Aoac International, United States (Jan. 2011).
Hata, D.J. et al., "Blood Group B Degrading Activity of Ruminococcus Gnavus Alpha-Galactosidase," Artif. Cells Blood Substit. Immobil. Biotechnol., May 2004, pp. 263-274, vol. 32, No. 2.
Hayashi, H., et al., "Phylogenetic Analysis of the Human Gut Microbiota Using 16s Rdna Clone Libraries and Strictly Anaerobic Culture-based Methods," Microbiology and Immunology 46(8):535-548, Wiley-Blackwell, Australia (2002).
Hayashi, Y., et al., "Western Blot (Immunoblot) Assay of Small, Round-structured Virus Associated With an Acute Gastroenteritis Outbreak in Tokyo," Journal of Clinical Microbiology, 27(8):1728-1733, American Society for Microbiology, United States (Aug. 1989).
Hazenberg, M.P., et al., "Conversion of Germ-free Mice to the Normal State by Clostridia," Zeitschrift für Versuchstierkunde 18(4):185-190, Gustav Fischer Verlag, Germany (1976).
Heeg, D et al., "Spores of Clostridium dif.ficile Clinical Isolates Display a Diverse Germination Response to Bile Salts," PLoS One 7(2):e32381 (2012).
Hell, M., et al., "Probiotics in Clostridium Difficile Infection: Reviewing the Need for a Multistrain Probiotic," Beneficial Microbes, 4(1):39-51, Wageningen Academic Publishers, Netherlands (Mar. 2013).
Hemmerling, A., et al., "Phase 2a Study Assessing Colonization Efficiency, Safety, and Acceptability of Lactobacillus crispatus CTV-05 in Women With Bacterial Vaginosis," Sexually Transmitted Diseases, 37(12):745-750 (Dec. 2010).
Herron, P.R., and Wellington, E.M.H, "New Method for Extraction of Streptomycete Spores From Soil and Application to the Study of Lysogeny in Sterile Amended and Nonsterile Soil," Applied and Environmental Microbiology, 56(5):1406-1412, American Society for Microbiology, United States (May 1990).
Hewitt, J., et al., "Evaluation of Murine Norovirus as a Surrogate for Human Norovirus and Hepatitis a Virus in Heat Inactivation Studies," Journal of Applied Microbiology, 107(1):65-71, Oxford : Published for the Society for Applied Bacteriology by Blackwell Science, United Kingdom (Jul. 2009).
Hickson, M., "Probiotics in the Prevention of Antibiotic-associated Diarrhoea and Clostridium Difficile Infection," Therapeutic Advances in Gastroenterology, 4(3):185-197, Sage Publications, United Kingdom (May 2011).
Hiemenz, "Management of Infections Complicating Allogeneic Hematopoietic Stem Cell Transplantation," Semin Hematol 46:289-312 (2009).
Hill, D.A., et al., "Commensal bacteria-derived signals regulate basophil hematopoiesis and allergic inflammation," Nat Med., 18(4):538-546 (2012).
Hindle, A.A., and Hall, E.A.H, "Dipicolinic Acid (DPA) Assay Revisited and Appraised for Spore Detection," The Analyst, 124(11):1599-1604 (1999).
Hirsch, E.B., and Tam, V.H, "Detection and Treatment Options for Klebsiella Pneumoniae Carbapenemases (KPCS): an Emerging Cause of Multidrug-Resistant Infection," The Journal of Antimicrobial Chemotherapy, 65(6):1119-1125, Oxford University Press, United Kingdom (Jun. 2010).
Hofsten, B.V., "Partition of *Escherichia coli* in an Aqueous Polymer Two-phase System," Experimental Cell Research, 41(1):117-123 (Jan. 1966).
Holdeman, L,V., et al., "Human Fecal Flora: Variation in Bacterial Composition Within Individuals and a Possible Effect of Emotional Stress," Applied and Environmental Microbiology 31(3):359-375, American Society for Microbiology, United States (Mar. 1976).
Holler et al., "Metagenomic Analysis of the Stool Microbiome in Patients Receiving Allogeneic Stem Cell Transplantation: Loss of Diversity Is Associated with Use of Systemic Antibiotics and More Pronounced m Gastrointestinal Graft-versus-Host Disease," Biol. Blood Marrow Transplant. 20:640-645 (2014).
Holmes, E., et al., "Therapeutic Modulation of Microbiota-Host Metabolic Interactions," Science Translational Medicine, 4(137) :137rv6, American Association for the Advancement of Science, United States (Jun. 2012).
Holt G. J., et al., "Bergey's Manual of Determinative Bacteriology," Ninth Edition, 1994, pp. 527, 531, 577, 579 (6 pages total).
Honda, K., et al., "Regulations of T cell responses by intestinal commensal bacteria," Journal of Intestinal Microbiology 25(2):103-104, (Apr. 2011).
Hong et al., "1H NMR-based Metabonomic Assessment of Probiotic Effects in a Colitis Mouse Model," Arch Pharm Res 33(7): 1091-1101 (2010).
Hoppe, B., et al., "Efficacy and Safety of Oxalobacter Formigenes to Reduce Urinary Oxalate in Primary Hyperoxaluria," Nephrology, Dialysis, Transplantation, 26(11):3609-3615, Oxford University Press, United Kingdom (Nov. 2011).
Hoyles, L., et al., "Recognition of Greater Diversity of Bacillus Species and Related Bacteria in Human Faeces," Research in Microbiology, 163(1):3-13, Elsevier, France (Jan. 2012).
Hue et al., "Interleukin-23 drives innate and T cell-mediated intestinal inflammation," JEM 203(11):2473-2483 (2006).
Human Microbiome Project Consortium, "Structure, Function and Diversity of the Healthy Human Microbiome," Nature, 486(7402):207-214, Nature Publishing Group, United Kingdom (Jun. 2012).
Hurst, C.J., and Gerba, C.P, "Fate of Viruses During Wastewater Sludge Treatment Processes," Critical Reviews in Environmental Control, 18(4):317-343 (Jan. 2009).
Huse, S.M., et al., "Exploring Microbial Diversity and Taxonomy Using SSU rRNA Hypervariable Tag Sequencing," PLoS Genetics 4(11):e1000255, Public Library of Science, United States (Nov. 2008).
ICI Wrap-up Report Immunology in the 21st Century: Defeating Infection, Autoimmunity, Allergy and Cancer, 14th International Congress of Immunology, Aug. 22-27, 2010, Japan, 1 page.
International Search Report and Patentability for Application No. PCT/US2016/063697, dated May 29, 2018, Button et al., "Designed Bacterial Compositions," filed Nov. 23, 2016, 27 pages.
International Search Report and Written Opinion for Application No. PCT/US2016/041538, dated Sep. 23, 2016, Cook., et al., "Methods of Treating Colitis," filed Jul. 8, 2016, 12 Pages.
International Search Report and Written Opinion for International Application No. PCT/US13/71758, Alexandria, Virginia, dated May 5, 2014, 37 pages.
International Search Report and Written Opinion for International Application No. PCT/US14/14738, Alexandria, Virginia, dated Jul. 30, 2014, 26 pages.
International Search Report and Written Opinion for International Application No. PCT/US14/14744, Alexandria, Virginia, dated May 21, 2014, 26 pages.
International Search Report and Written Opinion for International Application No. PCT/US14/14745, Alexandria, Virginia, dated Jul. 30, 2014, 25 pages.
International Search Report and Written Opinion for International Application No. PCT/US14/14747, Alexandria, Virginia, dated Jun. 13, 2014, 17 pages.
International Search Report and Written Opinion for International Application No. PCT/US14/70684, Alexandria, Virginia, dated Jun. 10, 2015, 11 pages.
International Search Report and Written Opinion for International Application No. PCT/US2014/029539, Alexandria, Virginia, dated Oct. 10, 2014, 12 pages.
International Search Report and Written Opinion for International Application No. PCT/US2014/030817, Alexandria, Virginia, dated Dec. 5, 2014, 15 pages.
International Search Report and Written Opinion for International Application No. PCT/US2014/067491, European Patent Office, H V Rijswijk, dated Apr. 2, 2015, 12 pages.
International Search Report and Written Opinion for International Application No. PCT/US2016/063697, European Patent Office, H V Rijswijk, dated May 19, 2017, 24 pages.

(56) References Cited

OTHER PUBLICATIONS

International Search Report dated Apr. 14, 2016 in International Application No. PCT/US2015/062734.
International Search Report for International Application No. PCT/US2015/31627, ISA/US, Commissioner for Patents, Alexandria, Virginia, dated Sep. 8, 2015.
International Statistical Classification of Diseases and Related Health Problems 1 O'h Review, Chapter 1: Certain Infectious and Parasitic Diseases (AOO-B99), 2016, 2 pages.
Israel Office Action, Israel Application No. 238973, dated Apr. 20, 2017, 4 pages (with concise explanation of relevance).
Itoh, K., et al., "Characterization of Clostridia Isolated From Faeces of Limited Flora Mice and Their Effect on Caecal Size When Associated With Germ-Free Mice," Laboratory Animals 19(2):111-118, Sage, United Kingdom (Apr. 1985 ).
Itoh, K., et al., "Colonization Resistance Against Pseudomonas Aeruginosa in Gnotobiotic Mice," Laboratory Animals 20(3):197-201, Laboratory Animals Ltd, United Kingdom (Jul. 1986).
Itoh, K., et al., "Intestinal Bacteria Antagonistic to Clostridium Difficile in Mice," Laboratory Animals 21(1):20-25, Laboratory Animals Ltd, United Kingdom (Jan. 1987).
Ivanov, I.I., et al., "Induction of intestinal Th 17 cells by segmented filamentous bacteria," Cell, 139(3):485-498 (2009).
Ivanov, I.I., et al., "Specific Microbiota Direct the Differentiation of Il-17-Producing T-Helper Cells in the Mucosa of the Small Intestine," Cell Host Microbe 4(4):337-349, Cell Press, United States (Oct. 2008) including supplemental data.
Jacobs et al., "1H NMR metabolite profiling of feces as a tool to assess the impact of nutrition on the human microbiome," NMR in Biomedicine 21:615-626 (2008).
Jaffe et al., "Prevention of Peritransplantation Viridans Streptococcal Bacteremia with Early Vancomycin Administration: A Single-Center Observational Cohort Study," Clin Infect Dis. 39:1625-1632 (2004).
Jagasia et al., "Risk factors for acute GVHD and survival after hematopoietic cell transplantation," Blood 119(1):296-307 (2012).
Jakubowski et al., "T Cell-Depleted Unrelated Donor Stem Cell Transplantation Provides Favorable Disease-Free Survival for Adults with Hematologic Malignancies," Biol. Blood Marrow Transplant 17:1335-1342 (2011).
Jalanka-Tuovinen, J., et al., (2013). Faecal microbiota composition and host-microbe cross-talk following gastroenteritis and in postinfectious irritable bowel syndrome. Gut 0, 1-9.
Janda, J.M., et al., "16S rRNA Gene Sequencing for Bacterial Identification in the Diagnostic Laboratory: Pluses, Perils, and Pitfalls," Journal of Clinical Microbiology, 45(9):2761-2764, American Society for Microbiology, United States (Sep. 2007).
Janeway, C.A. et al., "Autoimmune Responses are Directed Against Self Antigens," Immunobiology: The Immune System in Health and Disease, 51th Edition, Garland Science, 2001, pp. 1-14.
Janeway, C.A. et al., Immuno Biology, 61th Edition, Garland Science Publishing, 2005, p. 414.
Japanese First Office Action, Japanese Application No. 2015-544179, dated Sep. 19, 2017, 8 pages.
Japanese Office Action, Japanese Application No. 2015-556240, dated Jun. 5, 2018, 5 pages.
Japanese Office Action, Japanese Application No. 2015-556240, dated Oct. 3, 2017, 8 pages.
Japanese Office Action, Japanese Application No. 2015-556241, dated Sep. 26, 2017, 12 pages.
Japanese Office Action, Japanese Application No. JP2016-502561, dated Feb. 6, 2018, 10 pages.
Jarry, A., et al., "Mucosal IL-10 and TGF-Beta Play Crucial Roles in Preventing LPS-driven, IFN-gamma-mediated Epithelial Damage in Human Colon Explants," The Journal of Clinical Investigation, 118(3):1132-1142, American Society for Clinical Investigation, United States (Mar. 2008).
Jawetz, et al., "Chapter 11: Spore-Forming Gram-Positive Bacilli: Bacillus and Clostridium Species," Jawetz, Melnick&Adelberg's Medical Microbiology, 26e:1-15 (Mar. 7, 2017).

Jeffs, L.B., and Khachatourians, G.G, "Estimation of Spore Hydrophobicity for Members of the Genera *Beauveria, Metarhizium*, and *Tolypocladium* by Salt-mediated Aggregation and Sedimentation," Canadian Journal of Microbiology, 43(1):23-28 (1997).
Jenq et al., "Intestinal Blautia Is Associated with Reduced Death from Graft-versus-Host Disease," Biology of Blood and Marrow Transplantation 21:1373-1383 (2015).
Jenq et al., "Regulation of intestinal inflammation by microbiota following allogeneic bone marrow transplantation," J Exp. Med. 209(5):903-911 (2012).
Jensen, N.S., and Canale-Parola, E, "Bacteroides *Pectinophilus* Sp. Nov. And Bacteroides *Galacturonicus* Sp. Nov.: Two Pectinolytic Bacteria From the Human Intestinal Tract.," Applied and Environmental Microbiology, 52(4):880-887, American Society for Microbiology, United States (Oct. 1986).
Johansson et al., "The two mucus layers of colon are organized by the MUC2 mucin, whereas the outer layer is a legislator of host-microbial interactions," PNAS 108(Suppl. 1):4659-4665 (2011).
Johnson, S., et al., "Is Primary Prevention of Clostridium Difficile Infection Possible With Specific Probiotics?," International Journal of Infectious Diseases, 16(11):e786-e792, Elsevier, Canada (Nov. 2012).
Johnston, R., et al., "Method To Facilitate the Isolation of Clostridium Botulinum Type E," Journal of Bacteriology, 88(5):1521-1522, American Society for Microbiology, United States (Nov. 1964).
Jones et al., "Mortality and Gross Pathology of Secondary Disease in Germfree Mouse Radiation Chimeras," Radiat Res. 45(3):577-588 (1971).
Jones, M.L., et al., "Cholesterol Lowering and Inhibition of Sterol Absorption by Lactobacillus Reuteri NCIMB 30242: a Randomized Controlled Trial," European Journal of Clinical Nutrition, 66(11):1234-1241, Nature Publishing Group, United Kingdom (Nov. 2012).
Jones, M.L., et al., "Cholesterol-lowering Efficacy of a Microencapsulated Bile Salt Hydrolase-active Lactobacillus Reuteri Ncimb 30242 Yoghurt Formulation in Hypercholesterolaemic Adults.," The British Journal of Nutrition, 107(10):1505-1513, Wallingford, United Kingdom (May 2012).
Joosten, H., et al., "*Salmonella* Detection in Probiotic Products," International Journal of Food Microbiology, 110(1):104-107, Elsevier Science Publishers, Netherlands (Jul. 2006).
Jordan, F., et al., "Network Ecology: Topological Constraints on Ecosystem Dynamics," Physics of Life Reviews, 1(3): 139-172, (Dec. 2004).
Jorgensen, J.H., and Ferraro, M.J, "Antimicrobial Susceptibility Testing: a Review of General Principles and Contemporary Practices," Clinical Infectious Diseases, 49(11):1749-1755, Oxford University Press,United States (Dec. 2009).
Jorup-Ronstrom, C., et al., "Fecal Transplant Against Relapsing Clostridium Difficile-associated Diarrhea in 32 Patients," Scandinavian Journal of Gastroenterology, 47(5):548-552, Informa Healthcare, United Kingdom (May 2012).
Jousimifs-Somer, H., Summanen, P., Citron, D.M., Baron, E.J., Wexler, H.M., and Finegold, S.M. (2002). Wadsworth—KLT Anaerobic Bacteriology Manual, 6th edition (California: Star), pp. 55-74, 81-132, 165-185.
Kailasapathy, K., "Microencapsulation of Probiotic Bacteria: Technology and Potential Applications," Current Issues in Intestinal Microbiology, 3(2):39-48, Horizon Scientific Press, United Kingdom (Sep. 2002).
Kakihana, K., et al., "Fecal Microbiota Transplantation for Patients with Steroid-Resistant Acute Graft-Versus-Host Disease of the Gut," Blood 128(16):2083-2088, American Society of Hematology, United States (Oct. 2016).
Kamboj et al., "Clostridium difficile Infection after Allogeneic Hematopoietic Stem Cell Transplant: Strain Diversity and Outcomes Associated with NAP1/027," Biol. Blood Marrow Transplant 20:1626-1633 (2014).
Kamboj et al., "The Changing Epidemiology of Vancomycin-Resistant Enterococcus (VRE) Bacteremia m Allogeneic Hematopoietic Stem Cell Transplant (HSCT) Recipients," Biol Blood Marrow Transplant 16:1576-1581 (2010).

(56) References Cited

OTHER PUBLICATIONS

Kamiya, S., et al., "Recovery of Spores of Clostridium Difficile Altered by Heat or Alkali," Journal of Medical Microbiology, 28(3):217-221, Microbiology Society, United Kingdom (Mar. 1989).
Kanamoto, T. et al., "Genetic Heterogeneities and Phenotypic Characteristics of Strains of The Genus *Abiotrophia* and Proposal of *Abiotrophia para-adiacens* sp. nov.," Journal of Clinical Microbiology, Feb. 2000, pp. 492-498, vol. 38, No. 2; Abiotropia para-adjacens gene for 16S rRNA, partial sequence, strain: Nucleotide: NCBI: GenBank: AB022027.1, last accessed Mar. 12, 2014, p. 8.
Kanehisa Laboratories. KEGG: Kyoto encyclopedia of genes and genomes. (http://www.genome.jp/kegg/); Accessed Mar. 27, 2014.
Kang, D.J., et al., "Clostridium scindens baiCD and baiH genes encode stereo-specific 7a/7~-hydroxy-3-oxo-114-cholenoic acid oxidoreductases," Biochim Biophys Acta 1781(1-2): 16-25 (2008).
Karasawa, T., et al., "A Defined Growth Medium for Clostridium Difficile," Microbiology, 141(2):371-375, Kluwer Academic/Plenum Publishers, United States (Feb. 1995).
Kaz Amias, M. and Sperry, J, "Enhanced Fermentation of Mannitol and Release of Cytotoxin by Clostridium Difficile in Alkaline Culture Media," Applied and Environmental Microbiology, 61(6):2425-2427, American Society for Microbiology, United States (Jun. 1995).
Kelly, D., et al., "Commensal Anaerobic Gut Bacteria Attenuate Inflammation by Regulating Nuclear-cytoplasmic Shuttling of PPAR-gamma and Rela," Nature Immunology, 5(1):104-112, Nature America Incorporated, United States (Jan. 2004).
Kelly, D., et al., "Commensal Gut Bacteria: Mechanisms of Immune Modulation," Trends in Immunology 26(6):326-333, Elsevier Science Ltd, United Kingdom (Jun. 2005).
Keynan, Y., et al., "The Role of Regulatory T Cells in Chronic and Acute Viral Infections," Clinical Infectious Diseases 46(7):1046-1052, Oxford University Press, United states (Apr. 2008).
Khoruts, A. (2013). How Does Fecal Microbiota Transplantation Treat Clostridium difficile Infection? (https://www.genome.gov/Multimedia/Siides/HumanMicrobiomeScience2013/39_Khoruts.pdf) Accessed Mar. 21, 2014.
Khoruts, A., and Sadowsky, M.J, "Therapeutic Transplantation of the Distal Gut Microbiota," Mucosal Immunology, 4(1):4-7, Nature Publishing Group, United States (Jan. 2011).
Khoruts, A., et al., "Changes in the Composition of the Human Fecal Microbiome After Bacteriotherapy for Recurrent Clostridium Difficile-associated Diarrhea," Journal of Clinical Gastroenterology 44(5):354-360, Wolters Kluwer Health, United states (May 2010 ).
Kim, B., et al., "Bacteraemia Due to Tribe Proteeae: a Review of 132 Cases During a Decade (1991-2000)," Scandinavian Journal of Infectious Diseases, 35(2):98-103, nforma Healthcare, United Kingdom (2003).
Kim, J.Y., et al., "Effect of Oral Probiotics (Bifidobacterium Lactis AD011 and Lactobacillus Acidophilus AD031) Administration on Ovalbumin-induced Food Allergy Mouse Model," Journal of Microbiology and Biotechnology, 18(8):1393-1400, Korean Society for Microbiology and Biotechnology, Korea (Aug. 2008).
Kim, S.W.,et al., "Treatment of Refractory or Recurrent Clostridium Difficile Infection," The Korean Journal of Gastroenterology = Taehan Sohwagi Hakhoe Chi, 60(2):71-78, Korean Society of Gastroenterology, [2003],Korea (South), (Aug. 2012).
Kinnebrew, M.A., et al., "Early Clostridium Difficile Infection During Allogeneic Hematopoietic Stem Cell Transplantation," Plos One, 9(3):e90158, Public Library of Science, United States, (Mar. 2014).
Kitahara, M., et al., "Assignment of *Eubacterium* sp. VPI 12708 and Related Strains with High Bile Acid 7alpha-dehydroxylating Activity to Clostridium Scindens and Proposal of *Clostridium hylemonae* sp. nov., Isolated from Human Faeces," International Journal of Systematic and Evolutionary Microbiology 50(3):971-978, Microbiology Society, United Kingdom (May 2000).
Klayraung, S., et al., "Development of Tablets Containing Probiotics: Effects of Formulation and Processing Parameters on Bacterial Viability," International Journal of Pharmaceutics, 370(1-2):54-60, Elsevier/North-Holland Biomedical Press, Netherlands (Mar. 2009).
Koeth, R.A., et al., "Intestinal Microbiota Metabolism of L-carnitine, a Nutrient in Red Meat, Promotes Atherosclerosis," Nature Medicine, 19(5):576-585, Nature Publishing Company, United States, (May 2013).
Kollmann, M., et al., "Design Principles of a Bacterial Signalling Network," Nature, 438(7067):504-507, Nature Publishing Group, United Kingdom (Nov. 2005).
Kong, Q., et al., "Oral Administration of Clostridium Butyricum for Modulating Gastrointestinal Microflora in Mice," Current Microbiology, 62(2):512-517, Springer International, United States (Feb. 2011).
Konstantinidis, K.T., et al., "The Bacterial Species Definition in the Genomic Era," Philosophical Transactions of the Royal Society of London. Series B, Biological Sciences, 361(1475):1929-1940, Royal Society, United Kingdom (Nov. 2006).
Koonin, E.V. (2002). Chapter 22 The clusters of orthologous groups (COGS) database: Phylogenetic classification of proteins from complete genomes. (http://www.ncbi.nlm.nih.gov/books/NBK21090/pdf/ch22.pdf) Accessed Mar. 27, 2014.
Koransky, J.R., et al., "Use of Ethanol for Selective Isolation of Sporeforming Microorganisms," Applied and Environmental Microbiology, 35(4):762-765, American Society for Microbiology, United States (Apr. 1978).
Kort, R., et al., "Assessment of Heat Resistance of Bacterial Spores from Food Product Isolates by Fluorescence Monitoring of Dipicolinic Acid Release," Applied and Environmental Microbiology, 71 (7):3556-3564 (2005).
Krishna, S.G., et al., "Risk Factors, Preemptive Therapy, and Antiperistaltic Agents for Clostridium Difficile Infection in Cancer Patients," Transplant Infectious Disease, 15(5):493-501, Munksgaard, Denmark, (Oct. 2013 ).
Krogius-Kurikka, L., et al., "Sequence Analysis of Percent G+C Fraction Libraries of Human Faecal Bacterial Dna Reveals a High Number of Actinobacteria," BMC Microbiology 9:68, BioMed Central, United Kingdom (Apr. 2009).
Kucerova, Z., et al., "Purification of Enterocytozoon bieneusi Spores from Stool Specimens by Gradient and Cell Sorting Techniques," Journal of Clinical Microbiology, 42(7):3256-3261 (2004).
Kumar, M., et al., "Cholesterol-lowering Probiotics as Potential Biotherapeutics for Metabolic Diseases," Experimental Diabetes Research, 2012:902917, Hindawi Publishing Corporation, United States (2012).
Kump, P.K., et al., "Alteration of Intestinal Dysbiosis by Fecal Microbiota Transplantation Does Not Induce Remission in Patients With Chronic Active Ulcerative Colitis," Inflammatory Bowel Disease, 19(10):2155-2165, Oxford University Press, United Kingdom (Sep. 2013).
Kunde, S., et al., "Safety, Tolerability, and Clinical Response After Fecal Transplantation in Children and Young Adults With Ulcerative Colitis," Journal of Pediatric Gastroenterology and Nutrition, 56(6):597-601, Lippincott Williams & Wilkins, United States (Jun. 2013).
Kyne, L., et al., "Health Care Costs and Mortality Associated With Nosocomial Diarrhea Due to Clostridium Difficile," Clinical Infectious Diseases, 34(3):346-353, Oxford University Press, United States, (Feb. 2002).
Landy, J., et al., "Review Article: Faecal Transplantation Therapy for Gastrointestinal Disease," Alimentary pharmacology & therapeutics 34(4):409-415, Wiley-Blackwell, United Kingdom (Aug. 2011).
Langille, M.G., et al., "Predictive Functional Profiling of Microbial Communities Using 16s Rrna Marker Gene Sequences," Nature biotechnology, 31(9):814-821, Nature America Publishing, United States, (Sep. 2013).
Langrish et al., "IL-12 and IL-23: master regulators of innate and adaptive immunity," Immunological Reviews 202:96-105 (2004).
LaRocco et al., "Infection in the Bone Marrow Transplant Recipient and Role of the Microbiology Laboratory in Clinical Transplantation," Clinical Microbiology Reviews 1 0(2):277-297 (1997).

(56) References Cited

OTHER PUBLICATIONS

Lathrop, S.K., et al., "Peripheral Education of the Immune System by Colonic Commensal Microbiota," Nature, 478(7368):250-254, Nature Publishing Group, United Kingdom (Sep. 2011).

Lau, S.K.P., et al., "Bacteraemia Caused By Anaerotruncus Colihominis and Emended Description of the Species," Clinical Pathology 59(7):748-752, BMJ Pub. Group, United Kingdom (Jul. 2006).

Lawley, T.D., et al., "Targeted Restoration of the Intestinal Microbiota With a Simple, Defined Bacteriotherapy Resolves Relapsing Clostridium Difficile Disease in Mice," PLoS Pathogens 8(10):e1002995, Public Library of Science, United States (Oct. 2012).

Lawson, P.A., "Anaerotruncus," Bergey's Manual of Systematics of Archaea and Bacteria, Bergey's Manual Trust, 2009, pp. 1-4.

Lawson, P.A., et al., "*Anaerotruncus colihominis* Gen. Nov., Sp. Nov., from Human Faeces," International Journal of Systematic and Evolutionary Microbiology 54(Pt 2):413-417, Microbiology Society, United Kingdom (Mar. 2004).

Lee, I.K., and Liu, J.W., "Clinical Characteristics and Risk Factors for Mortality in Morganella Morganii Bacteremia," Journal of Microbiology, Immunology and Infection, 39(4):328-334, Elsevier for the Taiwan Society of Microbiology, United Kingdom (Aug. 2006).

Lee, J.S., et al., "Survival of Freeze-dried Lactobacillus Bulgaricus KFRI 673 in Chitosan-coated Calcium Alginate Microparticles," Journal of Agricultural and Food Chemistry, 52(24):7300-7305, American Chemical Society, United States (Dec. 2004).

Lee, M., et al., "Synthetic Peptidoglycan Motifs for Germination of Bacterial Spores," ChemBioChem, 11(18):2525-2529, Wiley-VCH Verlag, Germany (Dec. 2010).

Lehar, J., et al., "Chemical Combination Effects Predict Connectivity in Biological Systems," Molecular Systems Biology, 3:1-14, Wiley Blackwell, United Kingdom (Feb. 2007).

Lemon, K.P., et al., "Microbiota-targeted Therapies: an Ecological Perspective," Science Translational Medicine, 4(137):137rv5, American Association for the Advancement of Science, United States (Jun. 2012).

Leslie, S.B., et al., "Trehalose and Sucrose Protect Both Membranes and Proteins in Intact Bacteria During Drying," Applied and Environmental Microbiology, 61(10):3592-3597, American Society for Microbiology, United States (Oct. 1995).

Liggins, M., et al., "Progesterone Analogs Influence Germination of Clostridium Sordellii and Clostridium Difficile Spores in Vitro," Journal of Bacteriology, 193(11):2776-2783, American Society for Microbiology, United States (Jun. 2011).

Lindner et al., "Diversification of memory B cells drives the continuous adaptation of secretory antibodies to gut microbiota," Nature Immunology 16(8):880-890 (2015).

Lindsay, J.A., et al., "Protoplast Water Content of Bacterial Spores Determined by Buoyant Density Sedimentation," Journal of Bacteriology, 163(2):735-737, American Society for Microbiology, United States (Aug. 1985).

Liu, C., et al., "Reclassification of Clostridium Coccoides, Ruminococcus Hansenii, Ruminococcus Hydrogenotrophicus, Ruminococcus Luti, Ruminococcus Productus and Ruminococcus Schinkii as *Blautia coccoides* Gen. Nov., Comb. Nov., Blautia Hansenii Comb. Nov., Blautia Hydrogenotrophica Comb. Nov., Blautia Luti Comb. Nov., Blautia Producta Comb. Nov., Blautia Schinkii Comb. Nov. And Description of *Blautia wexlerae* Sp. Nov., Isolated From Human Faeces," International Journal of Systematic and Evolutionary Microbiology 58(Pt 8): 1896-1902, Microbiology Society, United Kingdom (Aug. 2008),.

Liu, K., et al., "RAxML and FastTree: Comparing Two Methods for Large-scale Maximum Likelihood Phylogeny Estimation," PloS One, 6(11):e27731, Public Library of Science, United States (2011).

Livingston, S.J., et al., "New Medium for Selection and Presumptive Identification of the Bacteroides Fragilis Group," Journal of Clinical Microbiology, 7(5):448-453, American Society for Microbiology, United States (May 1978).

Lizuka, M., et al., "Elemental Diet Modulates the Growth of Clostridium Difficile in the Gut Flora," Alimentary Pharmacology & Therapeutics, 20(1):151-157, Wiley-Blackwell, United Kingdom (Jul. 2004).

Li, A.D., et al., "Clinical Features and Bacterial Culture on Stools of Patients with Acute Diarrhea," Chinese Journal of Health Laboratory Technology, 2(6):559-561 (Mar. 2012).

Lodish, H. et al., "Viruses: Structure, Function, and Uses," Molecular Cell Biology, 4lh Edition, 2000, pp. 1-12.

Logan, N.A., "Bacillus and Relatives in Foodborne Illness," Journal of Applied Microbiology, 112(3):417-429, Published for the Society for Applied Bacteriology by Blackwell Science, United Kingdom (Mar. 2012).

Lopetuso, L.R., et al., "Commensal Clostridia: Leading Players in the Maintenance of Gut Homeostasis," Gut Pathogens, 5(1):23, BioMed Central, United Kingdom (Aug. 2013).

Louie, T.J., et al., "Tolevamer, a Novel Nonantibiotic Polymer, Compared With Vancomycin in the Treatment of Mild to Moderately Severe Clostridium Difficile-associated Diarrhea," Clinical Infectious Diseases, 43(4):411-420, Oxford University Press, United States, (Aug. 2006).

Louis, P and Flint, H.J., "Diversity, Metabolism and Microbial Ecology of Butyrate-producing Bacteria From the Human Large Intestine," FEMS Microbiology Letters 294(1):1-8, Oxford University Press, United Kingdom (May 2009).

Lozupone, C and Knight, R., "UniFrac: a New Phylogenetic Method for Comparing Microbial Communities," Applied and Environmental Microbiology 71(12):8228-8235, American Society for Microbiology, United States (Dec. 2005).

Lozupone, C., et al., "Identifying Genomic and Metabolic Features That Can Underlie Early Successional and Opportunistic Lifestyles of Human Gut Symbionts," Genome Research, 22(10):1974-1984, Cold Spring Harbor Laboratory Press, United States (Oct. 2012).

Lozupone et al., "UniFrac—An online tool for comparing microbial community diversity in a phylogenetic context," BMC Bioinformatics 7:371 (2006).

Machine Translation of PCT Specification, PCT Application No. PCT/JP201 0/071746, Filed Dec. 3, 2010, 79 pages.

MacMillan et al., "What predicts high risk acute graft-versus-host disease (GVHD) at onset?: identification of those at highest risk by a novel acute GVHD risk score," Br. J. Haematol 157:732-741 (2012).

Macpherson, A.J and Uhr, T., "Induction of Protective Iga by Intestinal Dendritic Cells Carrying Commensal Bacteria," Science, 303(5664):1662-1665, American Association for the Advancement of Science, United States, (Mar. 2004).

Magurran, "Measuring Biological Diversity," Malden, MA: Blackwell Publishing; 2004.

Maizels, R.M. and Smith, K.A., "Regulatory T Cells in Infection," Advances in Immunology 112:73-136, Academic Press, United states (2011).

Malard et al., "Impact of Cyclosporine—A Concentration on the Incidence of Severe Acute Graft-Versus-Host Disease after Allogeneic Stem Cell Transplantation," Biol. Blood Marrow Transplant 16:28-34 (2010).

Malik, K.A., "A New Freeze-drying Method for the Preservation of Nitrogen-fixing and Other Fragile Bacteria," Journal of Microbiological Methods, 8(5):259-271, Elsevier, Netherlands (Mar. 1988).

Manafi, M. Handbook of Culture Media for Food and Water Microbiology, 3rd Edition, Janet E.L. Corry et al., 2012, pp. 223-260.

Manges, A.R., et al., "Comparative Metagenomic Study of Alterations to the Intestinal Microbiota and Risk of Nosocomial Clostridum Difficile-associated Disease," The Journal of Infectious Diseases, 202(12):1877-1884, Oxford University Press, United States, (Dec. 2010).

Manichanh, C. et al., "Reshaping the Gut Microbiome with Bacterial Transplantation and Antibiotic Intake," Genome Research, 2010, pp. 1411-1419, vol. 20.

Manichanh, C., "Reduced Diversity of Faecal Microbiota in Crohn's Disease Revealed by a Metagenomic Approach," Gut, 55(2):205-211, British Medical Assn, United Kingdom (Feb. 2006).

(56) References Cited

OTHER PUBLICATIONS

Marcus et al., "Deoxycholic acid and the pathogenesis of gall stones," Gut, 29, 522-533, BMJ Publishing Group, United Kingdom (1988).
Marsh, J.W., et al., "Association of Relapse of Clostridium Difficile Disease With Bi/nap1/027," Journal of Clinical Microbiology, 50(12):4078-4082, American Society for Microbiology, United States, (Dec. 2012).
Martin et al., "Increasingly Frequent Diagnosis of Acute Gastrointestinal Graft-versus-Host Disease after Allogeneic Hematopoietic Cell Transplantation," Biol. Blood Marrow Transplant. 10:320-327 (2004).
Maslowski, K.M. et al., "Diet, Gut Microbiota and Immune Responses," Nature Immunology, Jan. 2011, pp. 5-9, vol. 12, No. 1.
Matsuda, K. et al., "Sensitive Quantitative Detection of Commensal Bacteria by rRNA-targeted Reverse Transcription-PCR," Applied and Environmental Microbiology, 73(1):32-39, American Society for Microbiology, United States (Jan. 2007).
Maynard et al., "Reciprocal interactions of the intestinal microbiota and immune system," Nature 489:231-241 (2012).
Mbithi, J.N., et al., "Chemical Disinfection of Hepatitis a Virus on Environmental Surfaces," Applied and Environmental Microbiology, 56(11):3601-3604, American Society for Microbiology, United States (Nov. 1990).
McAuliffe et al., "Genetic Analysis of Two Bile Salt Hydrolase Activities in Lactobacillus acidophilus NCFM," Appl. Environ Microbial., 71(8):4925-4929 (2005).
Mcfarland, L.V., and Elmer, G.W., "Pharmaceutical Probiotics for the Treatment of Anaerobic and Other Infections," Anaerobe, 3(2-3):73-78, Academic Press, United Kingdom (Apr.-Jun. 1997).
Mcfarland, L.V., "Use of Probiotics to Correct Dysbiosis of Normal Microbiota Following Disease or Dismptive Events: a Systematic Review," BMJ Open, 4(8):e005047, BMJ Publishing Group Ltd, United Kingdom (Aug. 2014).
Mcguire, G., et al., "Models of Sequence Evolution for Dna Sequences Containing Gaps," Molecular Biology and Evolution, 18(4):481-490, Oxford University Press, United Kingdom (Apr. 2001).
Mcnulty, N.P., et al., "The Impact of a Consortium of Fermented Milk Strains on the Gut Microbiome of Gnotobiotic Mice and Monozygotic Twins," Science Translational Medicine, 3(106):106ra106, American Association for the Advancement of Science, United States (Oct. 2011).
Mevissen-Verhage, E.A., et al., "Bifidobacterium, Bacteroides, and *Clostridium* Spp. In Fecal Samples From Breast-fed and Bottle-fed Infants With and Without Iron Supplement," Journal of Clinical Microbiology, 25(2):285-289, American Society for Microbiology, United States (Feb. 1987).
Mexican Office Action, Mexican Application No. MX/a/2015/006491, dated Jun. 25, 2018, 8 pages, (with concise explanation of relevance).
Mexican Office Action, Mexican Application No. MX/a/2015/009991, dated Jul. 16, 2018, (with concise explanation of relevance).
Meyers, "Infection in Bone Marrow Transplant Recipients," The American Journal of Medicine 81(Suppl. 1A):27-38 (1986).
Mierau, L., et al., "Industrial-scale Production and Purification of a Heterologous Protein in Lactococcus Lactis Using the Nisin-controlled Gene Expression System Nice: the Case of Lysostaphin," Microbial Cell Factories, 4:15, BioMed Central, United Kingdom (May 2005).
Miller, R.S., and Hoskins, L.C., "Mucin Degradation in Human Colon Ecosystems. Fecal Population Densities of Mucin-degrading Bacteria Estimated by a "Most Probable Number" Method," Gastroenterology, 81(4):759-765, W.B. Saunders, United States (Oct. 1981).
Miyamoto-Shinohara, Y., et al., "Survival of Freeze-dried Bacteria," The Journal of General and Applied Microbiology, 54(1):9-24, Microbiology Research Foundation, Japan (Feb. 2008).

Momose, Y., et al., "16S rRNA Gene Sequence-based Analysis of Clostridia Related to Conversion of Germfree Mice to the Normal State," Journal of Applied Microbiology 107(6):2088-2097, Blackwell Science, United Kingdom (Dec. 2009).
Morgan, C.A., et al., "Preservation of Micro-organisms by Drying; a Review," Journal of Microbiological Methods, 66(2):183-193, Elsevier Biomedical, Netherlands (Aug. 2006).
Morris, G.N., et al., "*Clostridium scindens* sp. nov., A Human Intestinal Bacterium with Desmolytic Activity on Corticoids," International Journal of Systematic and Evolutionary Microbiology 35(4):478-481, (Oct. 1985).
Mulligan, R.C., "The Basic Science of Gene Therapy," Science 260(5110):926-932, American Association for the Advancement of Science, United States (1993).
Murri, M., et al., "Gut Microbiota in Children With Type 1 Diabetes Differs From That in Healthy Children: a Case-control Study," BMC Medicine, 11:46, BioMed Central, United Kingdom (Feb. 2013).
Myllyluoma, E., et al., "Effects of Multispecies Probiotic Combination on Helicobacter Pylori Infection in Vitro," Clinical and Vaccine Immunology, 15(9):1472-1482, American Society for Microbiology, United States (Sep. 2008).
Naaber, P., et al., "Inhibition of Clostridium Difficile Strains by Intestinal *Lactobacillus* Species," Journal of Medical Microbiology, 53(Pt 6):551-554, Microbiology Society, United Kingdom (Jun. 2004).
Narushima, S., et al., "Characterization of the 17 Strains of Regulatory T Cell-Inducing Human-Derived Clostridia," Gut Microbes 5(3):333-339, Taylor & Francis, United States (May-Jun. 2014).
New Zealand Examination Report, New Zealand Application No. 713298, dated Sep. 26, 2017, 5 pages.
New Zealand First Examination Report, New Zealand Application No. 709392, dated Oct. 5, 2015, 7 pages.
New Zealand First Examination Report, New Zealand Application No. 711771, dated Nov. 23, 2015, 6 pages.
New Zealand First Examination Report, New Zealand Application No. 711773, dated Nov. 24, 2015, 6 pages.
New Zealand First Examination Report, New Zealand Application No. 713298, dated Feb. 28, 2017,6 pages.
New Zealand Fourth Examination Report, New Zealand Application No. 713298, dated Mar. 15, 2018, 2 pages.
New Zealand Second Examination Report, New Zealand Application No. 709392, dated Jun. 9, 2016, 7 pages.
New Zealand Third Examination Report, New Zealand Application No. 711771, dated Nov. 4, 2016, 4 pages.
New Zealand Third Examination Report, New Zealand Application No. 713298, dated Feb. 15, 2018, 6 pages.
Nicholson, W.L., and Law, J.F., "Method for Purification of Bacterial Endospores From Soils: Uv Resistance of Natural Sonoran Desert Soil Populations of *Bacillus* Spp. With Reference to B. Subtilis Strain 168," Journal of Microbiological Methods, 35(1):13-21, Elsevier Biomedical, Netherlands (Feb. 1999).
NIH human microbiome project, (http://www.hmpdacc.org/); Accessed Mar. 27, 2014.
Nishio, J., Atarashi, K., Tanoue, T., Baba, M., Negishi, H., Yanai, H., Honda, K., Benoist, C., Mathis, D., and Taniguchi, T. (2013). Impact of TCR repetoire on intestinal homeostasis (Taos, NM).
Nitert, M.D., et al., "Spring: an Rct Study of Probiotics in the Prevention of Gestational Diabetes Mellitus in Overweight and Obese Women," Bmc Pregnancy and Childbirth, 13:50, BioMed Central, United Kingdom (Feb. 2013).
Nitzan, O., et al., "Role of Antibiotics for Treatment of Inflammatory Bowel Disease," World Journal of Gastroenterology, 22(3):1078-1087, Baishideng Publishing Group, United States (Jan. 2016).
Noack, J., et al., "Dietary Guar Gum and Pectin Stimulate Intestinal Microbial Polyamine Synthesis in Rats," The Journal of Nutrition, 128(8):1385-1391, American Society for Nutrition, United States (Aug. 1998).
Non Final Office Action dated Apr. 7, 2020, in U.S. Appl. No. 16/054,864, Gregory McKenzie et al., filed Aug. 3, 2018, 15 pages.
Non Final Office Action dated Mar. 15, 2019, in U.S. Appl. No. 16/054,864, Gregory McKenzie et al., filed Aug. 3, 2018, 9 pages.

(56) References Cited

OTHER PUBLICATIONS

Non Final Office Action dated Nov. 3, 2016, in U.S. Appl. No. 14/777,252, Henn, M.R., et al., filed Sep. 15, 2015.
Non Final Office Action dated Jan. 23, 2017, in U.S. Appl. No. 14/765,810, Maltzahn, G.V., et al., filed Aug. 4, 2015.
Non Final Office Action dated Aug. 29, 2017, in U.S. Appl. No. 14/777,252, Henn, M.R., et al., filed Sep. 15, 2015.
Non Final Office Action dated Apr. 17, 2018, in U.S. Appl. No. 14/765,814, 14 pages.
Non final Office action dated Mar. 21, 2019, in U.S. Appl. No. 14/765,812, Afey An; N. et al., filed Aug. 4, 2015, 10 pages.
Non Final Office Action dated Mar. 23, 2017, in U.S. Appl. No. 14/776,676, 8 pages.
Non Final Office Action dated Nov. 1, 2017, in U.S. Appl. No. 15/039,007, 12 pages.
Non final Office action dated Nov. 14, 2019, in U.S. Appl. No. 14/765,814, Cook; D. et al., filed Aug. 4, 2015, 17 pages.
Non Final Office Action dated Oct. 17, 2017, in U.S. Appl. No. 15/104,873, 6 pages.
Non Final Office Action dated Oct. 22, 2019, in U.S. Appl. No. 15/742,732, Cook, D. et al., filed Jan. 8, 2018, 10 pages.
Non-Final Office Action dated Oct. 29, 2019, in U.S. Appl. No. 15/990,539, Henn,M.R. et al., filed May 25, 2018, 25 pages.
Non-final Office Action dated Jul. 22, 2014, in U.S. Appl. No. 14/221,190, Henn, M.R., et al., filed Mar. 20, 2014.
Non-final Office Action dated Aug. 25, 2016, in U.S. Appl. No. 14/765,812, Afeyan, N.B., et al., filed Aug. 4, 2015.
Non-final Office Action dated Mar. 25, 2014, in U.S. Appl. No. 14/091,201, Henn, M.R., et al., filed Nov. 26, 2013.
Non-final Office Action dated Apr. 28, 2016, in U.S. Appl. No. 15/068,438, Mckenzie, G., et al., filed Mar. 11, 2016.
Non-final Office Action dated Aug. 17, 2016, in U.S. Appl. No. 14/884,655, Mckenzie, G., et al., filed Oct. 15, 2015.
Non-Final Office action dated Dec. 31, 2019, in U.S. Appl. No. 16/051,747, Maltzahn, G.V. et al., filed Aug. 1, 2018, 46 pages.
Non-Final Office Action dated Mar. 10, 2020, in U.S. Appl. No. 15/778,095, Button, J. et al., filed May 22, 2018, 28 pages.
Non-Final Office Action dated Mar. 23, 2020, in U.S. Appl. No. 15/990,539, Henn,M.R. et al., filed May 25, 2018, 10 pages.
Non-final Office Action dated May 5, 2016, in U.S. Appl. No. 14/884,655, Mckenzie, G., et al., filed Oct. 15, 2015.
Non-Patent Literature Submitted with Notice of Opposition to a European Patent, Jul. 18, 2017, European Patent No. EP2575835: Other Evidence, E102635, 1 page.
Nyangale, E.P., et al., "Gut Microbial Activity, Implications for Health and Disease: the Potential Role of Metabolite Analysis," Journal of Proteome Research, 11(12):5573-5585, American Chemical Society, United States (Dec. 2012).
Office Action dated Dec. 10, 2014, in U.S. Appl. No. 14/313,828, Mckenzie, G., et al., filed Jun. 24, 2014.
Office Action dated Aug. 13, 2014, in U.S. Appl. No. 14/197,044, Mckenzie, G., et al., filed Mar. 4, 2014.
Office Action dated Aug. 13, 2014, in U.S. Appl. No. 14/313,828, Mckenzie, G., et al., filed Jun. 24, 2014.
Office Action dated May 15, 2015, in U.S. Appl. No. 14/313,828, Mckenzie, G., et al., filed Jun. 24, 2014.
Office Action dated Aug. 19, 2016, in U.S. Appl. No. 14/592,481, Henn, M.R., et al., filed Jan. 8, 2015.
Office Action dated Dec. 22, 2015, in U.S. Appl. No. 14/592,481, Henn, M.R., et al., filed Jan. 8, 2015.
Office Action dated Feb. 25, 2014, in European Patent Application No. 11728077.6 filed Jun. 3, 2011.
Office Action dated Feb. 26, 2019, in U.S. Appl. No. 15/312,610, Pamer, E. et al., filed Nov. 18, 2016, 22 pages.
Office Action dated Jul. 10, 2018, in U.S. Appl. No. 15/312,610, Pamer,E. et al., filed Nov. 18, 2016, 16 pages.
Office action dated Oct. 22, 2019, in U.S. Appl. No. 15/742,732, Cook; D. et al., filed Jan. 8, 2018, 10 pages.
Office Action dated Sep. 18, 2015, in European Patent Application No. 11728077.6 filed Jun. 3, 2011.

O'Garra, A., et al., "IL-10-producing and Naturally Occurring CD4+ Tregs: Limiting Collateral Damage," The Journal of Clinical Investigation 114(10):1372-1378, American Society for Clinical Investigation, United states (Nov. 2004).
O'Hara, C.M., et al., "Classification, Identification, and Clinical Significance of Proteus, Providencia, and Morganella," Clinical Microbiology Reviews, 13(4):534-546, American Society for Microbiology, United States (Oct. 2000).
Okada, Y., et al., "Effects of Fecal Microorganisms and Their Chloroform-resistant Variants Derived From Mice, Rats, and Humans on Immunological and Physiological Characteristics of the Intestines of Ex-germfree Mice," Infection and Immunity, 62(12):5442-5446, American Society for Microbiology, United States (Dec. 1994).
Olle, B., "Medicines From Microbiota," Nature Biotechnology, 31(4):309-315, Nature America Publishing, United States (Apr. 2013).
Olszak, T., et al., "Microbial Exposure During Early Life Has Persistent Effects on Natural Killer T Cell Function," Science (New York, N.Y.), 336(6080):489-493, American Association for the Advancement of Science, United States, (Apr. 2012).
OpenBiome. Quality metrics. (http://static.squarespace.com/static/50e0c29ae4b0a05702af7e6a/t/52e19b89e4b0b28f802c9b4e/1390517129976/OpenBiome%20Quality%20Metrics.pdf) Accessed Mar. 21, 2014.
Ott, S.J., et al., "Quantification of Intestinal Bacterial Populations by Real-time Pcr With a Universal Primer Set and Minor Groove Binder Probes: a Global Approach to the Enteric Flora," Journal of Clinical Microbiology, 42(6):2566-2572, American Society for Microbiology,United States, (Jun. 2004).
Out, C., et al., "Bile Acid Sequestrants: More Than Simple Resins," Current opinion in lipidology, 23(1):43-55, Lippincott Williams & Wilkins, United Kingdom (Feb. 2012).
Owens, C., et al., "Fecal Microbiota Transplantation and Donor Standardization," Trends In Microbiology, 21(9):443-445, Elsevier Trends Journals, United Kingdom (Sep. 2013).
Paine, R.T., "A Note on Trophic Complexity and Community Stability," American Naturalist, 102(929):91-93, The University of Chicago Press for The American Society of Naturalists, United States (Jan.-Feb. 1969).
Palmfeldt, J., and Hahn-Hägerdal, B., "Influence of Culture pH on Survival of Lactobacillus Reuteri Subjected to Freeze-drying," International Journal of Food Microbiology, 55(1-3):235-238, Elsevier Science Publishers, Netherlands (Apr. 2000).
Pamer, E.G., "Fecal Microbiota Transplantation: Effectiveness, Complexities, and Lingering Concerns," Mucosal Immunology, 7(2):210-214, Nature Publishing Group, United States (Mar. 2014).
Papadimitriou, K. et al., "Discovering Probiotic Microorganisms: in Vitro, in Vivo, Genetic and Omics Approaches," Frontiers In Microbiology, 6:58, Frontiers Research Foundation, Switzerland (Feb. 2015).
Paredes-Sabja, D., et al., "Inorganic Phosphate and Sodium Ions Are Cogerminants for Spores of Clostridium perfringens Type A Food Poisoning-Related Isolates," Applied and Environmental Microbiology, 75(19):6299-6305, American Society for Microbiology, United States (Oct. 2009).
Parham et al., "A Receptor for the Heterodimeric Cytokine IL-23 is Composed of IL-12R~1 and a Novel Cytokine Receptor Subunit, IL-23R1," J Immunol 168:5699-5708—2002.
Park et al., "*Blautia faecis* sp. nov., isolated from human faeces," Int J Syst Evol Microbial. 63:599-603 (2013).
Partial Supplementary European Search Report dated Jan. 4, 2018 in Application No. 15796000.6.
Passweg et al., "Influence of protective isolation on outcome of allogeneic bone marrow transplantation for leukemia," Bone Marrow Transplantation 21:1231-1238 (1998).
Path Vaccine and Pharmaceutical Technologies Group. Summary of stability data for investigational formulations of vaccines. (http://www.path.org/publications/files/TS_vaccine_stability_table_invest.pdf) Accessed Mar. 21, 2014.
PCT Invitation To Pay Additional Fees, PCT Application No. PCT/US13/71758, dated Feb. 25, 2014, 4 pages.

(56) References Cited

OTHER PUBLICATIONS

PCT Invitation to Pay Additional Fees, PCT Application No. PCT/US14/14745, dated May 16, 2014, 2 pages.
PCT Invitation To Pay Additional Fees, PCT Application No. PCT/US14/29539, dated Jul. 31, 2014, 3 pages.
PCT Invitation To Pay Additional Fees, PCT Application No. PCT/US14/70684, dated Mar. 24, 2015, 2 pages.
PCT Invitation To Pay Additional Fees, PCT Application No. PCT/US2014/014738, dated May 16, 2014, 2 pages.
PCT Invitation To Pay Additional Fees, PCT Application No. PCT/US2014/030817, dated Sep. 8, 2014, 5 pages.
Peck, M.W. et al., "Development and Application of a New Method for Specific and Sensitive Enumeration of Spores of Nonproteolytic Clostridium Botulinum Types B, E, and F in Foods and Food Materials," Applied and Environmental Microbiology, 76(19):6607-6614, American Society for Microbiology, United States (Oct. 2010).
Pehkonen, K.S., et al., "State Transitions and Physicochemical Aspects of Cryoprotection and Stabilization in Freeze-drying of Lactobacillus Rhamnosus GG (LGG)," Journal of Applied Microbiology, 104(6):1732-1743, Society for Applied Bacteriology by Blackwell Science, United Kingdom (Jun. 2008).
Peighambardoust, S.H., et al., "Application of Spray Drying for Preservation of Lactic Acid Starter Cultures: a Review," Trends in Food Science & Technology, 22(5):215-224, Elsevier Ltd, Netherlands (May 2011).
Pelaseyed et al., "The mucus and mucins of the goblet cells and enterocytes provide the first defense line of the gastrointestinal tract and interact with the immune system," Immunological Reviews 260:8-20 (2014).
Pellegrino, P.M., et al., "Enhanced Spore Detection Using Dipicolinate Extraction Techniques," Analytica Chimica Acta, 455(2):167-177, Elsevier Ltd, Netherlands (Mar. 2002).
Perez, F., et al., "Effect of Antibiotic Treatment on Establishment and Elimination of Intestinal Colonization by Kpc-producing Klebsiella Pneumoniae in Mice," Antimicrobial Agents and Chemotherapy, 55(6):2585-2589, American Society for Microbiology, United States (Jun. 2011).
Perez, J., et al., "Clospore: a Liquid Medium for Producing High Titers of Semi-purified Spores of Clostridium Difficile," Journal of AOAC International, 94(2):618-626, AOAC International, United States (Mar.-Apr. 2011).
Petersen, F. B., et al., "Infectious Complications m Patients Undergoing Marrow Transplantation: A Prospective Randomized Study of the Additional Effect of Decontamination and Laminar Airflow Isolation among Patients Receiving Prophylactic Systemic Antibiotics," Scand J. Infect Dis. 19(5):559-567 (1987).
Peterson, D.A. et al., "Metagenomic Approaches for Defining the Pathogenesis of Inflammatory Bowel Diseases," Cell Host & Microbe, 3(6):417-427, Cell Press, United States (Jun. 2008).
Petrof, E.O., et al., "Microbial Ecosystems Therapeutics: a New Paradigm in Medicine?," Beneficial Microbes, 4(1):53-65, Wageningen Academic Publishers, Netherlands (Mar. 2013).
Petrof, E.O., et al., "Stool Substitute Transplant Therapy for the Eradication of Clostridium Difficile Infection: 'Repoopulating' the Gut," Microbiome 1(1):3, BioMed Central, United Kingdom (Jan. 2013).
Pharmacy, 2011, pp. 79-86, vol. 62, No. 3. [With English Main Sub-Points].
Picot, A., and Lacroix, C., "Encapsulation of Bifidobacteria in Whey Protein-based Microcapsules and Survival in Simulated Gastrointestinal Conditions and in Yoghurt," International Dairy Journal, 14(6):505-515, Elsevier Ltd, Netherlands (Jun. 2004).
Pillai, A. et al., "Probiotics for Treatment of Clostridium Difficile-Associated Colitis in Adults (Review)," Cochrane Database of Systematic Reviews, The Cochrane Collaboration, John Wiley & Sons, Ltd., 2010, 18 pages.
Pinn, D. et al. (2013). Follow-up Study of Fecal Microbiota Transplantation (FMT) for the Treatment of Refractory Irritable Bowel Syndrome (IBS). Abstract ACG 2013.

Plassart, C., et al., "First Case of Intra-abdominal Infection With Clostridium Disporicum," Anaerobe, 19:77-78, Academic Press, United Kingdom (Feb. 2013).
Ponce et al., "Graft-versus-Host Disease after Double-Unit Cord Blood Transplantation Has Unique Features and an Association with Engrafting Unit-To-Recipient HLA Match," Biol. Blood Marrow Transplant 19:904-911 (2013).
Postgate, Jr., and Hunter, J.R., "On the Survival of Frozen Bacteria," Journal of General Microbiology, 26:367-378, Society for General Microbiology, United Kingdom (Nov. 1961).
Potentials of Probiotics in Pig Nutrition, AllAboutFeed News, Jan. 31, 2007, 6 pages.
Prilassnig, M. et al., "Are Probiotics Detectable in Human Feces After Oral Uptake by Healthy Volunteers?," Wiener Klinische Wochenschrift, 119(15-16):456-462, Springer, Austria (Aug. 2007).
Priority Document JP 2010-129134 for PCT Application No. PCT/JP2011/063302, Filed Jun. 4, 2010, 42 pages.
Priority Document PCT/JP2010/071746 for PCT Application No. PCT/JP2011/063302, Filed Dec. 3, 2010, 107 pages.
Prioul T, G. et al., "Effect of Probiotic Bacteria on Induction and Maintenance of Oral Tolerance to β-Lactoglobulin in Gnotobiotic Mice," Clinical and Vaccine Immunology, 10(5):787-792, American Society for Microbiology, United States (Sep. 2003).
Pultz, N.J., et al., "Inhibition of Methicillin-resistant *Staphylococcus aureus* by an in Vitro Continuous-flow Culture Containing Human Stool Microflora," FEMS Microbiology Letters, 241(2):201-205, Oxford Oxford University Press, United Kingdom (Dec. 2004).
Qiu, X., et al., "Faecalibacterium prausnitzii Upregulates Regulatory T Cells and Anti-Inflammatory Cytokines In Treating TNBS-Induced Colitis," Crohn's and Colitis 7(11):e558-e568, Elsevier Science, United Kingdom (Dec. 2013 ).
Queenan, A.M., and Bush, K., "Carbapenemases: the Versatile Beta-lactamases," Clinical Microbiology Reviews, 20(3):440-458, American Society for Microbiology, United States (Jul. 2007).
Quigley, E.M., and Quera, R., "Small Intestinal Bacterial Overgrowth: Roles of Antibiotics, Prebiotics, and Probiotics," Gastroenterology, 130(2 Suppl 1):S78-S90, W.B. Saunders, United States (Feb. 2006).
Raibaud, P., et al., "Implantation of Bacteria From the Digestive Tract of Man and Various Animals Into Gnotobiotic Mice," The American Journal of Clinical Nutrition, 33(11 Suppl):2440-2447, American Society of Clinical Nutrition, United States (Nov. 1980).
Rakoff-Nahoum, S., et al., "Recognition of Commensal Microflora by Toll-like Receptors is Required for Intestinal Homeostasis," Cell, 118(2):229-241, Cell Press, United States, (Jul. 2004).
Ramirez, N., and Abel-Santos, E., "Requirements for Germination of Clostridium sordellii Spores In Vitro," Journal of Bacteriology, 192(2):418-425, American Society for Microbiology, United States (Jan. 2010).
Rao, A.V., et al., "Survival of Microencapsulated Bifidobacterium Pseudolongum in Simulated Gastric and Intestinal Juices," Canadian Institute of Food Science and Technology Journal, 22(4):345-349, Elsevier Ltd, Netherlands (Oct. 1989).
Rasti et al., "Inhibition of Clostridium scindens and Clostridium hiranonis growth by Bifidobacterium pseudocatenulatum G4 in simulated colonic pH," Journal of Food Agriculture and Environment 11 (2): 127-131, WFL Publisher Ltd, Poland (2013).
Rea, M.C., et al., "Effect of Broad- and Narrow-spectrum Antimicrobials on Clostridium Dif.ficile and Microbial Diversity in a Model of the Distal Colon," Proceedings of the National Academy of Sciences of the United States of America, 108 Suppl 1:4639-4644, National Academy of Sciences, United States, (Mar. 2011).
Rea, M.C.,et al., "Thuricin Cd, a Posttranslationally Modified Bacteriocin With a Narrow Spectrum of Activity Against Clostridium Dif.ficile," Proceedings of the National Academy of Sciences of the United States of America, 107(20):9352-9357, National Academy of Sciences, (May 2010).
Reeves, A.E., et al., "Suppression of Clostridium Difficile in the Gastrointestinal Tracts of Germfree Mice Inoculated With a Murine Isolate From the Family Lachnospiraceae," Infection and Immunity, 80(11):3786-3794, American Society for Microbiology, United States (Nov. 2012).

(56) References Cited

OTHER PUBLICATIONS

Reeves, A.E., et al., "The Interplay Between Microbiome Dynamics and Pathogen Dynamics in a Murine Model of Clostridium Difficile Infection.," Gut Microbes, 2(3):145-158, Philadelphia, PA : Taylor & Francis, (May 2011).

Rehman, A. et al., "Effects of Probiotics and Antibiotics on the Intestinal Homeostasis in a Computer Controlled Model of the Large Intestine," BMC Microbiology, 12:47, BioMed Central, United Kingdom (Mar. 2012).

Response of Jan. 28, 2015 in Examination, European Application No. 11728077.6, 3 pages.

Response to Official Communication dated Sep. 18, 2018, European Application No. 11728077.6, filed Nov. 18, 2015, 2 pages.

Rexroad, J., et al., "Lyophilization and the Thermostability of Vaccines," Cell Preservation Technology, 1(2):91-104, Mary Ann Liebert, Inc, United States (Jun. 2002).

Ridaura, V.K., et al., "Gut Microbiota From Twins Discordant for Obesity Modulate Adiposity and Metabolic Phenotypes in Mice," Science, 341(6150):1241214, American Association for the Advancement of Science, United States (Sep. 2013).

Ridlon, J.M and Hylemon, P.B., "Identification and Characterization of Two Bile Acid Coenzyme a Transferases From Clostridium Scindens, a Bile Acid 7α-dehydroxylating Intestinal Bacterium.," Journal of Lipid Research, 53(1):66-76, American Society for Biochemistry and Molecular Biology, United States, (Jan. 2012).

Ridlon, J.M., "Enzymology and Molecular Biology of Bile Acid 7alpha- And 7beta-Dehydroxylation By The Intestinal Bacteria Clostridium Scindens And Clostridium Hylemonae," VCU Theses and Dissertations, Paper 736 (2008).

Ridlon, J.M., et al., "Clostridium Scindens: a Human Gut Microbe With a High Potential to Convert Glucocorticoids Into Androgens.," Journal of Lipid Research, 54(9):2437-2449, American Society for Biochemistry and Molecular Biology, United States, (Sep. 2013).

Ridlon,J.M.,et al, "Bile Salt Biotransformations by Human Intestinal Bacteria.," Journal of Lipid Research, 47(2):241-259, American Society for Biochemistry and Molecular Biology, (Feb. 2006).

Roberts, B., "Generation and Development of Defined Microbial Drug Products," Vedanta Biosciences, 17 pages (2016).

Robinson, I.M. et al., "Emendation of Acetivibrio and Description of Acetivibrio Ethanolgignens, a New Species From the Colons of Pigs With Dysentery," International Journal of Systematic Bacteriology , 31(3):333-338 (Jul. 1981).

Rode, L.J., and Foster, J.W., "Germination of Bacterial Spores With Alkyl Primary Amines1," Journal of Bacteriology, 81(5):768-779, American Society for Microbiology, United States (May 1961).

Roffe, C., "Biotherapy for Antibiotic-associated and Other Diarrhoeas," The Journal of infection, 32(1):1-10, W.B. Saunders, United Kingdom (Jan. 1996).

Rohleke, F., et al., "Fecal Flora Reconstitution for Recurrent Clostridium Difficile Infection: Results and Methodology," Journal of Clinical Gastroenterology, 44(8):567-570, Wolters Kluwer Health, Inc, United States (Sep. 2010).

Rosen, D.L., et al., "Bacterial Spore Detection and Determination by Use of Terbium Dipicolinate Photoluminescence," Analytical Chemistry, 69(6):1082-1085, American Chemical Society, United States (1997).

Rosero, J.A., et al., "Reclassification of Eubacterium Rectale (Hauduroy et al. 1937) Prévot 1938 in a New Genus *Agathobacter* Gen. Nov. As Agathobacter Rectalis Comb. Nov., and Description of *Agathobacter ruminis* Sp. Nov., Isolated From the Rumen Contents of Sheep and Cows," International Journal of Systematic and Evolutionary Microbiology, 66(2):768-773, Microbiology Society, United Kingdom (Feb. 2016).

Rossen, N.G., et al., "Findings From a Randomized Controlled Trial of Fecal Transplantation for Patients With Ulcerative Colitis.," Gastroenterology, 149(1):110-118, W.B. Saunders, United States (Jul. 2015).

Rossi, O., et al., "Faecalibacterium Prausnitzii A2-165 has a High Capacity to Induce IL-10 in Human and Murine Dendritic Cells and Modulates T Cell Responses," Scientific Reports 6:12 pages, (Jan. 2015).

Rowlings, P. A., et al., "IBMTR Severity Index for grading acute graft-versus-host disease: retrospective comparison with Glucksberg grade," Br J Haematol. 97:855-864 (1997).

Rupnik, M., et al., "Clostridium Difficile Infection: New Developments in Epidemiology and Pathogenesis.," Nature Reviews. Microbiology, 7(7):526-536, Nature Pub. Group, c2003-,United Kingdom (Jul. 2009).

Russell, A.D., "The Destruction of Bacterial Spores," 1982, pp. 191-193.

Russell et al., "Early Outcomes After Allogeneic Stem Cell Transplantation for Leukemia and Myelodysplasia Without Protective Isolation: A 1 0-year Experience," Biol. Blood Marrow Transplant 6(2): 109-114 (2000).

Russian First Office Action, Russian Patent Application No. 2015124366, dated Dec. 13, 2016, 12 pages.

Russian Office Action, Russian Application No. 2015137399, dated Mar. 22, 2016, 8 pages.

Russian Office Action, Russian Application No. 201537399, dated Aug. 15, 2016, 8 pages.

Russian Second Office Action, Russian Application No. 2015124366, dated Feb. 12, 2018, 10 pages.

Russian Second Office Action, Russian Patent Application No. 2015137399, dated Mar. 14, 2017, 8 pages.

Sack, D.A., et al., "Comparison of Alternative Buffers for Use With a New Live Oral Cholera Vaccine, Peru-15, in Outpatient Volunteers," Infection and Immunity, 65(6):2107-2111, American Society for Microbiology, United States (Jun. 1997).

Sacks, L.E. and Alderton, G., "Behavior of Bacterial Spores in Aqueous Polymer Two-phase Systems," Journal of Bacteriology, 82(3):331-341, American Society for Microbiology, United States (Sep. 1961).

Sahlstrom, L., et al., "A Laboratory Study of Survival of Selected Microorganisms After Heat Treatment of Biowaste Used in Biogas Plants," Bioresource Technology, 99(16):7859-7865, Elsevier Science Pub. Co., United Kingdom (Nov. 2008).

Salzman et al., "Analysis of 16S libraries of mouse gastrointestinal microflora reveals a large new group of mouse intestinal bacteria," Microbiology 148:3651-3660 (2002).

Sanchez, A.M. and Yang, Y., "The Role of Natural Regulatory T Cells in Infection," Immunologic Research 49(1-3):124-134, Humana Press, United states (Apr. 2011).

Santivarangkna, C., et al., "Alternative Drying Processes for the Industrial Preservation of Lactic Acid Starter Cultures," Biotechnology Progress, 23(2):302-315, Wiley-Blackwell, United States (Mar.-Apr. 2007).

Sartor, R.B., "Therapeutic Correction of Bacterial Dysbiosis Discovered by Molecular Techniques," Proceedings of the National Academy of Sciences of the United States of America 105(43):16413-16414, National Academy of Sciences, United states (Oct. 2008).

Sattar, S.A., et al., "Foodborne Spread of Hepatitis a: Recent Studies on Vims Survival, Transfer and Inactivation," The Canadian Journal of Infectious Diseases, 11(3):159-163, Pulsus Group, Inc., Canada (May-Jun. 2000).

Savaiano, D.A., et al., "1040 A Novel High Purity Short-Chain Galacto-Oligosaccharide (RP-G28) Improves Lactose Digestion and Symptoms of Lactose Intolerance," Gastroenterology, 142(5 Supp 1):S-182, Elsevier Inc, Netherlands (May 2012).

Savaiano, D.A., et al., "Improving Lactose Digestion and Symptoms of Lactose Intolerance With a Novel Galacto-oligosaccharide (Rp-g28): a Randomized, Double-blind Clinical Trial," Nutrition Journal, 12:160, BioMed Central, United Kingdom (Dec. 2013).

Schloss, P.D., et al., "IntroducingMothur: Open-source, Platform-independent, Community-supported Software for Describing and Comparing Microbial Communities," Applied and Environmental Microbiology 75(23):7537-7541, American Society for Microbiology, United States (Dec. 2009).

Schloss, P.D., et al., "Reducing the Effects of Per Amplification and Sequencing Artifacts on 16s Rrna-based Studies," PLoS One 6(12):e27310, Public Library of Science, United States (Dec. 2011).

(56) References Cited

OTHER PUBLICATIONS

Schoefer, L., et al., "Anaerobic degradation of flavonoids by Clostridium orbiscindens," Appl Environ Microbiol 69(10):5849-5854, American Society of Microbiology, United States (Oct. 2003).
Seale, R.B., et al., "Recovery of Spores From Thermophilic Dairy Bacilli and Effects of Their Surface Characteristics on Attachment to Different Surfaces," Applied and Environmental Microbiology, 74(3):731-737, American Society for Microbiology, United States (Feb. 2008).
Seki, H., et al., "Prevention of Antibiotic-Associated Diarrhea in Children by Clostridium Butyricum Miyairi," Pediatrics International, 45(1):86-90, Blackwell Science Asia, Australia (Feb. 2003).
Seo, M., et al., "Clostridium Butyricum Miyairi 588 Improves High-fat Diet-induced Non-alcoholic Fatty Liver Disease in Rats," Digestive Diseases and Sciences, 58(12):3534-3544, Springer Science + Business Media, United States (Dec. 2013).
Sequence Listing, PCT Application No. PCT/JP2011/063302, 43 pages, Dec. 8, 2011.
Setlow, B., et al., "Analysis of the Germination Kinetics of Individual Bacillus Subtilis Spores Treated With Hydrogen Peroxide or Sodium Hypochlorite," Letters in Applied Microbiology, 57(4):259-265, Published for the Society for Applied Bacteriology by Blackwell Scientific Publications, United Kingdom (Oct. 2013).
Setlow, B., et al., "Germination of Spores of Bacillus Subtilis With Dodecylamine," Journal of Applied Microbiology, 95(3):637-648, Oxford : Published for the Society for Applied Bacteriology by Blackwell Science, United Kingdom (2003).
Setlow, B., et al., "Mechanisms of Killing Spores of Bacillus Subtilis by Acid, Alkali and Ethanol," Journal of Applied Microbiology, 92(2):362-375, Published for the Society for Applied Bacteriology by Blackwell Science, United Kingdom (2002).
Sghir, A., et al., "Quantification of Bacterial Groups Within Human Fecal Flora by Oligonucleotide Probe Hybridization," Applied and Environmental Microbiology 66(5):2263-2266, American Society for Microbiology, United States (May 2000).
Shafaat, H.S., and Ponce, A., "Applications of a Rapid Endospore Viability Assay for Monitoring UV Inactivation and Characterizing Arctic Ice Cores," Applied and Environmental Microbiology, 72(10):6808-6814, American Society for Microbiology, United States (Oct. 2006).
Shah, I.M., et al., "A Eukaryotic-like Ser/Thr Kinase Signals Bacteria to Exit Dormancy in Response to Peptidoglycan Fragments," Cell, 135(3):486-496, Cell Press, United States (Oct. 2008).
Shah, N.P. et al., "Microencapsulation of Probiotic Bacteria and Their Survival in Frozen Fermented Dairy Desserts," The Australian Journal of Dairy Technology, Oct. 2000, pp. 139-144, vol. 55, No. 3.
Shah, N.P., "Symposium: Probiotic Bacteria: Probiotic Bacteria: Selective Enumeration and Survival in Dairy Foods," Oct. 7, 1999, 14 pages.
Shah, S. (2012). Clostridium difficile in inflammatory Bowel Disease: a dangerous mix (Clostridium difficile Symposium, Miriam Hospital, Providence, RI).
Shahinas, D., et al., "Toward an Understanding of Changes in Diversity Associated With Fecal Microbiome Transplantation Based on 16S rRNA Gene Deep Sequencing," 3(5):e00338-12, American Society for Microbiology, United States (Oct. 2012).
Sharpe, E.S. et al., "Separation of Spores and Parasporal Crystals of Bacillus Thuringiensis in Gradients of Certain X-ray Contrasting Agents," Applied Microbiology, 30(6):1052-1053, American Society for Microbiology, United States (Dec. 1975).
Sheneman, L.,et al., "Clearcut: a Fast Implementation of Relaxed Neighbor Joining.," Bioinformatics (Oxford, England), 22(22):2823-2824, Oxford University Press, c1998, United Kingdom (Nov. 2006).
Sheptulin, A.A., "Refractory and Relapsing Forms of Clostridium difficile-Associated Colitis," www.gastro-j.ru, 2011, pp. 50-53 (with English abstract).

Sheu, T.Y., et al., "Improving Survival of Culture Bacteria in Frozen Desserts by Microentrapment," Journal of Dairy Science, 76(7):1902-1907, American Dairy Science Association, United States (Jul. 1993).
Siaterlis, A., et al., "Effect of Culture Medium and Cryoprotectants on the Growth and Survival of Probiotic Lactobacilli During Freeze Drying," Letters in Applied Microbiology, 48(3):295-301, Published for the Society for Applied Bacteriology by Blackwell Scientific Publications, United Kingdom (Mar. 2009).
Sigma-Tau. VSL#3. http://www.vsl3.com/; Accessed Mar. 21, 2014.
Skaar, E., "The Battle for Iron between Bacterial Pathogens and Their Vertebrate Hosts," PLoS Pathogens, 6(8):e1000949, Public Library of Science, United States (Aug. 2010).
Sleator, R.D., Hill, C., "Designer Probiotics: a Potential Therapeutic for Clostridium Difficile?," Journal of Medical Microbiology, 57(Pt6):793-794, Microbiology Society, United Kingdom (Jun. 2008).
Smith, P.M., et al., "The Microbial Metabolites, Short-Chain Fatty Acids, Regulate Colonic Treg Cell Homeostasis," Science 341(6145):569-573, American Association for the Advancement of Science, United States (Aug. 2013 ).
Snitkin, E.S., et al., "Tracking a Hospital Outbreak of Carbapenem-resistant Klebsiella Pneumoniae With Whole-genome Sequencing," Science Translational Medicine, 4(148):148ra116, American Association for the Advancement of Science, United States (Aug. 2012).
Sokol, H., et al., "Faecalibacterium Prausnitzii Is an Anti-Inflammatory Commensal Bacterium Identified By Gut Microbiota Analysis of Crohn Disease Patients," Proceedings of the National Academy of Sciences 105(43):16731-16736, National Academy of Sciences, United States (Oct. 2008).
Sokol, H., et al., "Low Counts of Faecalibacterium Prausnitzii in Colitis Microbiota," Inflammatory Bowel Diseases 15(8):1183-1189, Lippincott Williams & Wilkins, nited States (Aug. 2009).
Solanki, H.K., et al., "Development of Microencapsulation Delivery System for Long-term Preservation of Probiotics as Biotherapeutics Agent," BioMed Research International, 2013:620719, Hindawi Pub. Co., United States (2013).
Solomkin et al., "Diagnosis and Management of Complicated Intra-abdominal Infection in Adults and Children: Guidelines by the Surgical Infection Society and the Infectious Diseases Society of America," Clin Infect Dis. 50:133-164 (2010).
SOP No. MB-28-00. http://www.epa.gov/pesticides/methods/MB-28-00.pdf; Accessed Mar. 27, 2014.
Sorg, J.A., and Sonenshein, A.L., "Bile Salts and Glycine as Cogerminants for Clostridium Difficile Spores," Journal of Bacteriology, 190(7):2505-2512, American Society for Microbiology, United States (Apr. 2008).
Sorg, J.A. and Sonenshein, A.L., "Chenodeoxycholate is an Inhibitor of Clostridium Difficile Spore Germination.," Journal of Bacteriology, 191(3):1115-1117, American Society for Microbiology,United States, (Feb. 2009).
Sow, H., et al., "Heat Inactivation of Hepatitis a Virus and a Norovirus Surrogate in Soft-shell Clams (*Mya arenaria*)," Foodborne Pathogens and Disease, 8(3):387-393, Mary Ann Liebert, Inc., United States (Mar. 2011).
Stackebrandt, E., et al., "Taxonomic Note: A Place for DNA-DNA Reassociation and 16s rRNA Sequence Analysis in the Present Species Definition in Bacteriology ," International Journal of Systematic Bacteriology 44 (4):846-849, (Oct. 1994).
Stams, A.J.M., et al., "Growth of Syntrophic Propionate-Oxidizing Bacteria with Fumarate in the Absence of Methanogenic Bacteria," Applied and Environmental Microbiology, 59(4):1114-1119, American Society for Microbiology, United States (Apr. 1993).
Stefka, A.T., et al., "Commensal Bacteria Protect Against Food Allergen Sensitization," Proceedings of the National Academy of Sciences of the United States of America, 111(36):13145-13150, National Academy of Sciences, United States (Sep. 2014).
Stein, R.R., et al., "Ecological Modeling From Time-series Inference: Insight Into Dynamics and Stability of Intestinal Microbiota.," Pios Computational Biology, 9(12):1003388, Public Library of Science, [2005], United States , (Sep. 2013).

(56) References Cited

OTHER PUBLICATIONS

Stevens, K.A., and Jaykus, L.A., "Bacterial Separation and Concentration From Complex Sample Matrices: a Review," Critical Reviews in Microbiology, 30(1):7-24, Informa Healthcare, United Kingdom (2004).
Su, W.J., et al., "Role of Volatile Fatty Acids in Colonization Resistance to Clostridium Difficile in Gnotobiotic Mice," Infection and Immunity, 55(7):1686-1691, American Society for Microbiology, United States (Jul. 1987).
Supplementary Partial European Search Report dated Jun. 14, 2018 in Application No. EP 15862844.
Surawicz, C.M. and Alexander, J., "Treatment of Refractory and Recurrent Clostridium Difficile Infection," Nature Reviews Gastroenterology & Hepatology, 8(6):330-339, Nature Publishing Group, United Kingdom (Jun. 2011).
Swidsinski et al., "Spatial Organization and Composition of the Mucosal Flora in Patients with Inflammatory Bowel Disease," Journal of Clinical Microbiology 43(7):3380-3389—2005.
Takaishi, H., et al., "Imbalance in Intestinal Microflora Constitution Could Be Involved In the Pathogenesis of Inflammatory Bowel Disease," International Journal of Medical Microbiology 298(5-6):463-572, Urban & Fischer Verlag, Germany (Jul. 2008 ).
Talwalkar, A., and Kailasapathy, K., "Effect of Microencapsulation on Oxygen Toxicity in Probiotic Bacteria," Australian Journal of Dairy Technology, 58(1):36-39, Australian Society of Dairy Technology, Australia (2003).
Tamir, H., and Gilvarg, C., "Density Gradient Centrifugation for the Separation of Sporulating Forms of Bacteria," The Journal of Biological Chemistry, 241(5):1085-1090, American Society for Biochemistry and Molecular Biology, United States (Mar. 1966).
Tanaka, M. et al., "Increased Fasting Plasma Ghrelin Levels in Patients With Bulimia Nervosa," European Journal of Endocrinology, 146(6):R1-3, BioScientifica Ltd, United Kingdom (Jun. 2002).
Taur, Y., and Pamer, E.G., "Harnessing Microbiota to Kill a Pathogen: Fixing the Microbiota to Treat Clostridium Difficile Infections," Nature Medicine, 20(3):246-247, Nature Publishing Company, United States (Mar. 2014).
Taur, Y., et al., "Intestinal Domination and the Risk of Bacteremia in Patients Undergoing Allogeneic Hematopoietic Stem Cell Transplantation," Clinical Infectious Diseases : an Official Publication of the Infectious Diseases Society of America, 55(7):905-914, Oxford University Press, United States (Oct. 2012).
Technical Data, HiMedia Laboratories Pvt. Ltd., M581 BP, 2011, pp. 1-2.
Theriot, C.M. et al., "Antibiotic-induced Shifts in the Mouse Gut Microbiome and Metabolome Increase Susceptibility to Clostridium Difficile Infection," Nature Communications, 5:3114, Nature Publishing Group, United Kingdom (Jan. 2014).
Thompson-Chagoyan, O.C., et al., "Aetiology of Inflammatory Bowel Disease (IBD): Role of Intestinal Microbiota and Gut-associated Lymphoid Tissue Immune Response," Clinical Nutrition, 24(3):339-352, Elsevier, United Kingdom (Feb. 2005).
Tisa, L.S., et al., "Wet and Dry Bacterial Spore Densities Determined by Buoyant Sedimentation," Applied and Environmental Microbiology, 43(6):1307-1310, American Society for Microbiology, United States (Jun. 1982).
Turnbaugh, P.J., et al., "A Core Gut Microbiome in Obese and Lean Twins.," Nature, 457(7228):480-484, Nature Publishing Group, United Kingdom (Jan. 2009).
Tvede, M, and Rask-Madsen, J., "Bacteriotherapy for Chronic Relapsing Clostridium Difficile Diarrhoea in Six Patients," Lancet 1(8648):1156-1160, Elsevier, United Kingdom (May 1989).
Ubeda, C., et al., "Intestinal Microbiota Containing *Barnesiella* Species Cures Vancomycin-resistant Enterococcus Faecium Colonization," Infection and Immunity, 81(3):965-973, American Society for Microbiology, United States (Mar. 2013).
Ubeda, C., et al., "Vancomycin-resistant Enterococcus Domination of Intestinal Microbiota Is Enabled by Antibiotic Treatment in Mice and Precedes Bloodstream Invasion in Humans," The Journal of Clinical Investigation, 120(12):4332-4341, American Society for Clinical Investigation, United States (Dec. 2010).
Van Der Woude, M.W., and Baumler, A.J., "Phase and Antigenic Variation in Bacteria," Clinical Microbiology Reviews, 17(3):581-611, American Society for Microbiology, United States (Jul. 2004).
Van Immerseel, F., et al., "Butyric Acid-Producing Anaerobic Bacteria as a Novel Probiotic Treatment Approach for Inflammatory Bowel Disease," Medical Microbiology 59(Pt 2):141-143, Microbiology Society, United Kingdom (Feb. 2010).
Van Kregien, E., et al., "New, Simple Medium for Selective Recovery of Klebsiella Pneumoniae and Klebsiella Oxytoca From Human Feces," The Journal of Clinical Microbiology, 20(5):936-941, American Society for Microbiology, United States (Nov. 1984).
Van Nood, E., et al., "Duodenal Infusion of Donor Feces for Recurrent Clostridium Difficile," The New United Kingdom Journal of Medicine 368(5):407-415, Massachusetts Medical Society, United States (Jan. 2013).
Vandenplas, Y. et al., "Fecal Microbial Transplantation in Early-onset Colitis: Caution Advised," Journal of Pediatric Gastroenterology and Nutrition, 61(3):e12-4, Lippincott Williams & Wilkins, United States (Sep. 2015).
Vidal, M., et al., "Probiotics and Intestinal Colonization by Vancomycin-resistant Enterococci in Mice and Humans," The Journal of Clinical Microbiology, 48(7):2595-2598, American Society for Microbiology, United States (Jul. 2010).
Villano, S.A., et al., "Evaluation of an Oral Suspension of VP20621, Spores of Nontoxigenic Clostridium Difficile Strain M3, in Healthy Subjects," Antimicrobial Agents and Chemotherapy, 56(10):5224-5229, American Society for Microbiology, United States (Oct. 2012).
Vogt et al. "Chemical communication in the gut: Effects of microbiota-generated metabolites on gastrointestinal bacterial pathogens," Anaerobe 34 106-115, Elsevier, Netherlands (2015).
Wachsman, J.T., et al., "Characterization of an Orotic Acid Fermenting Bacterium, *Zymobacterium oroticum*, Nov. Gen., Nov. Spec," Bacteriology 68(4):400-404, American Society for Microbiology, United States (Oct. 1954).
Wagman, J., and Weneck, E.J., "Preservation of Bacteria by Circulating-gas Freeze Drying," Applied Microbiology, 11:244-248, American Society for Microbiology, United States (May 1963).
Waites, W.M., and Wyatt, L.R., "Germination of Spores of Clostridium Bifermentans by Certain Amino Acids, Lactate and Pyruvate in the Presence of Sodium or Potassium Ions," Journal of General Microbiology, 67(2):215-222, Society for General Microbiology, United Kingdom (Aug. 1971).
Waiies, W.M., and Wyatt, L.R., "The Effect of pH, Germinants and Temperature on the Germination of Spores of Clostridium Bifermentans," Journal of General Microbiology, 80(1):253-258, Society for General Microbiology, United Kingdom (Jan. 1974).
Walker, A.W., and Lawley, T.D., "Therapeutic Modulation of Intestinal Dysbiosis," Pharmacological Research, 69(1):75-86, Elsevier, Netherlands (Mar. 2013).
Wang, M., et al., "Comparison of Bacterial Diversity Along the Human Intestinal Tract by Direct Cloning and Sequencing of 16S rRNA Genes," FEMS Microbiology Ecology, 54(2):219-231, Oxford University Press, United Kingdom (Oct. 2005).
Wang, Q., et al., "Naive Bayesian Classifier for Rapid Assignment of Rrna Sequences Into the New Bacterial Taxonomy," Applied and Environmental Microbiology 73(16):5261-5267, American Society for Microbiology, United States (Aug. 2007).
Wang, S., and Curtiss Ill, R., "Development of Streptococcus Pneumoniae Vaccines Using Live Vectors," Vaccines, 2(1):49-88, MDPI AG, Switzerland (Jan. 2014).
Warren, Y.A., et al., "*Clostridium aldenense* Sp. Nov. and *Clostridium citroniae* Sp. Nov. Isolated from human clinical Infections," Journal of Clinical Microbiology 44(7):2416-2422, American Society for Microbiology, United States (Jul. 2006 ).
Weingarden, A.R., et al., "Microbiota Transplantation Restores Normal Fecal Bile Acid Composition in Recurrent Clostridium Difficile Infection," American Journal of Physiology. Gastrointestinal and Liver Physiology, 306(4):G310-319, American Physiological Society, United States (Feb. 2014).

(56) References Cited

OTHER PUBLICATIONS

Wells, C.L. et al., Chapter 18: Clostridia: Sporeforming Anaerobic Bacilli, Medical Microbiology, 4th Edition, 1996, pp. 1-20.
Wells, J.E and Hylemon, P.B., "Identification and Characterization of a Bile Acid 7alpha-dehydroxylation Operon in *Clostridium* Sp. Strain to-931, a Highly Active 7alpha-dehydroxylating Strain Isolated From Human Feces.," Applied and Environmental Microbiology, 66(3):1107-1113, American Society for Microbiology,United States, (Mar. 2000).
Wells, J.E.,et al., "Development and Application of a Polymerase Chain Reaction Assay for the Detection and Enumeration of Bile Acid 7alpha-dehydroxylating Bacteria in Human Feces.," Clinica chimica acta; international journal of clinical chemistry, 331(1-2):127-134, Elsevier,Netherlands, (May 2003).
Wiencek, K.M. et al., "Hydrophobicity of Bacillus and Clostridium Spores," Applied and Environmental Microbiology, 56(9):2600-2605, American Society for Microbiology, United States (Sep. 1990).
Wilson, K.H and Freter, R, "Interaction of Clostridium Difficile and *Escherichia coli* With Microfloras in Continuous-flow Cultures and Gnotobiotic Mice," Infection and Immunity, 54(2):354-358, American Society For Microbiology, United States (Nov. 1986).
Wilson, K.H., et al., "Role of Competition for Nutrients in Suppression of Clostridium Difficile by the Colonic Microflora," Infection and Immunity, 56(10):2610-2614, American Society for Microbiology, United States (Oct. 1988).
Wilson, K.H., et al., "Suppression of Clostridium difficile by Normal Hamster Cecal Flora and Prevention of Antibiotic-Associated Cecitis," Infection and Immunity, 34(2):626-628, American Society for Microbiology, United States (Nov. 1981).
Wilson, K.H., Sheagren, J.N., "Antagonism of Toxigenic Clostridium Difficile by Nontoxigenic C. Difficile," The Journal of Infectious Diseases, 147(4):733-736, Oxford University Press, United Kingdom (Apr. 1983).
Wingender, G.,et al., "Intestinal Microbes Affect Phenotypes and Functions of Invariant Natural Killer T Cells in Mice," Gastroenterology, 143(2):418-428, PA : W.B. Saunders,United States, (Aug. 2012).
Winter, J., et al., "*Clostridium orbiscindens* Sp. Nov., A Human Intestinal Bacterium Capable of Cleaving the Flavonoid C-Ring," International Journal of Systematic Bacteriology, 41(3):355-357, Society for General Microbiology, United Kingdom (1991).
Woo, T.D., et al., "Inhibition of the Cytotoxic Effect of Clostridium Difficile in Vitro by Clostridium Butyricum Miyairi 588 Strain," Journal of Medical Microbiology, 60(Pt 11):1617-1625, Microbiology Society, United Kingdom (Nov. 2011).
Wood et al., "Kraken: ultrafast metagenomic sequence classification usmg exact alignments," Genome Biology 15:R46 (2014).
Wortman, J. R., et al., "Design and evaluation of SER-262: A fermentation-derived microbiometherapeutic for the prevention of recurrence in patients with primary Clostridium difficile infection," Seres Therapeutics, Cambridge, MA, Jun. 1, 2016, Retrived from (http://serestherapeutics.com/sites/default/files/wortman_asm_poster_final_poster_ser_262.pdf), Retrieved on [Mar. 6, 2017], 1 page.
Wrobel, B., "Statistical Measures of Uncertainty for Branches in Phylogenetic Trees Inferred From Molecular Sequences by Using Model-based Methods," Journal of Applied Genetics, 49(1):49-67, Springer, United Kingdom (2008).
Wroblewski, D., et al., "Rapid Molecular Characterization of Clostridium Difficile and Assessment of Populations of C. Difficile in Stool Specimens," Journal of Clinical Microbiology, 47(7):2142-2148, American Society for Microbiology, United States (Jul. 2009).
Yamakawa, K., et al., "Enhancement of Clostridium Difficile Toxin Production in Biotin-limited Conditions," Journal of Medical Microbiology, 44(2):111-114, Microbiology Society, United Kingdom (Feb. 1996).
Yamamura, H., et al., "Application of Sucrose-gradient Centrifugation for Selective Isolation of *Nocardia* Spp. From Soil," Journal of Applied Microbiology, 95(4):677-678, Published for the Society for Applied Bacteriology by Blackwell Science, United Kingdom (2003).
Yang, W.W. (201 0). Fast Viability Assessment of Clostridium Spores Survival in Extreme Environments. PhD thesis California Institute of Technology.
Yang, W.W., et al., "Production and Characterization of Pure Clostridium Spore Suspensions," Journal of Applied Microbiology, 106(1):27-33, Published for the Society for Applied Bacteriology by Blackwell Science, United Kingdom (Jan. 2009).
Yang, W.W., Ponce, A., "Rapid Endospore Viability Assay of Clostridium Sporogenes Spores," International Journal of Food Microbiology, 133(3):213-216, Elsevier Science Publishers, Netherlands (Aug. 2009).
Yang, W.W., Ponce, A., "Validation of a Clostridium Endospore Viability Assay and Analysis of Greenland Ices and Atacama Desert Soils," Applied and Environmental Microbiology, 77(7):2352-2358, American Society for Microbiology, United States (Jan. 2011).
Yi, X., and Setlow, P., "Studies of the Commitment Step in the Germination of Spores of *Bacillus* Species," Journal of Bacteriology, 192(13):3424-3433, American Society for Microbiology, United States (Jul. 2010).
Yuguchi Hiroya et al., "Fermented Milk/Lactic Acid Bacteria Beverages and Intestinal Bacterial Flora," (Hakkonyuu/nyuusankin inryou to chounaikinsou), New Food Industry, 29(7):71-88 (1987).
Yung, P.T., and Ponce, A., "Fast Sterility Assessment by Germinable-Endospore Biodosimetry," Applied and Environmental Microbiology, 74(24):7669-7674, American Society for Microbiology, United States (Sep. 2008).
Yunoki, M., et al., "Heat Sensitivity of Human Parvovirus B19," Vox Sanguinis, 84(3):164-169, Blackwell Science, United Kingdom (Apr. 2003).
Yutin, N. and Galperin, M.Y., "A Genomic Update on Clostridial Phylogeny: Gram-negative Spore Formers and Other Misplaced Clostridia," Environmental Microbiology 15(10):2631-2641, Blackwell Science, United Kingdom (Oct. 2013).
Zar, F.A., "A Comparison of Vancomycin and Metronidazole for the Treatment of Clostridium Difficile-associated Diarrhea, Stratified by Disease Severity.," Clinical Infectious Diseases : an Official Publication of the Infectious Diseases Society of America, 45(3):302-307, Oxford University Press, United States, (Aug. 2007).
Ze, X., et al., "Ruminococcus Bromii Is a Keystone Species for the Degradation of Resistant Starch in the Human Colon," The ISME Journal, 6(8):1535-1543, Nature Publishing Group, United Kingdom (Aug. 2012).
Zeng, Y., et al., "Towards Development of Stable Formulations of a Live Attenuated Bacterial Vaccine: a Preformulation Study Facilitated by a Biophysical Approach," Human Vaccines, 5(5):322-331, Landes Bioscience, United States (May 2009).
Zhao, J., et al., "Evaluation of Endospore Purification Methods Applied to Bacillus Cereus," Separation and Purification Technology, 61(3):341-347, Elsevier Ltd, Netherlands (Jul. 2008).
Zhao, Y.,et al., "Rapsearch2: a Fast and Memory-efficient Protein Similarity Search Tool for Next-generation Sequencing Data.," Bioinformatics 28(1):125-126, Oxford University Press,United Kingdom, (Jan. 2012).
Zhou, D., et al., "Total Fecal Microbiota Transplantation Alleviates Highfat Diet-Induced Steatohepatitis in Mice via Beneficial Regulation of Gut Microbiota," Scientific Reports 7(1):11 pages, Nature Publishing Group, United Kingdom (May 2017).
Zilberberg, M.D.,et al., "Increase in Adult Clostridium Difficile-related Hospitalizations and Case-fatality Rate, United States, 2000-2005.," Emerging Infectious Diseases, 14(6):929-931, National Center for Infectious Diseases, Centers for Disease Control and Prevention (CDC), United States (Jun. 2008).
Altschul, S.F., et al., "Basic Local Alignment Search Tool," J Mol Bio 215(3):403-410, Elsevier, United Kingdom (Oct. 1990).
Altschul, S.F., et al., "Gapped BLAST and PSI-BLAST: a new generation of protein database search programs," Nucleic Acids Res 25(17):3389-3402, Oxford University Press, United Kingdom (Sep. 1997).
Atarashi, K. et al., Supporting Online Material for "Induction of Colonic Regulatory T Cells by Indigenous *Clostridium* Species,"

(56) References Cited

OTHER PUBLICATIONS

Science, accessed at URL:[https://www.ncbi.nlm.nih.gov/pmc/articles/PMC3969237/], 26 pages, American Association for the Advancement of Science, United States (Dec. 2010).
Bathena S.P.R., et al., "The Profile of Bile Acids and Their Sulfate Metabolites in Human Urine and Serum," J Chromatogr B Analyt Technol Biomed Life Sci 942-943:53-62, Elsevier, Netherlands (Dec. 2013).
Casula, G. and Cutting, S.M., "Bacillus Probiotics: Spore Germination in the Gastrointestinal Tract," Appl Environ Microbiol 68(5):2344-2352, American Society for Microbiology, United States (May 2002).
Chazouillers O., "Primary Sclerosing Cholangitis and Bile Acids," Clin Res Hepatol Gastroenterol 36:S21-S25, Elsevier Masson, France (Sep. 2012).
Chiang, J.Y.L., "Bile Acid Metabolism and Signaling," Compr Physiol 3(3):1191-1212, John Wiley and Sons, United States (Jul. 2013).
Cunliffe, R.N. and Scott, B.B., "Review Article: Monitoring for Drug Side-effects in Inflammatory Bowel Disease," Aliment Pharmacol Ther 16(4):647-662, Wiley-Blackwell, United Kingdom (Apr. 2002).
Debruyne P.R., et al., "The Role of Bile Acids in Carcinogenesis," Mutation Research 480-481:359-369, Elsevier, Netherlands (Sep. 2001).
Deleuze J.F., et al., "Defect of Multidrug-resistance 3 Gene Expression in a Subtype of Progressive Familial Intrahepatic Cholestasis," Hepatology 23(4):904-908, Williams & Wilkins, United states (Apr. 1996).
Duboc H., et al., "Connecting Dysbiosis, Bile-acid Dysmetabolism and Gut Inflammation in Inflammatory Bowel Diseases," Gut 62(4):531-539, British Medical Association, United Kingdom (Apr. 2013).
Duc, L.H., et al., "Characterization of Bacillus Probiotics Available for Human Use," Applied and Environmental Microbiology 70(4):2161-2171, American Society for Microbiology, United States (Apr. 2004).
Faubion W.A., et al., "Toxic Bile Salts Induce Rodent Hepatocyte Apoptosis via Direct Activation of Fas," The Journal of clinical investigation 103(1):137-145, American Society for Clinical Investigation, United states (Jan. 1999).
Fickert P., et al., "A New Xenobiotic-induced Mouse Model of Sclerosing Cholangitis and Biliary Fibrosis," The American journal of pathology 171(2): 525-536, Elsevier, United states (Aug. 2007).
Fickert, P., et al., "Regurgitation of Bile Acids from Leaky Bile Ducts Causes Sclerosing Cholangitis In Mdr2 (Abcb4) Knockout Mice," Gastroenterology 127(1):261-274, W.B. Saunders, United States (Jul. 2004).
Final Office Action dated Apr. 14, 2020, in U.S. Appl. No. 16/223,008, Henn, M.R. et al., filed Dec. 17, 2018, 11 pages.
Final Office Action dated Jul. 29, 2020, in U.S. Appl. No. 15/778,095, Button, J. et al., filed May 22, 2018, 40 pages.
Hickson, M., et al., "Use of probiotic Lactobacillus preparation to prevent diarrhoea associated with antibiotics: randomised double blind placebo controlled trial," BMJ 335(7610):80, 5 pages, British Medical Association, United Kingdom (Jul. 2007).
Hofmann A.F., "The Continuing Importance of Bile Acids in Liver and Intestinal Disease," Archives of internal medicine 159(22):2647-2658, American Medical Association, United states (Dec. 1999).
Hong, H.A., et al., "The Use of Bacterial Spore Formers as Probiotics," FEMS Microbiology Reviews 29(4):813-835, Oxford University Press, United Kingdom (Sep. 2005).
Hylemon, P.B., et al., "Bile acids as regulatory molecules," Journal of Lipid Research 50(8):1509-1520, Lipid Research, Inc., United States (Aug. 2009).
International Search Report and Written Opinion for Application No. PCT/US2018/046769, Rijswijk, European Patent Office, dated Nov. 22, 2018, 12 pages.
International Search Report and Written Opinion for International Application No. PCT/US2019/025010, European Patent Office, Netherlands, dated Jul. 11, 2019, 12 pages.

Kabeerdoss, J., et al., "Clostridium Leptum Group Bacteria Abundance and Diversity in the Fecal Microbiota of Patients With Inflammatory Bowel Disease: A Case-control Study in India," BMC Gastroenterology 13:20, BioMed Central, United Kingdom (Jan. 2013).
Kim., et al., "Spontaneous Hepatocarcinogenesis In Farnesoid X Receptor-Null Mice," Carcinogenesis 28(5): 940-946, Irl Press At Oxford University Press, United Kingdom (May 2007).
Kohli R., et al., "Bile Acid Signaling: Mechanism for Bariatric Surgery, Cure for Nash?," Digestive diseases 33(3):440-446, Karger, Switzerland (2015).
Koransky, J. R., et al., "Use of ethanol for selective isolation of sporeforming microorganisms," Appl Environ Microbiol 35(4):762-765, American Society for Microbiology, United States (Apr. 1978).
Martinez-Montiel, M.P., et al., "Pharmacologic Therapy for Inflammatory Bowel Disease Refractory to Steroids," Clinical and Experimental Gastroenterology 8:257-269, Dove Medical Press, New Zealand (Aug. 2015).
Maziade, P.-J., et al., "Impact of adding prophylactic probiotics to a bundle of standard preventative measures for Clostridium difficile infections: enhanced and sustained decrease in the incidence and severity of infection at a community hospital," Curr Med Res Opin 29(10):1341-1347, Taylor & Francis, United Kingdom (2013).
M'koma, A.E., "Inflammatory Bowel Disease: an Expanding Global Health Problem," Clinical Medicine Insights. Gastroenterology 6:33-47, SAGE Publications, United States (Aug. 2013).
Monte M.J., et al., "Bile Acids: Chemistry, Physiology, and Pathophysiology," World journal of gastroenterology 15(7):804-816, WJG Press, United States (Feb. 2009).
Myers, E.W. and Miller, W., "Optimal Alignments in Linear Space", Computer Applications in the Biosciences 4(1):11-17, Oxford University Press, United Kingdom (Mar. 1988).
Needleman, S.B. and Wunsch, C.D., "A General Method Applicable to the Search for Similarities in the Amino Acid Sequence of Two Proteins," Journal of Molecular Biology 48(3):443-453, Academic Press, United Kingdom (Mar. 1970).
Non Final Office Action dated Jun. 15, 2018, in U.S. Appl. No. 15/359,439, filed Nov. 22, 2016, 13 pages.
Non-Final Office Action dated Dec. 9, 2019, in U.S. Appl. No. 16/223,008, Matthew R. Henn et al., filed Dec. 17, 2018, 17 pages.
Pares A., et al., "Excellent long-term survival in patients with primary biliary cirrhosis and biochemical response to ursodeoxycholic Acid," Gastroenterology 130(3):715-720, Baltimore, United Staes (Mar. 2006).
Paumgartner G., and Beuers U., "Ursodeoxycholic Acid in Cholestatic Liver Disease: Mechanisms of Action and Therapeutic Use Revisited," Hepatology 36(3):525-531, Williams & Wilkins, United States (Sep. 2002).
Ridlon J.M., et al., "Bile Salt Biotransformations by Human Intestinal Bacteria," Journal of lipid research ;47(2):241-259, Lipid Research, United states (Feb. 2006).
Sayin S.I., et al., "Gut Microbiota Regulates Bile Acid Metabolism by Reducing the Levels of Tauro-beta-muricholic Acid, a Naturally Occurring Fxr Antagonist," Cell metabolism 17(2):225-235, Cell Press, United states (Feb. 2013).
Seki Y., et al., "Two Neonatal Cholestasis Patients With Mutations in the Srd5b1 (Akr1d1) Gene: Diagnosis and Bile Acid Profiles During Chenodeoxycholic Acid Treatment," Journal of inherited metabolic disease 36(3):565-573, MTP Press, United states (May 2013).
Setchell, K.D., et al., "Hepatic Bile Acid Metabolism During Early Development Revealed From The Analysis of Human Fetal Gallbaldder Bile," Journal of Biological Chemistry 263(32):16637-16644, American Society for Biochemistry and Molecular Biology, United States (Nov. 1988).
Sinal, C.J., et al., "Targeted disruption of the nuclear receptor FXR/BAR impairs bile acid and lipid homeostasis," Cell 102(6):731-744, Cell Press, United States (Sep. 2000).
Smit, J.J., et al., "Homozygous Disruption of the Murine Mdr2 P-Glycoprotein Gene Leads To a Complete Absence of Phospholipid from Bile and to Liver Disease," Cell 75(3):451-462, Cell Press, United States (Nov. 1993).

(56) References Cited

OTHER PUBLICATIONS

Sokol R.J., et al., "Evidence for Involvement of Oxygen Free Radicals in Bile Acid Toxicity to Isolated Rat Hepatocytes," Hepatology 17(5):869-881, Williams & Wilkins, United States (May 1993).

Song P., et al., "Individual Bile Acids Have Differential Effects on Bile Acid Signaling in Mice," Toxicol Appl Pharmacol 283(1):57-64, Academic Press, United States (Feb. 2015).

Song, Y., et al., "Clostridium boltei partial 16S rRNA gene, strain 16351" Database NCBI Nucleotide [online] accession No. AJ508452, Apr. 18, 2003, [retrieved on Dec. 22, 2020], retrieved from the internet: URL[https://www.ncbi.nlm.nih.gov/nuccore/AJ508452], 2 pages.

Spinler, J. K., et al., "Probiotics as adjunctive therapy for preventing Clostridium difficile infection—What are we waiting for?," Anaerobe 41:51-57, Elsevier, Netherlands (Oct. 2016).

Sudarsanam, P., et al., "[Clostridium] Bolteae ATCC BAA-613 C_bolteae-3.0.1_Cont299, Whole Genome Shotgun Sequence," NCBI Accession No. ABCC02000039, Jan. 14, 2008, [retrieved on Dec. 22, 2020], retrieved from the internet URL:[https://www.ncbi.nlm.nih.gov/nuccore/ABCC02000039.1/], 99 pages.

Tabibian, J.H., et al., "Absence of The Intestinal Microbiota Exacerbates Hepatobiliary Disease In a Murine Model of Primary Sclerosing Cholangitis," Hepatology 63(1):185-196, Wiley, United States (Jan. 2016).

Thomas, C., et al., "Targeting Bile-acid Signalling for Metabolic Diseases," Nature Reviews. Drug Discovery 7(8):678-693, Nature Pub. Group, United Kingdom (Aug. 2008).

Trottier J., et al., "Metabolomic Profiling of 17 Bile Acids in Semm From Patients With Primary Biliary Cirrhosis and Primary Sclerosing Cholangitis: A Pilot Study," Digestive and liver disease 44(4):303-310, Elsevier, Netherland (Apr. 2012).

Zhu, C., et al., "Bile Acids in Regulation of Inflammation and Immunity: Friend or Foe?," Clin Exp Rheumatol 34(4 Suppl 98):25-31, Clinical And Experimental Rheumatology S.A.S, Italy (Jul.-Aug. 2016).

Ziegler, P., "The Elucidation of the Structure of Hyocholic Acid," Canadian Journal of Chemistry 34(4), Canadian Science Publishing, Canada (Dec. 1955).

Pei, C.-X., et al., "Diversity and abundance of the bacterial 16S rRNA gene sequences in forestomach of alpacas (*Lama pacos*) and sheep (*Ovis aries*)," Anaerobe 16(4):426-432, Elsevier, Netherlands (published online Jun. 2010, published in print Aug. 2010).

Song, Y., et al., "*Clostridium bolteae* sp. nov., isolated from human sources," Syst Appl Microbiol 26(1):84-89, Elsevier, Netherlands (Mar. 2003).

Peng, J., et al., "Update on Antimicrobial Resistance in Clostridium difficile: Resistance Mechanisms and Antimicrobial Susceptibility Testing," Journal of Clinical Microbiology 55(7):1998-2008, American Society for Microbiology, United States (published online Apr. 2017, published in print Jul. 2017).

Fig. 1A

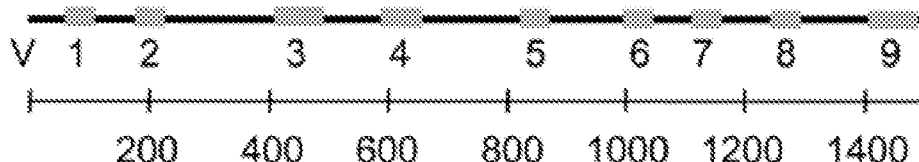

Fig. 1B

```
   1    AAATTGAAGAGTTTGATCATGGCTCAGATTGAACGCTGGCGGCAGGCCTA
  51    ACACATGCAAGTCGAACGGTAACAGGAAGAAGCTTGCTCTTTGCTGACGA
 101    GTGGCGGACGGGTGAGTAATGTCTGGGAAACTGCCTGATGGAGGGGGATA
 151    ACTACTGGAAACGGTAGCTAATACCGCATAACGTCGCAAGACCAAAGAGG
 201    GGGACCTTCGGGCCTCTTGCCATCGGATGTGCCCAGATGGGATTAGCTAG
 251    TAGGTGGGGTAACGGCTCACCTAGGCGACGATCCCTAGCTGGTCTGAGAG
 301    GATGACCAGCCACACTGGAACTGAGACACGGTCCAGACTCCTACGGGAGG
 351    CAGCAGTGGGGAATATTGCACAATGGGCGCAAGCCTGATGCAGCCATGCC
 401    GCGTGTATGAAGAAGGCCTTCGGGTTGTAAAGTACTTTCAGCGGGGAGGA
 451    AGGGAGTAAAGTTAATACCTTTGCTCATTGACGTTACCCGCAGAAGAAGC
 501    ACCGGCTAACTCGTGCCCAGGCATGCGCAGGAATACGGAGGTGCAAGCGT
 551    TAATCGGAATTACTGGGCGTAAAGCGCACGCAGGCGGTTTGTTAAGTCAG
 601    ATGTGAAATCCCCGGGCTCAACCTGGGAACTGCATCTGATACTGGCAAGC
 651    TTGAGTCTCGTAGAGGGGGGTAGAATTCCAGGTGTAGCGGTGAAATGCGT
 701    AGAGATCTGGAGGAATACCGGTGGCGAAGGCGGCCCCCTGGACGAAGACT
 751    CACGCTCAGGTGCGAAAGCGTGGGGAGCAAACAGGATTAGATACCCTGGT
 801    AGTCCACGCCGTAAACGATGTCGACTTGGAGGTTGTGCCCTTGAGGCGTG
 851    GCTTCCGGAGCTAACGCGTTAAGTCGACCGCCTGGGGAGTACGGCCGCAA
 901    GGTTAAAACTCAAATGAATTGACGGGGGCCCGCACAAGCGGTGGAGCATG
 951    TGGTTTAATTCGATGCAACGCGAAGAACCTTACCTGGTCTTGACATCCAC
1001    GGAAGTTTTCAGAGATGAGAATGTGCCTTCGGGAACCGTGAGACAGGTGC
1051    TGCATGGCTGTCGTCAGCTCGTGTTGTGAAATGTTGGGTTAAGTCCCGCA
1101    ACGAGCGCAACCCTTATCCTTTGTTGCCAGCGGTCCGGCCGGGAACTCAA
1151    AGGAGACTGCCAGTGATAAACTGGAGGAAGGTGGGGATGACGTCAAGTCA
1201    TCATGGCCCTTACGACCAGGGCTACACACGTGCTACAATGGCGCATACAA
1251    AGAGAAGCGACCTCGCGAGAGCAAGCGGACCTCATAAAGTGCGTCGTAGT
1301    CCGGATTGGAGTCTGCAACTCGACTCCATGAAGTCGGAATCGCTAGTAAT
1351    CGTGGATCAGAATGCCACGGTGAATACGTTCCCGGGCCTTGTACACACCG
1401    CCCGMCACACCATGGGAGTGGGTTGCAAAAGAAGTAGGTAGCTTAACCTT
1451    CGGGAGGGCGCTTACCACTTTGTGATTCATGACTGGGGTGAAGTCGTAAC
1501    AAGGTAACCGTAGGGGAACCTGCGGTTGGATCACCTCCTTA
```

SYNERGISTIC BACTERIAL COMPOSITIONS AND METHODS OF PRODUCTION AND USE THEREOF

CROSS REFERENCE TO RELATED APPLICATIONS

This application is a divisional of U.S. patent application Ser. No. 16/223,008, filed Dec. 17, 2018 (currently allowed), which is a continuation of U.S. patent application Ser. No. 15/359,439, filed Nov. 22, 2016 (abandoned), which is a continuation of U.S. patent application Ser. No. 14/592,481, filed Jan. 8, 2015 (now U.S. Pat. No. 9,533,014, issued on Jan. 3, 2017), which is a continuation of U.S. patent application Ser. No. 14/221,190, filed Mar. 20, 2014 (now U.S. Pat. No. 9,028,841, issued on May 12, 2015), which is a divisional of U.S. patent application Ser. No. 14/091,201, filed on Nov. 26, 2013 (now U.S. Pat. No. 8,906,668, issued on Dec. 9, 2014), which is a continuation of International Application No. PCT/US2013/071758, filed on Nov. 25, 2013, which claims the benefit of U.S. Provisional Patent Application No. 61/729,518, filed Nov. 23, 2012, U.S. Provisional Patent Application No. 61/729,519, filed Nov. 23, 2012, U.S. Provisional Patent Application No. 61/729,520, filed Nov. 23, 2012, U.S. Provisional Patent Application No. 61/729,521, filed Nov. 23, 2012, U.S. Provisional Patent Application No. 61/729,522, filed Nov. 23, 2012, U.S. Provisional Patent Application No. 61/729,524, filed Nov. 23, 2012, U.S. Provisional Patent Application No. 61/729,515, filed Nov. 23, 2012, U.S. Provisional Patent Application No. 61/729,517, filed Nov. 23, 2012, U.S. Provisional Patent Application No. 61/729,525, filed Nov. 23, 2012, U.S. Provisional Patent Application No. 61/729,526, filed Nov. 23, 2012, and U.S. Provisional Patent Application No. 61/729,527, filed Nov. 23, 2012, all of which are incorporated herein by reference in their entirety for all purposes.

REFERENCE TO A SEQUENCE LISTING SUBMITTED ELECTRONICALLY

The content of the electronically submitted sequence listing in ASCII text file (Name: 4268_024000K_Seqlisting_ST25.txt; Size: 3,949,067 bytes; and Date of Creation: Dec. 14, 2020) filed with the application is herein incorporated by reference in its entirety.

INTRODUCTION

Mammals are colonized by microbes in the gastrointestinal (GI) tract, on the skin, and in other epithelial and tissue niches such as the oral cavity, eye surface and vagina. The gastrointestinal tract harbors an abundant and diverse microbial community. It is a complex system, providing an environment or niche for a community of many different species or organisms, including diverse strains of bacteria. Hundreds of different species may form a commensal community in the GI tract in a healthy person, and this complement of organisms evolves from the time of birth to ultimately form a functionally mature microbial population by about 3 years of age. Interactions between microbial strains in these populations and between microbes and the host, e.g. the host immune system, shape the community structure, with availability of and competition for resources affecting the distribution of microbes. Such resources may be food, location and the availability of space to grow or a physical structure to which the microbe may attach. For example, host diet is involved in shaping the GI tract flora.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders, including a variety of pathogenic infections of the gut. For instance, patients become more susceptible to pathogenic infections when the normal intestinal microbiota has been disturbed due to use of broad-spectrum antibiotics. Many of these diseases and disorders are chronic conditions that significantly decrease a patient's quality of life and can be ultimately fatal.

Fecal transplantation has been shown to be an effective treatment for patients suffering from severe or refractory GI infections by repopulating the gut with a diverse array of microbes that control key pathogens by creating an ecological environment inimical to their proliferation and survival. Such approaches have demonstrated significant potential to decrease host susceptibility to infection. Fecal transplantation, however, is considered to be a procedure of last resort because it has the potential to transmit infectious or allergenic agents between hosts, involves the transmission of potentially hundreds of unknown strains from donor to patient, and is difficult to perform on a mass scale. Additionally, fecal transplantation is inherently nonstandardized and different desired and/or undesired material may be transmitted in any given donation. Fecal transplantation is not approved by the FDA and is unlikely to gain approval since the product cannot be standardized and characterized according to regulatory requirements for identity, potency, purity and safety. Thus, there is a need for defined compositions that can be used to decrease susceptibility to infection and/or that facilitate restoration of a healthy gut microbiota.

Thus practitioners have a need for a much safer and reproducible treatment for disorders currently treated on an experimental (non-FDA approved) basis using fecal transplantation. In order to prepare a therapeutic with commercial potential, we have designed bacterial compositions of isolated bacterial strains with a plurality of beneficial properties based on our understanding of those bacterial strains and our analysis of the properties that would enhance the utility and commercialization of a bacterial composition.

Therefore, in response to the need for durable, efficient, and effective compositions and methods for treatment of GI diseases, in particular serious pathogenic infections, by way of restoring or enhancing microbiota functions, we address these and other shortcomings of the prior art by providing compositions and methods for treating patients.

SUMMARY

In one aspect, provided are compositions comprising an effective amount of a bacterial composition comprising at least a first type of isolated bacterium capable of forming a spore and a second type of isolated bacterium capable of forming a spore, wherein the first type and the second type are not identical, and wherein at least one of the first type and the second type are capable of decreasing and/or inhibiting the growth and/or colonization of at least one type of pathogenic bacteria. In an embodiment, the bacterial composition comprises at least about 3, 4, 5, 6, 7, 8, 9, or 10 types of isolated bacteria. In an embodiment, the bacterial composition comprises at least about 3, 4, 5, 6, 7, 8, 9, or 10 types of isolated bacteria and at least 1, 2, 3, 4, 5, 6, 7, 8, 9, or 10 of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises: i) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria capable of forming spores, ii) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria not known to be capable of forming spores, or iii) any combination of i) and ii). In an embodiment, the first type and the second type are present in the composition in approximately equal concentrations. In an embodiment, the first type and the second type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of: i) between two and about twenty types of isolated bacteria, wherein at least two types of isolated bacteria are independently capable of spore formation; ii) between two and about twenty types of isolated bacteria, wherein at least two types of isolated bacteria not known to be capable of spore formation, or iii) any combination of i) and ii). In an embodiment, the first type of isolated bacterium and the second type of isolated bacterium are selected from Table 1. In an embodiment, the first type of isolated bacterium and the second type of isolated bacterium comprise an operational taxonomic unit (OTU) distinction. In an embodiment, the OTU distinction comprises 16S rRNA sequence similarity below about 95% identity. In an embodiment, the first type of isolated bacterium and the second type of isolated bacterium independently comprise bacteria that comprise 16S rRNA sequence at least 95% identical to 16S rRNA sequence present in a bacterium selected from SEQ ID NOs.: 1-1,864. In an embodiment, a combination of the first type and the second type are: i) cytotoxic, ii) cytostatic, iii) capable of decreasing the growth of the pathogenic bacterium, iv) capable of inhibiting the growth of the pathogenic bacterium, v) capable of decreasing the colonization of the pathogenic bacterium, vi) capable of inhibiting the colonization of the pathogenic bacterium, or vii) any combination of i)-vi). In an embodiment, the combination is capable of inhibiting proliferation of the pathogenic bacteria present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent Enterobacteriaceae (CRE), extended spectrum beta-lactam resistant Enterococci (ESBL), and vancomycin-resistant Enterococci (VRE). In an embodiment, the first type and the second type synergistically interact. In an embodiment, the first type and the second type synergistically interact to inhibit the pathogenic bacterium.

In another aspect, provided are compositions comprising an effective amount of a bacterial composition comprising at least a first type of isolated bacterium and a second type of isolated bacterium, wherein only one of the first type and the second type are capable of forming a spore, and wherein at least one of the first type and the second type are capable of decreasing the growth and/or colonization of at least one type of pathogenic bacteria.

In another aspect, provided are compositions comprising an effective amount of a bacterial composition comprising at least a first type of isolated bacterium and a second type of isolated bacterium, wherein the first type and the second type are not spores or known to be capable of forming a spore, and wherein at least one of the first type and the second type are capable of decreasing the growth and/or colonization of at least one type of pathogenic bacteria.

In an embodiment, at least one of the first type and the second type are capable of reducing the growth rate of at least one type of pathogenic bacteria. In an embodiment, at least one of the first type and the second type are cytotoxic to at least one type of pathogenic bacteria. In an embodiment, at least one of the first type and the second type are cytostatic to at least one type of pathogenic bacteria. In an embodiment, the first type and the second type are selected from Table 1. In an embodiment, the first type and the second type comprise different species. In an embodiment, the first type and the second type comprise different genera. In an embodiment, the first type and the second type comprise different families. In an embodiment, the first type and the second type comprise different orders.

In another aspect, provided are compositions comprising an effective amount of a bacterial composition comprising at least a first type of isolated bacterium and a second type of isolated bacterium, wherein: i) the first type and the second type are independently capable of forming a spore; ii) only one of the first type and the second type are capable of forming a spore or iii) neither the first type nor the second type are capable of forming a spore, wherein the first type and the second type are not identical, wherein the first type and the second type are capable of functionally populating the gastrointestinal tract of a human subject to whom the composition is administered. In an embodiment, the functional populating of the gastrointestinal tract comprises preventing a dysbiosis of the gastrointestinal tract. In an embodiment, the functional populating of the gastrointestinal tract comprises treating a dysbiosis of the gastrointestinal tract. In an embodiment, the functional populating of the gastrointestinal tract comprises reducing the severity of a dysbiosis of the gastrointestinal tract. In an embodiment, the functional populating of the gastrointestinal tract comprises reducing one or more symptoms of a dysbiosis of the gastrointestinal tract. In an embodiment, the functional populating of the gastrointestinal tract comprises preventing growth and/or colonization of the gastrointestinal tract by a pathogenic bacterium. In an embodiment, the functional populating of the gastrointestinal tract comprises reducing growth and/or colonization of the gastrointestinal tract by a pathogenic bacterium. In an embodiment, the functional populating of the gastrointestinal tract comprises reducing the number of one or more types of pathogenic bacteria in the gastrointestinal tract. In an embodiment, the functional populating of the gastrointestinal tract comprises increasing the number of one or more non-pathogenic bacteria in the gastrointestinal tract. In an embodiment, the bacterial composition comprises 0, 1, 2, 3 or greater than 3 types of isolated bacteria capable of forming spores. In an embodiment, the bacterial composition comprises at least about 5 types of isolated bacteria capable of forming spores. In an embodiment, the bacterial composition comprises at least about 7 types of isolated bacteria capable of forming spores. In an embodiment, the first type and the second type are present in the composition in not substantially equal concentrations. In an embodiment, the first type and the second type are present in the composition in approximately equal concentrations. In an embodiment, the first type is present in the composition in at least about 150% the concentration of the second type. In an embodiment, the second type is present in the composition in at least about 150% the concentration of the first type. In an embodiment, the composition consists essentially of between two and about ten types of isolated bacteria, wherein at least one type of isolated bacteria are independently capable of spore formation. In an embodiment, the first type of isolated bacterium and the second type of isolated bacterium are selected from Table 1. In an embodiment, the first type of isolated bacterium and the second type of isolated bacterium comprise an operational taxonomic unit (OTU) distinction. In an embodiment, the OTU distinction comprises 16S rRNA sequence similarity below about 95% identity. In an embodiment, the first type of isolated bacterium and the second type of isolated bacterium independently comprise bacteria that comprise 16S rRNA sequence at least 95% identical to 16S rRNA sequence present in a bacterium selected from Table 3. In an embodiment, a combination of the first type and the second type are cytotoxic or cytostatic to the pathogenic bacterium. In an embodiment, the combination is capable of inhibiting proliferation of the pathogenic bacteria present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacteria present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistant Enterobacteriaceae (CRE), extended spectrum beta-lactam resistant Enterococci (ESBL), and vancomycin-resistant Enterococci (VRE). In an embodiment, the first type and the second type synergistically interact to be cytotoxic to the pathogenic bacterium. In an embodiment, wherein the first type and the second type synergistically interact to be cytostatic to the pathogenic bacterium.

In another aspect, provided are single dose units comprising the compositions of the present invention. In an embodiment, the dose unit comprises at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of either spores or vegetative bacterial cells. In an embodiment, the dose unit comprises a pharmaceutically acceptable excipient, an enteric coating or a combination thereof. In an embodiment, the dose unit further comprises a drug selected from corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof. In an embodiment, the dose unit is formulated for oral administration, rectal administration, or the combination of oral and rectal administration, or is formulated for topical, nasal or inhalation administration.

In another aspect, provided are kits comprising in one or more containers: a first purified population of a first type of bacterial spores substantially free of viable vegetal bacterial cells; and a second purified population of a second type of bacterial spores substantially free of viable vegetal bacterial cells, wherein the first type and the second type of bacterial spores are not identical, and wherein the first type and the second type of bacterial spores, when co-localized in a target region of a gastrointestinal tract of a human subject in need thereof, are capable of functionally populating the gastrointestinal tract. In an embodiment, the first purified population and the second purified population are present in a single container. In an embodiment, the first purified population and the second purified population are present in two containers. In an embodiment, the first purified population and the second purified population are lyophilized or substantially dehydrated. In an embodiment, the kit further comprises in one or more containers an effective amount of an anti-bacterial agent, an effective amount of an anti-viral agent, an effective amount of an anti-fungal agent, an effective amount of an anti-parasitic agent, or a combination thereof in one or more containers. In an embodiment, the kit further comprises a pharmaceutically acceptable excipient or diluent.

Also provided are pharmaceutical formulations comprising an effective amount of the compositions of the invention, and further comprising an effective amount of an anti-bacterial agent, an effective amount of an anti-fungal agent, an effective amount of an anti-viral agent, an effective amount of an anti-parasitic agent.

Also provided are comestible products comprising a first purified population of a first type of bacterial spores and a second purified population of a second type of bacterial spores, wherein the first type and the second type of bacterial spores are not identical, wherein the comestible product is substantially free of viable vegetal bacterial cells, and wherein the first type and the second type of bacterial spores, when administered to a human subject in need thereof, are capable of functionally populating the gastrointestinal tract of the human subject. In an embodiment, the comestible product comprises a food or food additive, a beverage or beverage additive, or a medical food. In an embodiment, the comestible product comprises at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of viable spores. In an embodiment, the comestible product comprises a first type of bacterial spores and a second type of bacterial spores selected from Table 1, or where the first type of bacterial spores and the second type of bacterial spores independently comprise bacterial spores that comprise 16S rRNA sequence at least 95% identical to 16S rRNA sequence present in a bacterium selected from SEQ ID NOs.: 1-1,864.

Also provided are methods comprising administering to a human subject in need thereof an effective amount of a bacterial composition comprising at least a first type of isolated bacterium and a second type of isolated bacterium, wherein: the first type and the second type are independently capable of forming a spore; only one of the first type and the second type are capable of forming a spore or neither the first type nor the second type are capable of forming a spore, wherein the first type and the second type are not identical, and wherein at least one of the first type and the second type exert an inhibitory-effect on a pathogenic bacterium present in the gastrointestinal tract of the human subject, such that the number of pathogenic bacteria present in the gastrointestinal tract is not detectably increased or is detectably decreased over a period of time. In an embodiment, the human subject is diagnosed as having a dysbiosis of the gastrointestinal tract. In an embodiment, wherein the human subject is diagnosed as infected with a pathogenic bacterium selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent Enterobacteriaceae (CRE), extended spectrum beta-lactam resistant Enterococci (ESBL), and vancomycin-resistant Enterococci (VRE). In an embodiment, the bacterial composition is administered simultaneously with i) an antibiotic, ii) a prebiotic, or iii) a combination of i) and ii). In an embodiment, the bacterial composition is administered prior to administration of i) an antibiotic, ii) a prebiotic, or iii) a combination of i) and ii). In an embodiment, the bacterial composition is administered subsequent to administration of i) an antibiotic, ii) a prebiotic, or iii) a combination of i) and ii). In an embodiment, the number of pathogenic bacterium present in or excreted from the gastrointestinal tract of the human subject is detectably reduced within one month, within two weeks, or within one week of administration of the bacterial composition. In an embodiment, the number of pathogenic bacterium present in or excreted from the gastrointestinal tract of the human subject is detectably reduced within three days, two days or one day of administration of the bacterial composition. In an embodiment, the human subject is detectably free of the pathogenic bacterium within one month, two weeks, one week, three days or one day of administration of the bacterial composition. In an embodiment, the bacterial composition comprises at least about 3, 4, 5, 6, 7, 8, 9, or 10 types of isolated bacteria. In an embodiment, the bacterial composition comprises at least about 3, 4, 5, 6, 7, 8, 9, or 10 types of isolated bacteria and at least 1, 2, 3, 4, 5, 6, 7, 8, 9, or 10 of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises: i) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria capable of forming spores, ii) at least about 3, 4, 5, 6, 7, 8, 9, 10, 11, 12, 13, 14, 15, 16, 17, 18, 19, 20, 21, 22, 23, 24, 25, 26, 27, 28, 29, 30 or more types of isolated bacteria not known to be capable of forming spores, or iii) any combination of i) and ii). In an embodiment, the bacterial composition comprises at least about 5 types of isolated bacteria and at least 1 of the isolated bacteria are capable of forming spores. In an embodiment, the bacterial composition comprises at least about 5 types of isolated bacteria and at least 1 of the isolated bacteria is not capable of forming spores. In an embodiment, the bacterial composition comprises at least about 3, 4, 5, 6, 7, 8, 9 or 10 types of isolated bacteria, wherein i) at least 1, 2, 3, 4, 5, 6, 7, 8, 9 or 10 types of isolated bacteria are capable of forming spores, ii) at least 1, 2, 3, 4, 5, 6, 7, 8, 9 or 10 types of isolated bacteria are not capable of forming spores, or iii) any combination of i) and ii). In an embodiment, the first type and the second type are present in the composition in approximately equal concentrations. In an embodiment, the first type and the second type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of between two and about ten types of isolated bacteria, wherein at least two types of isolated bacteria are independently capable of spore formation. In an embodiment, the composition consists essentially of between two and about ten types of isolated bacteria, wherein at least two types of isolated bacteria are not capable of spore formation. In an embodiment, the first type of isolated bacterium and the second type of isolated bacterium are selected from Table 1. In an embodiment, the first type of isolated bacterium and the second type of isolated bacterium comprise an operational taxonomic unit (OTU) distinction. In an embodiment, the OTU distinction comprises 16S rRNA sequence similarity below about 95% identity. In an embodiment, the first type of isolated bacterium and the second type of isolated bacterium independently comprise bacteria that comprise 16S rRNA sequence at least 95% identical to 16S rRNA sequence present in a bacterium selected from SEQ ID NOs: 1-1,864. In an embodiment, a combination of the first type and the second type are cytotoxic or cytostatic to the pathogenic bacterium. In an embodiment, the combination is capable of inhibiting proliferation of the pathogenic bacterial present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, Carbapenem-resistent Enterobacteriaceae (CRE), extended spectrum beta-lactam resistant Enterococci (ESBL), and vancomycin-resistant Enterococci (VRE). In an embodiment, the first type and the second type synergistically interact to be cytotoxic to the pathogenic bacterium. In an embodiment, the first type and the second type synergistically interact to be cytostatic to the pathogenic bacterium.

Also provided are methods of functionally populating the gastrointestinal tract of a human subject, comprising administering to the subject an effective amount of a bacterial composition comprising at least a first type of isolated bacterium and a second type of isolated bacterium, wherein i) the first type and the second type are independently capable of forming a spore; ii) only one of the first type and the second type are capable of forming a spore or iii) neither the first type nor the second type are capable of forming a spore, wherein the first type and the second type are not identical, under conditions such that the first type and the second type functionally populate the gastrointestinal tract of the human subject. In an embodiment, the bacterial composition is orally administered, rectally administered, or the combination of orally and rectally administered. In an embodiment, the bacterial composition is topically or nasally administered or inhaled. In an embodiment, the first type of isolated bacteria and the second type of isolated bacteria are selected from Table 1. In an embodiment, the bacterial composition consists essentially of spores, wherein the spores comprise spores of the first type of isolated bacteria and spores of the second type of isolated bacteria. In an embodiment, the first type of isolated bacteria and the second type of isolated bacteria independently comprise bacterial spores that comprise 16S rRNA sequence at least 95% identical to 16S rRNA sequence present in a bacterium selected from SEQ ID NOs. 1-1,864. In an embodiment, the functional populating of the gastrointestinal tract comprises preventing a dysbiosis of the gastrointestinal tract. In an embodiment, the functional populating of the gastrointestinal tract comprises treating a dysbiosis of the gastrointestinal tract. In an embodiment, the functional populating of the gastrointestinal tract comprises reducing the severity of a dysbiosis of the gastrointestinal tract. In an embodiment, the functional populating of the gastrointestinal tract comprises reducing one or more symptoms of a dysbiosis of the gastrointestinal tract. In an embodiment, the functional populating of the gastrointestinal tract comprises preventing colonization of the gastrointestinal tract by a pathogenic bacterium. In an embodiment, the functional populating of the gastrointestinal tract comprises reducing colonization of the gastrointestinal tract and/or growth by a pathogenic bacterium. In an embodiment, wherein the functional populating of the gastrointestinal tract comprises reducing the number of one or more types of pathogenic bacteria in the gastrointestinal tract. In an embodiment, the functional populating of the gastrointestinal tract comprises increasing the number of one or more non-pathogenic bacteria in the gastrointestinal tract. In an embodiment, the bacterial composition comprises at least about 3, 5, 7 or 9 types of isolated bacteria capable of forming spores. In an embodiment, the bacterial composition comprises at least about 5 types of isolated bacteria and at least 20% of the isolated bacteria are capable of forming spores. In an embodiment, the bacterial composition comprises at least about 5 types of isolated bacteria and at least 2 of the isolated bacteria are capable of forming spores. In an embodiment, the bacterial composition comprises at least about 3, 4, 5, 6, 7, 8, 9 or 10 types of isolated bacteria, wherein i) at least 1, 2, 3, 4, 5, 6, 7, 8, 9 or 10 types of isolated bacteria are capable of forming spores, ii) at least 1, 2, 3, 4, 5, 6, 7, 8, 9 or 10 types of isolated bacteria are not capable of forming spores, or iii) any combination of i) and ii). In an embodiment, the first type and the second type are present in the composition in approximately equal concentrations. In an embodiment, the first type and the second type are present in the composition in not substantially equal concentrations. In an embodiment, the first type is present in the composition in at least about 150% the concentration of the second type, or wherein the second type is present in the composition in at least about 150% the concentration of the first type. In an embodiment, the composition consists essentially of between two and about ten types of isolated bacteria, wherein i) at least one type of isolated bacteria is capable of spore formation, ii) at least one type of isolated bacteria is not capable of spore formation, or iii) a combination of i) and ii). In an embodiment, a combination of the first type and the second type are inhibitory to the pathogenic bacterium. In an embodiment, the combination reduces the growth rate of the pathogenic bacterium. In an embodiment, the combination is cytostatic or cytotoxic to the pathogenic bacterium. In an embodiment, the combination is capable of inhibiting growth of the pathogenic bacterial present at a concentration at least equal to the concentration of the combination of the first type and the second type. In an embodiment, the combination is capable of inhibiting growth of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus,* multi-drug resistant bacteria, Carbapenem-resistent Enterobacteriaceae (CRE), extended spectrum beta-lactam resistant Enterococci (ESBL), and vancomycin-resistant Enterococci (VRE). In an embodiment, the first type and the second type synergistically interact to reduce or inhibit the growth of the pathogenic bacterium. In an embodiment, the first type and the second type synergistically interact to reduce or inhibit the colonization of the pathogenic bacterium. In an embodiment, the method comprises administering to the human subject a single dose unit comprising at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or greater than $1 \times 10^{11}$ colony forming units (CFUs) of viable bacteria. In an embodiment, the dose unit comprises a bacterial population substantially in the form of spores. In an embodiment, the dose unit comprises a pharmaceutically acceptable excipient and/or an enteric coating. In an embodiment, the unit dose is formulated for oral administration, rectal administration, or the combination of oral and rectal administration. In an embodiment, the unit dose is formulated for topical or nasal administration or for inhalation.

In another aspect, provided are methods of reducing the number of pathogenic bacteria present in the gastrointestinal tract of a human subject, comprising administering to the subject an effective amount of a pharmaceutical formulation comprising an effective amount of the composition of claim 1 and further comprising an effective amount of an antimicrobial agent, under conditions such that the number of pathogenic bacteria present in the gastrointestinal tract of the human subject is reduced within about one month of administration of the pharmaceutical formulation. In an embodiment, the number of pathogenic bacteria present in the gastrointestinal tract of the human subject is reduced within about two weeks of administration of the pharmaceutical formulation. In an embodiment, the number of pathogenic bacteria present in the gastrointestinal tract of the human subject is reduced within about one week of administration of the pharmaceutical formulation. In an embodiment, the number of pathogenic bacteria present in the gastrointestinal tract of the human subject is reduced within about three days of administration of the pharmaceutical formulation. In an embodiment, the number of pathogenic bacteria present in the gastrointestinal tract of the human subject is reduced within about one day of administration of the pharmaceutical formulation. In an embodiment, the anti-microbial agent comprises anti-bacterial agent. In an embodiment, the anti-microbial agent comprises anti-fungal agent. In an embodiment, the anti-microbial agent comprises anti-viral agent. In an embodiment, the anti-microbial agent comprises anti-parasitic agent.

In another aspect, provided are methods of preparing a comestible product, comprising combining with a comestible carrier a first purified population comprising at least a first type of isolated bacterium and a second purified population comprising at least a second type of isolated bacterium, wherein: i) the first type and the second type are independently capable of forming a spore; ii) only one of the first type and the second type are capable of forming a spore or iii) neither the first type nor the second type are capable of forming a spore, wherein the first type and the second type of bacteria are not identical, wherein the comestible product is substantially free of non-comestible materials. In an embodiment, at least one of the first purified population and the second purified population consist essentially of viable spores. In an embodiment, the first purified population and the second purified population consist essentially of viable spores. In an embodiment, the comestible product is substantially free of viable vegetal bacterial cells. In an embodiment, the viable spores, when the comestible product is consumed by a human subject in need thereof, are capable of functionally populating the gastrointestinal tract of the human subject. In an embodiment, the comestible product comprises a food or food additive. In an embodiment, the comestible product comprises a beverage or beverage additive. In an embodiment, the comestible product comprises a medical food. In an embodiment, the comestible product comprises at least $1\times10^4$, $1\times10^5$, $1\times10^6$, $1\times10^7$, $1\times10^8$, $1\times10^9$, $1\times10^{10}$, $1\times10^{11}$ or greater than $1\times10^{11}$ colony forming units (CFUs) of viable spores. In an embodiment, spores are of a bacterium selected from Table 1. In an embodiment, the first purified population and the second purified population independently comprise bacterial spores that comprise 16S rRNA sequence at least 95% identical to 16S rRNA sequence present in a bacterium selected from SEQ ID NOs: 1-1,864.

Also provided are methods of reducing the abundance of a pathogen in the gastrointestinal tract of a patient comprising administering the composition of the invention in a therapeutically effective amount and allowing the bacterial composition to compete with the pathogen in the gastrointestinal tract of a patient.

Further provided are methods of treating diarrhea comprising administering the composition of the invention in a therapeutically effective amount and allowing the bacterial composition to reduce the diarrheal effect of a pathogen in the gastrointestinal tract of a patient. In an embodiment, the pathogen is *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (LT or ST), *Escherichia coli* 0157:H7, *Helicobacter pylori, Lysteria monocytogenes, Plesiomonas shigelloides, Salmonella* spp., *Salmonella typhi, Shigella* spp., *Staphylococcus* spp., *Staphylococcus aureus, Vibrio* spp., *Vibrio cholerae, Vibrio parahaemolyticus, Vibrio vulnificus, Yersinia enterocolitica*, multi-drug resistant bacteria, Carbapenem-resistent Enterobacteriaceae (CRE), and vancomycin-resistant Enterococci (VRE). In an embodiment, the pathogen is *Clostridium difficile, Salmonella* spp., pathogenic *Escherichia coli*, or vancomycin-resistant *Enterococcus* spp. In an embodiment, the pathogen is *Clostridium difficile*. In an embodiment, the composition is administered orally.

Also provided are therapeutic compositions comprising a first purified bacterial population capable forming spores consisting of *Collinsella aerofaciens* and a second purified bacterial population consisting of a species selected from Table 1 or SEQ ID NOs: 1,865-1,915, wherein at least one of the first type and the second type are cytotoxic or cytostatic to a pathogenic bacterium. In an embodiment, a synergistic combination of the first bacterial spore population and the second bacterial spore population are cytotoxic or cytostatic to the pathogenic bacterium. In an embodiment, the combination is capable of inhibiting proliferation of the pathogenic bacterial present at a concentration at least equal to the concentration of the combination of the first type and the second type. In an embodiment, the combination is capable of inhibiting proliferation of the pathogenic bacterial present at a concentration at least about twice the concentration of the combination of the first type and the second type. In an embodiment, the combination is capable of inhibiting proliferation of the pathogenic bacterial present at a concentration at least about ten times the concentration of the combination of the first type and the second type. In an embodiment, the pathogenic bacterium is selected from the group consisting of *Yersinia, Vibrio, Treponema, Streptococcus, Staphylococcus, Shigella, Salmonella, Rickettsia, Pseudomonas, Neisseria, Mycoplasma, Mycobacterium, Listeria, Leptospira, Legionella, Helicobacter, Haemophilus, Francisella, Escherichia, Enterococcus, Corynebacterium, Clostridium, Chlamydia, Chlamydophila, Campylobacter, Brucella, Borrelia*, and *Bordetella*. In an embodiment, the pathogenic bacterium is *Clostridium dificile*. In an embodiment, the first bacterial spore population and the second bacterial spore population synergistically interact to be cytotoxic to the pathogenic bacterium. In an embodiment, the first bacterial spore population and the second bacterial spore population synergistically interact to be cytostatic to the pathogenic bacterium. In an embodiment, the bacterial composition comprises at least about 3 types of isolated bacteria capable of forming spores. In an embodiment, the bacterial composition comprises at least about 5 types of isolated bacteria capable of forming spores. In an embodiment, the first bacterial spore population and the second bacterial spore population are present in the composition in approximately equal concentrations. In an embodiment, the composition consists essentially of between two and about ten bacterial spore populations of isolated bacteria.

In another aspect, provided are therapeutic compositions comprising a first purified bacterial spore population consisting of bacteria comprising 16S rRNA sequence at least about 97% identical to a 16S rRNA sequence present in a reference *Collinsella aerofaciens* OTU, and a second purified bacterial spore population consisting of bacteria comprising 16S rRNA sequence at least about 97% identical to a 16S rRNA sequence present in a reference bacterium listed in Table 1 or SEQ ID NOs: 1,865-1,915, wherein at least one of the first type and the second type are cytotoxic or cytostatic to a pathogenic bacterium. In an embodiment, a synergistic combination of the first type and the second type are cytotoxic or cytostatic to the pathogenic bacterium. In an embodiment, wherein the combination is capable of inhibiting proliferation of the pathogenic bacterial present at a concentration at least equal to the concentration of the combination of the first type and the second type. In an embodiment, the first type and the second type synergistically interact to be cytotoxic or cytostatic to the pathogenic bacterium. In an embodiment, the first purified bacterial spore population and the second purified bacterial spore population are capable of functionally populating the gastrointestinal tract of a human subject to whom the composition is administered. In an embodiment, the functional populating of the gastrointestinal tract comprises preventing, treating, reducing the severity of or reducing a symptom of a dysbiosis of the gastrointestinal tract. In an embodiment, the functional populating of the gastrointestinal tract comprises i) reducing the number of one or more types of pathogenic bacteria in the gastrointestinal tract; or ii) increasing the number of one or more non-pathogenic bacteria in the gastrointestinal tract. In an embodiment, the composition further comprises an effective amount of an anti-bacterial agent, an anti-fungal agent, an anti-viral agent or an anti-parasitic agent.

Also provided are methods of treating or preventing a recurrence of a *Clostridium difficile* infection, comprising administering to a human subject in need thereof an effective amount of the therapeutic composition of the invention under conditions such that the first purified bacterial spore population and the second purified bacterial spore population exert a cytotoxic or cytostatic effect on a pathogenic bacterium present in the gastrointestinal tract of the human subject, such that the number of *Clostridium difficile* bacteria present in the gastrointestinal tract is not detectably increased or is detectably decreased over a period of time. In an embodiment, the number of *Clostridium difficile* bacteria present in or excreted from the gastrointestinal tract of the human subject is detectably reduced within one month of administration of the bacterial composition. In an embodiment, the first purified bacterial spore population and the second purified bacterial spore population synergistically interact to be cytotoxic and/or cytostatic to the *Clostridium difficile* bacteria. In an embodiment, the therapeutic composition is orally administered. In an embodiment, the therapeutic composition comprises a medical food.

In another aspect, provided are kits comprising in one or more containers: a first purified population of a first type of bacteria capable of forming spores; and a second purified population of a second type of bacteria capable of forming spores, wherein the first type and the second type are not identical, and wherein the first type and the second type, when co-localized in a target region of a gastrointestinal tract of a human subject in need thereof, are capable of functionally populating the gastrointestinal tract. In an embodiment, the first purified population and the second purified population are present in a single container. In an embodiment, the kit is formulated for use as a nutritional supplement and optionally comprising a prebiotic material.

Additional objects and advantages will be set forth in part in the description which follows, and in part will be obvious from the description, or may be learned by practice of the embodiments. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to further explain the embodiments.

BRIEF DESCRIPTION OF THE DRAWINGS

FIG. 1A provides a schematic of 16S rRNA gene and denotes the coordinates of hypervariable regions 1-9 (V1-V9). Coordinates of V1-V9 are 69-99, 137-242, 433-497, 576-682, 822-879, 986-1043, 1117-1173, 1243-1294, and 1435-1465 respectively, based on numbering using *E. coli* system of nomenclature defined by Brosius et al., Complete nucleotide sequence of a 16S ribosomal RNA gene (16S rRNA) from *Escherichia coli*, PNAS 75(10):4801-4805 (1978). FIG. 1B highlights in bold the nucleotide sequences for each hypervariable region in the exemplary reference *E. coli* 16S sequence described by Brosius et al. FIG. 1B discloses SEQ ID NO: 1926.

BRIEF DESCRIPTION OF TABLES

Table 1 provides bacterial species and Operational Taxonomic Units (OTUs) of the bacterial compositions of the present invention, including taxonometric status and the ability of the OTU to form a viable spore as provided herein.

Table 2 provides representative combinations of the bacterial compositions of the present invention.

16S rRNA sequences of the bacterial species and Operational Taxonomic Units (OTUs) of the bacterial compositions of the present invention are provided in the CRF version of the Sequence Listing as SEQ ID NOS 1-1,864.

The taxonometric status, exemplary phylogenetic surrogacy and 16S rRNA sequences of exemplary bacterial compositions of the present invention are provided in the CRF version of the Sequence Listing as SEQ ID NOS 1,865-1,915.

Table 3 demonstrates the efficacy of exemplary bacterial compositions of the present invention in inhibiting a pathogenic bacterium.

Table 4 demonstrates the efficacy of exemplary bacterial compositions of the present invention in inhibiting a pathogenic bacterium.

Table 5 provides representative bacterial pathogens.

Table 6 provides representative human diseases, disorders and conditions for which the provided bacterial compositions are useful.

Table 7 provides representative human diseases, disorders and conditions for which the provided bacterial compositions are useful.

Definitions

"Microbiota" refers to the communities of microbes that live in or on the patient's body, both sustainably and transiently, including eukaryotes, archaea, bacteria, and viruses (including bacterial viruses (i.e., phage)).

"Dysbiosis" refers to a state of the microbiota or microbiome of the gut or other body area, including mucosal or skin surfaces in which the normal diversity and/or function of the ecological network is disrupted. Any disruption from the preferred (e.g., ideal) state of the microbiota can be considered a dysbiosis, even if such dysbiosis does not result in a detectable decrease in health. This state of dysbiosis may be unhealthy, it may be unhealthy under only certain conditions, or it may prevent a subject from becoming healthier. Dysbiosis may be due to a decrease in diversity, the overgrowth of one or more pathogens or pathobionts, symbiotic organisms able to cause disease only when certain genetic and/or environmental conditions are present in a patient, or the shift to an ecological network that no longer provides a beneficial function to the host and therefore no longer promotes health.

A "spore" or a population of "spores" includes bacteria (or other single-celled organisms) that are generally viable, more resistant to environmental influences such as heat and bacteriocidal agents than vegetative forms of the same bacteria, and typically capable of germination and outgrowth. "Spore-formers" or bacteria "capable of forming spores" are those bacteria containing the genes and other necessary abilities to produce spores under suitable environmental conditions.

The terms "pathogen", "pathobiont" and "pathogenic" in reference to a bacterium or any other organism or entity includes any such organism or entity that is capable of causing or affecting a disease, disorder or condition of a host organism containing the organism or entity.

The term "isolated" encompasses a bacterium or other entity or substance that has been (1) separated from at least some of the components with which it was associated when initially produced (whether in nature or in an experimental setting), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a bacterium or other material that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, and a purified bacterium or bacterial population may contain other materials up to about 10%, about 20%, about 30%, about 40%, about 50%, about 60%, about 70%, about 80%, about 90%, or above about 90% and still be considered "isolated." In some embodiments, purified bacteria and bacterial populations are more than about 80%, about 85%, about 90%, about 91%, about 92%, about 93%, about 94%, about 95%, about 96%, about 97%, about 98%, about 99%, or more than about 99% pure. In the instance of bacterial compositions provided herein, the one or more bacterial types present in the composition can be independently purified from one or more other bacteria produced and/or present in the material or environment containing the bacterial type. Bacterial compositions and the bacterial components thereof are generally purified from residual habitat products.

"Inhibition" of a pathogen encompasses the inhibition of any desired function or activity of the bacterial compositions of the present invention. Demonstrations of pathogen inhibition, such as decrease in the growth of a pathogenic bacterium or reduction in the level of colonization of a pathogenic bacterium are provided herein and otherwise recognized by one of ordinary skill in the art. Inhibition of a pathogenic bacterium's "growth" may include inhibiting the increase in size of the pathogenic bacterium and/or inhibiting the proliferation (or multiplication) of the pathogenic bacterium. Inhibition of colonization of a pathogenic bacterium may be demonstrated by measuring the amount or burden of a pathogen before and after a treatment. An "inhibition" or the act of "inhibiting" includes the total cessation and partial reduction of one or more activities of a pathogen, such as growth, proliferation, colonization, and function.

The "colonization" of a host organism includes the non-transitory residence of a bacterium or other microscopic organism. As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

A "cytotoxic" activity or bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell.

To be free of "non-comestible products" means that a bacterial composition or other material provided herein does not have a substantial amount of a non-comestible product, e.g., a product or material that is inedible, harmful or otherwise undesired in a product suitable for administration, e.g., oral administration, to a human subject. Non-comestible products are often found in preparations of bacteria from the prior art.

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as micro RNA and ribosomal RNA, the epigenome, plasmids, and all other types of genetic information.

"Residual habitat products" refers to material derived from the habitat for microbiota within or on a human or animal. For example, microbiota live in feces in the gastrointestinal tract, on the skin itself, in saliva, mucus of the respiratory tract, or secretions of the genitourinary tract (i.e., biological matter associated with the microbial community). Substantially free of residual habitat products means that the bacterial composition no longer contains the biological matter associated with the microbial environment on or in the human or animal subject and is 100% free, 99% free, 98% free, 97% free, 96% free, or 95% free of any contaminating biological matter associated with the microbial community. Residual habitat products can include abiotic materials (including undigested food) or it can include unwanted microorganisms. Substantially free of residual habitat products may also mean that the bacterial composition contains no detectable cells from a human or animal and that only microbial cells are detectable. In one embodiment, substantially free of residual habitat products may also mean that the bacterial composition contains no detectable viral (including bacterial viruses (i.e., phage)), fungal, mycoplasmal contaminants. In another embodiment, it means that fewer than $1\times10^{-2}$%, $1\times10^{-3}$%, $1\times10^{-4}$%, $1\times10^{-5}$%, $1\times10^{-6}$%, $1\times10^{-7}$%, $1\times10^{-8}$ of the viable cells in the bacterial composition are human or animal, as compared to microbial cells. There are multiple ways to accomplish this degree of purity, none of which are limiting. Thus, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of $10^{-8}$ or $10^{-9}$), such as through multiple 10-fold serial dilutions. This can further be confirmed by showing that multiple isolated colonies have similar cell shapes and Gram staining behavior. Other methods for confirming adequate purity include genetic analysis (e.g. PCR, DNA sequencing), serology and antigen analysis, enzymatic and metabolic analysis, and methods using instrumentation such as flow cytometry with reagents that distinguish desired constituents from contaminants.

"Phylogenetic tree" refers to a graphical representation of the evolutionary relationships of one genetic sequence to another that is generated using a defined set of phylogenetic reconstruction algorithms (e.g. parsimony, maximum likelihood, or Bayesian). Nodes in the tree represent distinct ancestral sequences and the confidence of any node is provided by a bootstrap or Bayesian posterior probability, which measures branch uncertainty.

"Operational taxonomic unit (OTU, plural OTUs)" refers to a terminal leaf in a phylogenetic tree and is defined by a specific genetic sequence and all sequences that share sequence identity to this sequence at the level of species. A "type" or a plurality of "types" of bacteria includes an OTU or a plurality of different OTUs, and also encompasses a strain, species, genus, family or order of bacteria. The specific genetic sequence may be the 16S sequence or a portion of the 16S sequence or it may be a functionally conserved housekeeping gene found broadly across the eubacterial kingdom. OTUs share at least 95%, 96%, 97%, 98%, or 99% sequence identity. OTUs are frequently defined by comparing sequences between organisms. Sequences with less than 95% sequence identity are not considered to form part of the same OTU.

"Clade" refers to the set of OTUs or members of a phylogenetic tree downstream of a statistically valid node in a phylogenetic tree. The clade comprises a set of terminal leaves in the phylogenetic tree that is a distinct monophyletic evolutionary unit.

In microbiology, "16S sequencing" or "16S rRNA" or "16S-rRNA" or "16S" refers to sequence derived by characterizing the nucleotides that comprise the 16S ribosomal RNA gene(s). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most bacteria, as well as fungi.

The "V1-V9 regions" of the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA (in SEQ ID NOs 1-1,864) by comparing the candidate sequence in question to the reference sequence and identifying the hypervariable regions based on similarity to the reference hypervariable regions.

The terms "subject" or "patient" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

The term "pathobiont" refer to specific bacterial species found in healthy hosts that may trigger immune-mediated pathology and/or disease in response to certain genetic or environmental factors. Chow et al., (2011) *Curr Op Immunol*. Pathobionts of the intestinal microbiota and inflammatory disease. 23: 473-80. Thus, a pathobiont is a pathogen that is mechanistically distinct from an acquired infectious organism. Thus, the term "pathogen" includes both acquired infectious organisms and pathobionts.

DETAILED DESCRIPTION

Bacterial Compositions

Provided are bacteria and combinations of bacteria of the human gut microbiota with the capacity to meaningfully provide functions of a healthy microbiota or catalyze an augmentation to the resident microbiome when administered to mammalian hosts. In particular, provided are synergistic combinations that treat, prevent, delay or reduce the symptoms of diseases, disorders and conditions associated with a dysbiosis. Representative diseases, disorders and conditions potentially associated with a dysbiosis, which are suitable for treatment with the compositions and methods as described herein, are provided in Tables 8 and 9. Without being limited to a specific mechanism, it is thought that such compositions inhibit the growth, proliferation, and/or colonization of one or a plurality of pathogenic bacteria in the dysbiotic microbiotal niche, so that a healthy, diverse and protective microbiota colonizes and populates the intestinal lumen to establish or reestablish ecological control over pathogens or potential pathogens (e.g., some bacteria are pathogenic bacteria only when present in a dysbiotic environment). Inhibition of pathogens includes those pathogens such as *C. difficile, Salmonella* spp., enteropathogenic *E coli*, multi-drug resistant bacteria such as *Klebsiella*, and *E. coli*, Carbapenem-resistent Enterobacteriaceae (CRE), extended spectrum beta-lactam resistant Enterococci (ESBL), and vancomycin-resistant Enterococci (VRE).

The bacterial compositions provided herein are produced and the efficacy thereof in inhibiting pathogenic bacteria is demonstrated as provided in further detail herein.

In particular, in order to characterize those antagonistic relationships between gut commensals that are relevant to the dynamics of the mammalian gut habitat, provided is an in vitro microplate-based screening system that demonstrates the efficacy of those bacterial compositions, including the ability to inhibit (or antagonize) the growth of a bacterial pathogen or pathobiont, typically a gastrointestinal microorganism. These methods provide novel combinations of gut microbiota species and OTUs that are able to restore or enhance ecological control over important gut pathogens or pathobionts in vivo.

Bacterial compositions may comprise two types of bacteria (termed "binary combinations" or "binary pairs") or greater than two types of bacteria. Bacterial compositions that comprise three types of bacteria are termed "ternary combinations". For instance, a bacterial composition may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21, 22, 23, 24, 25, 26, 27, 28, 29 30, 31, 32, 33, 34, 35, 36, 37, 38, 39, or at least 40, at least 50 or greater than 50 types of bacteria, as defined by species or operational taxonomic unit (OTU), or otherwise as provided herein. In one embodiment, the composition comprises at least two types of bacteria chosen from Table 1.

In another embodiment, the number of types of bacteria present in a bacterial composition is at or below a known value. For example, in such embodiments the bacterial composition comprises 50 or fewer types of bacteria, such as 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 or fewer, or 9 or fewer types of bacteria, 8 or fewer types of bacteria, 7 or fewer types of bacteria, 6 or fewer types of bacteria, 5 or fewer types of bacteria, 4 or fewer types of bacteria, or 3 or fewer types of bacteria. In another embodiment, a bacterial composition comprises from 2 to no more than 40, from 2 to no more than 30, from 2 to no more than 20, from 2 to no more than 15, from 2 to no more than 10, or from 2 to no more than 5 types of bacteria.

In some embodiments, bacterial compositions are provided with the ability to exclude pathogenic bacteria. Exemplary bacterial compositions are demonstrated to reduce the growth rate of one pathogen, *C. difficile*, as provided in the Examples, wherein the ability of the bacterial compositions is demonstrated by assessing the antagonism activity of a combination of OTUs or strains towards a given pathogen using in vitro assays.

In some embodiments, bacterial compositions with the capacity to durably exclude *C. difficile*, are developed using a methodology for estimating an Ecological Control Factor (ECF) for constituents within the human microbiota. The ECF is determined by assessing the antagonistic activity of a given commensal strain or combination of strains towards a given pathogen using an in vitro assay, resulting in observed levels of ecological control at various concentrations of the added commensal strains. The ECF for a commensal strain or combination of strains is somewhat analogous to the longstanding minimal inhibitory concentration (MIC) assessment that is employed in the assessment of antibiotics. The ECF allows for the assessment and ranking of relative potencies of commensal strains and combinations of strains for their ability to antagonize gastrointestinal pathogens. The ECF of a commensal strain or combination of strains may be calculated by assessing the concentration of that composition that is able to mediate a given percentage of inhibition (e.g., at least 10%, 20%, 50%, 70%, 75%, 80%, 85%, 90%, 95%, or 100%) of a target pathogen in the in vitro assay. Provided herein are combinations of strains or OTUs within the human microbiota that are able to significantly reduce the rate of gastrointestinal pathogen replication within the in vitro assay. These compositions are capable of providing a safe and effective means by which to affect the growth, replication, and disease severity of such bacterial pathogens.

Bacterial compositions may be prepared comprising at least two types of isolated bacteria, wherein a first type and a second type are independently chosen from the species or OTUs listed in Table 1 and SEQ ID NOs. 1-1,864. Certain embodiments of bacterial compositions with at least two types of isolated bacteria containing binary pairs are reflected in Table 2. Additionally, a bacterial composition may be prepared comprising at least two types of isolated bacteria, wherein a first OTU and a second OTU are independently characterized by, i.e., at least 95%, 96%, 97%, 98%, 99% or including 100% sequence identity to, sequences listed in SEQ ID NOs. 1-1,864. Generally, the first bacteria and the second bacteria are not the same OTU. The sequences provided in SEQ ID NOs. 1-1,864 are full 16S sequences. Therefore, in one embodiment, the first and/or second OTUs may be characterized by the full 16S sequences listed in SEQ ID NOs. 1-1,864. In another embodiment, the first and/or second OTUs may be characterized by one or more of the variable regions of the 16S sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

Methods for Determining 16S Sequence.

OTUs may be defined either by full 16S sequencing of the rRNA gene, by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes. Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

Bacterial Compositions Exclusive of Certain Bacterial Species or Strains.

In one embodiment, the bacterial composition does not comprise at least one of *Enterococcus faecalis* (previously known as *Streptococcus faecalis*), *Clostridium innocuum*, *Clostridium ramosum*, *Bacteroides ovatus*, *Bacteroides vulgatus*, *Bacteroides thetaoiotaomicron*, *Escherichia coli* (1109 and 1108-1), *Clostridum bifermentans*, and *Blautia producta* (previously known as *Peptostreptococcus productus*).

In another embodiment, the bacterial composition does not comprise at least one of *Acidaminococcus intestinalis*, *Bacteroides ovatus*, two species of *Bifidobacterium adolescentis*, two species of *Bifidobacterium longum*, *Collinsella aerofaciens*, two species of *Dorea longicatena*, *Escherichia coli*, *Eubacterium eligens*, *Eubacterium limosum*, four species of *Eubacterium rectale*, *Eubacterium ventriosumi*, *Faecalibacterium prausnitzii*, *Lactobacillus casei*, *Lactobacillus paracasei*, *Paracateroides distasonis*, *Raoultella* sp., one species of *Roseburia* (chosen from *Roseburia faecalis* or *Roseburia faecis*), *Roseburia intestinalis*, two species of *Ruminococcus torques*, and *Streptococcus mitis*.

In another embodiment, the bacterial composition does not comprise at least one of *Barnesiella intestinihominis*; *Lactobacillus reuteri*; a species characterized as one of *Enterococcus hirae*, *Enterococus faecium*, or *Enterococcus durans*; a species characterized as one of *Anaerostipes caccae* or *Clostridium indolis*; a species characterized as one of *Staphylococcus warneri* or *Staphylococcus pasteuri*; and *Adlercreutzia equolfaciens*.

In another embodiment, the bacterial composition does not comprise at least one of *Clostridium absonum*, *Clostridium argentinense*, *Clostridium baratii*, *Clostridium bifermentans*, *Clostridium botulinum*, *Clostridium butyricum*, *Clostridium cadaveris*, *Clostridium camis*, *Clostridium celatum*, *Clostridium chauvoei*, *Clostridium clostridioforme*, *Clostridium cochlearium*, *Clostridium difficile*, *Clostridium fallax*, *Clostridium felsineum*, *Clostridium ghonii*, *Clostridium glycolicum*, *Clostridium haemolyticum*, *Clostridium hastiforme*, *Clostridium histolyticum*, *Clostridium indolis*, *Clostridium innocuum*, *Clostridium irregulare*, *Clostridium limosum*, *Clostridium malenominatum*, *Clostridium novyi*, *Clostridium oroticum*, *Clostridium paraputrificum*, *Clostridium perfringens*, *Clostridium piliforme*, *Clostridium putrefaciens*, *Clostridium putrificum*, *Clostridium ramosum*, *Clostridium sardiniense*, *Clostridium sartagoforme*, *Clostridium scindens*, *Clostridium septicum*, *Clostridium sordellii*, *Clostridium sphenoides*, *Clostridium spiroforme*, *Clostridium sporogenes*, *Clostridium subterminale*, *Clostridium symbiosum*, *Clostridium tertium*, *Clostridium tetani*, *Clostridium welchii*, and *Clostridium villosum*.

In another embodiment, the bacterial composition does not comprise at least one of *Clostridium innocuum*, *Clostridum bifermentans*, *Clostridium butyricum*, *Bacteroides fragilis*, *Bacteroides thetaiotaomicron*, *Bacteroides uniformis*, three strains of *Escherichia coli*, and *Lactobacillus* sp.

In another embodiment, the bacterial composition does not comprise at least one of *Clostridium bifermentans*, *Clostridium innocuum*, *Clostridium butyricum*, three strains of *Escherichia coli*, three strains of *Bacteroides*, and *Blautia producta* (previously known as *Peptostreptococcus productus*).

In another embodiment, the bacterial composition does not comprise at least one of *Bacteroides* sp., *Escherichia coli*, and non pathogenic Clostridia, including *Clostridium innocuum*, *Clostridium bifermentans* and *Clostridium ramosum*.

In another embodiment, the bacterial composition does not comprise at least one of more than one *Bacteroides* species, *Escherichia coli* and non-pathogenic Clostridia, such as *Clostridium butyricum*, *Clostridium bifermentans* and *Clostridium innocuum*.

In another embodiment, the bacterial composition does not comprise at least one of *Bacteroides caccae*, *Bacteroides capillosus*, *Bacteroides coagulans*, *Bacteroides distasonis*, *Bacteroides eggerthii*, *Bacteroides forsythus*, *Bacteroides fragilis*, *Bacteroides fragilis-ryhm*, *Bacteroides gracilis*, *Bacteroides levii*, *Bacteroides macacae*, *Bacteroides merdae*, *Bacteroides ovatus*, *Bacteroides pneumosintes*, *Bacteroides putredinis*, *Bacteroides pyogenes*, *Bacteroides splanchnicus*, *Bacteroides stercoris*, *Bacteroides tectum*, *Bacteroides thetaiotaomicron*, *Bacteroides uniformis*, *Bacteroides ureolyticus*, and *Bacteroides vulgatus*.

In another embodiment, the bacterial composition does not comprise at least one of *Bacteroides*, *Eubacteria*, *Fusobacteria*, *Propionibacteria*, *Lactobacilli*, anaerobic *cocci*, *Ruminococcus*, *Escherichia coli*, *Gemmiger*, *Desulfomonas*, and *Peptostreptococcus*.

In another embodiment, the bacterial composition does not comprise at least one of *Bacteroides fragilis* ss. *Vulgatus*, *Eubacterium aerofaciens*, *Bacteroides fragilis* ss. *Thetaiotaomicron*, *Blautia producta* (previously known as *Peptostreptococcus productus* II), *Bacteroides fragilis* ss. *Distasonis*, *Fusobacterium prausnitzii*, *Coprococcus eutactus*, *Eubacterium aerofaciens* III, *Blautia producta* (previously known as *Peptostreptococcus productus* I), *Ruminococcus bromii*, *Bifidobacterium adolescentis*, *Gemmiger formicilis*, *Bifidobacterium longum*, *Eubacterium siraeum*, *Ruminococcus torques*, *Eubacterium rectale* III-H, *Eubacterium rectale* IV, *Eubacterium eligens*, *Bacteroides eggerthii*, *Clostridium leptum*, *Bacteroides fragilis* ss. A, *Eubacterium biforme*, *Bifidobacterium infantis*, *Eubacterium rectale* III-F, *Coprococcus comes*, *Bacteroides capillosus*, *Ruminococcus albus*, *Eubacterium formicigenerans*, *Eubacterium hali*, *Eubacterium ventriosum* I, *Fusobacterium russii*, *Ruminococcus obeum*, *Eubacterium rectale* II, *Clostridium ramosum* I, *Lactobacillus leichmanii*, *Ruminococcus cailidus*, *Butyrivibrio crossotus*, *Acidaminococcus fermentans*, *Eubacterium ventriosum*, *Bacteroides fragilis* ss. *fragilis*, *Bacteroides* AR, *Coprococcus catus*, *Eubacterium hadrum*, *Eubacterium cylindroides*, *Eubacterium ruminantium*, *Eubacterium* CH-1, *Staphylococcus epidermidis*, *Peptostreptococcus* BL, *Eubacterium limosum*, *Bacteroides praeacutus*, *Bacteroides* L, *Fusobacterium mortiferum* I, *Fusobacterium naviforme*, *Clostridium innocuum*, *Clostridium ramosum*, *Propionibacterium acnes*, *Ruminococcus flavefaciens*, *Ruminococcus* AT, *Peptococcus* AU-1, *Eubacterium* AG, -AK, -AL, -AL-1, -AN; *Bacteroides fragilis* ss. *ovatus*, -ss. d, -ss. f; *Bacteroides* L-1, L-5; *Fusobacterium nucleatum*, *Fusobacterium mortiferum*, *Escheri-*

*chia coli, Streptococcus morbiliorum, Peptococcus magnus, Peptococcus G, AU-2; Streptococcus intermedius, Ruminococcus lactaris, Ruminococcus CO Gemmiger X, Coprococcus BH, -CC; Eubacterium tenue, Eubacterium ramulus, Eubacterium AE, -AG-H, -AG-M, -AJ, -BN-1; Bacteroides clostridiiformis* ss. *clostridformis, Bacteroides coagulans, Bacteroides orails, Bacteroides ruminicola* ss. *brevis, -ss. ruminicola, Bacteroides splanchnicus, Desuifomonas pigra, Bacteroides L-4, -N-i; Fusobacterium H, Lactobacillus G*, and *Succinivibrio A*.

Inhibition of Bacterial Pathogens.

The bacterial compositions offer a protective or therapeutic effect against infection by one or more GI pathogens of interest.

A list of exemplary bacterial pathogens is provided in Table 5.

In some embodiments, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, extended spectrum beta-lactam resistant Enterococci (ESBL), Carbapenem-resistent Enterobacteriaceae (CRE), and vancomycin-resistant Enterococci (VRE).

In some embodiments, these pathogens include, but are not limited to, *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (such as, but not limited to, LT and/or ST), *Escherichia coli* 0157:H7, *Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnificus*, and *Yersinia enterocolitica*.

In one embodiment, the pathogen of interest is at least one pathogen chosen from *Clostridium difficile, Salmonella* spp., pathogenic *Escherichia coli*, vancomycin-resistant *Enterococcus* spp., and extended spectrum beta-lactam resistant Enterococci (ESBL).

In Vitro Assays Substantiating Protective Effect of Bacterial Compositions.

In one embodiment, provided is an In Vitro Assay utilizing competition between the bacterial compositions or subsets thereof and *C. difficile*. Exemplary embodiments of this Assay are provided herein and in the Examples.

In another embodiment, provided is an In Vitro Assay utilizing 10% (wt/vol) Sterile-Filtered Feces. Provided is an in vitro assay to test for the protective effect of the bacterial compositions and to screen in vitro for combinations of microbes that inhibit the growth of a pathogen. The assay can operate in automated high-throughput or manual modes. Under either system, human or animal feces may be resuspended in an anaerobic buffer solution, such as pre-reduced PBS or other suitable buffer, the particulate removed by centrifugation, and filter sterilized. This 10% sterile-filtered feces material serves as the base media for the in vitro assay. To test a bacterial composition, an investigator may add it to the sterile-filtered feces material for a first incubation period and then may inoculate the incubated microbial solution with the pathogen of interest for a second incubation period. The resulting titer of the pathogen may be quantified by any number of methods such as those described below, and the change in the amount of pathogen is compared to standard controls including the pathogen cultivated in the absence of the bacterial composition. The assay is conducted using at least one control. Feces from a healthy subject may be used as a positive control. As a negative control, antibiotic-treated feces or heat-treated feces may be used. Various bacterial compositions may be tested in this material and the bacterial compositions optionally compared to the positive and/or negative controls. The ability to inhibit the growth of the pathogen may be measured by plating the incubated material on *C. difficile* selective media and counting colonies. After competition between the bacterial composition and *C. difficile*, each well of the in vitro assay plate is serially diluted ten-fold six times, and plated on selective media, such as but not limited to cycloserine cefoxitin mannitol agar (CCMA) or cycloserine cefoxitin fructose agar (CCFA), and incubated. Colonies of *C. difficile* are then counted to calculate the concentration of viable cells in each well at the end of the competition. Colonies of *C. difficile* are confirmed by their characteristic diffuse colony edge morphology as well as fluorescence under UV light.

In another embodiment, the in vitro assay utilizes Antibiotic-Treated Feces. In an alternative embodiment, and instead of using 10% sterile-filtered feces, human or animal feces may be resuspended in an anaerobic buffer solution, such as pre-reduced PBS or other suitable buffer. The resuspended feces is treated with an antibiotic, such as clindamycin, or a cocktail of several antibiotics in order to reduce the ability of feces from a healthy subject to inhibit the growth of *C. difficile*; this material is termed the antibiotic-treated matrix. While not being bound by any mechanism, it is believed that beneficial bacteria in healthy subjects protects them from infection by competing out *C. difficile*. Treating feces with antibiotics kills or reduces the population of those beneficial bacteria, allowing *C. difficile* to grow in this assay matrix. Antibiotics in addition to clindamycin that inhibit the normal flora include ceftriaxone and piperacillin-tazobactam and may be substituted for the clindamycin. The antibiotic-treated matrix is centrifuged, the supernatant removed, and the pelleted material resuspended in filter-sterilized, diluted feces in order to remove any residual antibiotic. This washed antibiotic-treated matrix may be used in the in vitro assay described above in lieu of the 10% sterile-filtered feces.

Alternatively, the ability to inhibit the growth of the pathogen may be measured by quantitative PCR (qPCR). Standard techniques may be followed to generate a standard curve for the pathogen of interest. Genomic DNA may be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions. The qPCR may be conducted using HotMasterMix (5PRIME, Gaithersburg, Md.) and primers specific for the pathogen of interest, and may be conducted on a MicroAmp® Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (BioRad, Hercules, Calif.), with fluorescent readings of the FAM and ROX channels. The Cq value for each well on the FAM channel is determined by the CFX Manager™ software version 2.1. The $\log_{10}$ (cfu/ml) of each experimental sample is calculated by inputting a given sample's Cq value into linear regression model generated from the standard curve comparing the Cq values of the standard curve wells to the known $\log_{10}$ (cfu/ml) of those samples. The skilled artisan may employ alternative qPCR modes.

Also provided are In Vivo Assay Establishing Protective Effect of Bacterial Compositions. Provided is an in vivo mouse model to test for the protective effect of the bacterial compositions against *C. difficile*. In this model (based on Chen, et al., A mouse model of *Clostridium difficile* associated disease, Gastroenterology 135(6):1984-1992 (2008)), mice are made susceptible to *C. difficile* by a 7 day treatment (days −12 to −5 of experiment) with 5 to 7 antibiotics (including kanamycin, colistin, gentamycin, metronidazole and vancomycin and optionally including ampicillin and ciprofloxacin) delivered via their drinking water, followed by a single dose with Clindamycin on day −3, then challenged three days later on day 0 with $10^4$ spores of *C. difficile* via oral gavage (i.e., oro-gastric lavage). Bacterial compositions may be given either before (prophylactic treatment) or after (therapeutic treatment) *C. difficile* gavage. Further, bacterial compositions may be given after (optional) vancomycin treatment (see below) to assess their ability to prevent recurrence and thus suppress the pathogen in vivo. The outcomes assessed each day from day −1 to day 6 (or beyond, for prevention of recurrence) are weight, clinical signs, mortality and shedding of *C. difficile* in the feces. Weight loss, clinical signs of disease, and *C. difficile* shedding are typically observed without treatment. Vancomycin provided by oral gavage on days −1 to 4 protects against these outcomes and serves as a positive control. Clinical signs are subjective, and scored each day by the same experienced observer. Animals that lose greater than or equal to 25% of their body weight are euthanized and counted as infection-related mortalities. Feces are gathered from mouse cages (5 mice per cage) each day, and the shedding of *C. difficile* spores is detected in the feces using a selective plating assay as described for the in vitro assay above, or via qPCR for the toxin gene as described herein. The effects of test materials including 10% suspension of human feces (as a positive control), bacterial compositions, or PBS (as a negative vehicle control), are determined by introducing the test article in a 0.2 mL volume into the mice via oral gavage on day −1, one day prior to *C. difficile* challenge, on day 1, 2 and 3 as treatment or post-vancomycin treatment on days 5, 6, 7 and 8. Vancomycin, as discussed above, is given on days 1 to 4 as another positive control. Alternative dosing schedules and routes of administration (e.g. rectal) may be employed, including multiple doses of test article, and $10^3$ to $10^{10}$ of a given organism or composition may be delivered.

Methods for Preparing a Bacterial Composition for Administration to a Subject.

Methods for producing bacterial compositions may include three main processing steps, combined with one or more mixing steps. The steps are: organism banking, organism production, and preservation.

For banking, the strains included in the bacterial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. A variety of microbiological media and variations are well known in the art (e.g. R. M. Atlas, *Handbook of Microbiological Media* (2010) CRC Press). Medium can be added to the culture at the start, may be added during the culture, or may be intermittently/continuously flowed through the culture. The strains in the bacterial composition may be cultivated alone, as a subset of the bacterial composition, or as an entire collection comprising the bacterial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For bacterial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions (e.g., gut microbiota), an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine☐HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition may be purified by additional means such as density gradient centrifugation preserved using the techniques described above. Bacterial composition banking may be done by culturing and preserving the strains individually, or by mixing the strains together to create a combined bank. As an example of cryopreservation, a bacterial composition culture may be harvested by centrifugation to pellet the cells from the culture medium, the supernate decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production may be conducted using similar culture steps to banking, including medium composition and culture conditions. It may be conducted at larger scales of operation, especially for clinical development or commercial production. At larger scales, there may be several subcultivations of the bacterial composition prior to the final cultivation. At the end of cultivation, the culture is harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

Formulations.

Provided are formulations for administration to humans and other subjects in need thereof. Generally the bacterial compositions are combined with additional active and/or inactive materials in order to produce a final product, which may be in single dosage unit or in a multi-dose format.

In some embodiments the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments the composition comprises at least one lipid. As used herein a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments the excipient is a buffering agent. Non-limiting examples of suitable buffering agents include sodium citrate, magnesium carbonate, magnesium bicarbonate, calcium carbonate, and calcium bicarbonate.

In some embodiments the excipient comprises a preservative. Non-limiting examples of suitable preservatives include antioxidants, such as alpha-tocopherol and ascorbate, and antimicrobials, such as parabens, chlorobutanol, and phenol.

In some embodiments the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments the excipient comprises a flavoring agent. Flavoring agents can be chosen from synthetic flavor oils and flavoring aromatics; natural oils; extracts from plants, leaves, flowers, and fruits; and combinations thereof. In some embodiments the flavoring agent is selected from cinnamon oils; oil of wintergreen; peppermint oils; clover oil; hay oil; anise oil; *eucalyptus*; vanilla; citrus oil such as lemon oil, orange oil, grape and grapefruit oil; and fruit essences including apple, peach, pear, strawberry, raspberry, cherry, plum, pineapple, and apricot.

In some embodiments the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2, 2-dioxide, particularly the potassium salt (acesulfame-K), and sodium and calcium salts thereof.

In some embodiments the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

The weight fraction of the excipient or combination of excipients in the formulation is usually about 99% or less, such as about 95% or less, about 90% or less, about 85% or less, about 80% or less, about 75% or less, about 70% or less, about 65% or less, about 60% or less, about 55% or less, 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The bacterial compositions disclosed herein can be formulated into a variety of forms and administered by a number of different means. The compositions can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. In an exemplary embodiment, the bacterial composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments the core material comprises at least one of a solid, a liquid, and an emulsion. In some embodiments the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In some embodiments at least one polymer functions as taste-masking agents.

Tablets, pills, and the like can be compressed, multiply compressed, multiply layered, and/or coated. The coating can be single or multiple. In one embodiment, the coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments the coating material comprises a protein. In some embodiments the coating material comprises at least one of a fat and an oil. In some embodiments the at least one of a fat and an oil is high temperature melting. In some embodiments the at least one of a fat and an oil is hydrogenated or partially hydrogenated. In some embodiments the at least one of a fat and an oil is derived from a plant. In some embodiments the at least one of a fat and an oil comprises at least one of glycerides, free fatty acids, and fatty acid esters. In some embodiments the coating material comprises at least one edible wax. The edible wax can be derived from animals, insects, or plants. Non-limiting examples include beeswax, lanolin, bayberry wax, carnauba wax, and rice bran wax. Tablets and pills can additionally be prepared with enteric coatings.

Alternatively, powders or granules embodying the bacterial compositions disclosed herein can be incorporated into a food product. In some embodiments the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments the food product is a solid foodstuff. Suitable examples of a solid foodstuff include without limitation a food bar, a snack bar, a cookie, a brownie, a muffin, a cracker, an ice cream bar, a frozen yogurt bar, and the like.

In some embodiments, the compositions disclosed herein are incorporated into a therapeutic food. In some embodiments, the therapeutic food is a ready-to-use food that optionally contains some or all essential macronutrients and micronutrients. In some embodiments, the compositions disclosed herein are incorporated into a supplementary food that is designed to be blended into an existing meal. In some embodiments, the supplemental food contains some or all essential macronutrients and micronutrients. In some embodiments, the bacterial compositions disclosed herein are blended with or added to an existing food to fortify the food's protein nutrition. Examples include food staples (grain, salt, sugar, cooking oil, margarine), beverages (coffee, tea, soda, beer, liquor, sports drinks), snacks, sweets and other foods.

In one embodiment, the formulations are filled into gelatin capsules for oral administration. An example of an appropriate capsule is a 250 mg gelatin capsule containing from 10 (up to 100 mg) of lyophilized powder ($10^8$ to $10^{11}$ bacteria), 160 mg microcrystalline cellulose, 77.5 mg gelatin, and 2.5 mg magnesium stearate. In an alternative embodiment, from $10^5$ to $10^{12}$ bacteria may be used, $10^5$ to $10^7$, $10^6$ to $10^7$, or $10^8$ to $10^{10}$, with attendant adjustments of the excipients if necessary. In an alternative embodiment an enteric-coated capsule or tablet or with a buffering or protective composition may be used.

In one embodiment, the number of bacteria of each type may be present in the same amount or in different amounts. For example, in a bacterial composition with two types of bacteria, the bacteria may be present in from a 1:10,000 ratio to a 1:1 ratio, from a 1:10,000 ratio to a 1:1,000 ratio, from a 1:1,000 ratio to a 1:100 ratio, from a 1:100 ratio to a 1:50 ratio, from a 1:50 ratio to a 1:20 ratio, from a 1:20 ratio to a 1:10 ratio, from a 1:10 ratio to a 1:1 ratio. For bacterial compositions comprising at least three types of bacteria, the ratio of type of bacteria may be chosen pairwise from ratios for bacterial compositions with two types of bacteria. For example, in a bacterial composition comprising bacteria A, B, and C, at least one of the ratio between bacteria A and B, the ratio between bacteria B and C, and the ratio between bacteria A and C may be chosen, independently, from the pairwise combinations above.

Methods of Treating a Subject.

In some embodiments the proteins and compositions disclosed herein are administered to a patient or a user (sometimes collectively referred to as a "subject"). As used herein "administer" and "administration" encompasses embodiments in which one person directs another to consume a bacterial composition in a certain manner and/or for a certain purpose, and also situations in which a user uses a bacteria composition in a certain manner and/or for a certain purpose independently of or in variance to any instructions received from a second person. Non-limiting examples of embodiments in which one person directs another to consume a bacterial composition in a certain manner and/or for a certain purpose include when a physician prescribes a course of conduct and/or treatment to a patient, when a parent commands a minor user (such as a child) to consume a bacterial composition, when a trainer advises a user (such as an athlete) to follow a particular course of conduct and/or treatment, and when a manufacturer, distributor, or marketer recommends conditions of use to an end user, for example through advertisements or labeling on packaging or on other materials provided in association with the sale or marketing of a product.

The bacterial compositions offer a protective and/or therapeutic effect against infection by one or more GI pathogens of interest and thus may be administered after an acute case of infection has been resolved in order to prevent relapse, during an acute case of infection as a complement to antibiotic therapy if the bacterial composition is not sensitive to the same antibiotics as the GI pathogen, or to prevent infection or reduce transmission from disease carriers. These pathogens include, but are not limited to, *Aeromonas hydrophila*, *Campylobacter fetus*, *Plesiomonas shigelloides*, *Bacillus cereus*, *Campylobacter jejuni*, *Clostridium botulinum*, *Clostridium difficile*, *Clostridium perfringens*, enteroaggregative *Escherichia coli*, enterohemorrhagic *Escherichia coli*, enteroinvasive *Escherichia coli*, enterotoxigenic *Escherichia coli* (LT and/or ST), *Escherichia coli* 0157:H7, *Helicobacter pylori*, *Klebsiella pneumonia*, *Lysteria monocytogenes*, *Plesiomonas shigelloides*, *Salmonella* spp., *Salmonella typhi*, *Shigella* spp., *Staphylococcus*, *Staphylococcus aureus*, vancomycin-resistant *Enterococcus* spp., *Vibrio* spp., *Vibrio cholerae*, *Vibrio parahaemolyticus*, *Vibrio vulnificus*, and *Yersinia enterocolitica*.

In one embodiment, the pathogen may be *Clostridium difficile*, *Salmonella* spp., pathogenic *Escherichia coli*, Carbapenem-resistant Enterobacteriaceae (CRE), extended spectrum beta-lactam resistant Enterococci (ESBL) and vancomycin-resistant Enterococci (VRE). In yet another embodiment, the pathogen may be *Clostridium difficile*.

The present bacterial compositions may be useful in a variety of clinical situations. For example, the bacterial compositions may be administered as a complementary treatment to antibiotics when a patient is suffering from an acute infection, to reduce the risk of recurrence after an acute infection has subsided, or when a patient will be in close proximity to others with or at risk of serious gastrointestinal infections (physicians, nurses, hospital workers, family members of those who are ill or hospitalized).

The present bacterial compositions may be administered to animals, including humans, laboratory animals (e.g., primates, rats, mice), livestock (e.g., cows, sheep, goats, pigs, turkeys, chickens), and household pets (e.g., dogs, cats, rodents).

In the present method, the bacterial composition is administered enterically, in other words by a route of access to the gastrointestinal tract. This includes oral administration, rectal administration (including enema, suppository, or colonoscopy), by an oral or nasal tube (nasogastric, nasojejunal, oral gastric, or oral jejunal), as detailed more fully herein.

A. Pretreatment Protocols

Prior to administration of the bacterial composition, the patient may optionally have a pretreatment protocol to prepare the gastrointestinal tract to receive the bacterial composition. In certain embodiments, the pretreatment protocol is advisable, such as when a patient has an acute infection with a highly resilient pathogen. In other embodiments, the pretreatment protocol is entirely optional, such as when the pathogen causing the infection is not resilient, or the patient has had an acute infection that has been successfully treated but where the physician is concerned that the infection may recur. In these instances, the pretreatment protocol may enhance the ability of the bacterial composition to affect the patient's microbiome.

As one way of preparing the patient for administration of the microbial ecosystem, at least one antibiotic may be administered to alter the bacteria in the patient. As another way of preparing the patient for administration of the microbial ecosystem, a standard colon-cleansing preparation may be administered to the patient to substantially empty the contents of the colon, such as used to prepare a patient for a colonscopy. By "substantially emptying the contents of the colon," this application means removing at least 75%, at least 80%, at least 90%, at least 95%, or about 100% of the contents of the ordinary volume of colon contents. Antibiotic treatment may precede the colon-cleansing protocol.

If a patient has received an antibiotic for treatment of an infection, or if a patient has received an antibiotic as part of a specific pretreatment protocol, in one embodiment the antibiotic should be stopped in sufficient time to allow the antibiotic to be substantially reduced in concentration in the gut before the bacterial composition is administered. In one embodiment, the antibiotic may be discontinued 1, 2, or 3 days before the administration of the bacterial composition. In one embodiment, the antibiotic may be discontinued 3, 4, 5, 6, or 7 antibiotic half-lives before administration of the bacterial composition. In another embodiment, the antibiotic may be chosen so the constituents in the bacterial composition have an MIC50 that is higher than the concentration of the antibiotic in the gut.

MIC50 of a bacterial composition or the elements in the composition may be determined by methods well known in the art. Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic may be chosen so that the infection is sensitive to the antibiotic, but the constituents in the bacterial composition are not sensitive to the antibiotic.

Routes of Administration

The bacterial compositions of the invention are suitable for administration to mammals and non-mammalian animals in need thereof. In certain embodiments, the mammalian subject is a human subject who has one or more symptoms of a dysbiosis.

When the mammalian subject is suffering from a disease, disorder or condition characterized by an aberrant microbiota, the bacterial compositions described herein are suitable for treatment thereof. In some embodiments, the mammalian subject has not received antibiotics in advance of treatment with the bacterial compositions. For example, the mammalian subject has not been administered at least two doses of vancomycin, metronidazole and/or or similar antibiotic compound within one week prior to administration of the therapeutic composition. In other embodiments, the mammalian subject has not previously received an antibiotic compound in the one month prior to administration of the therapeutic composition. In other embodiments, the mammalian subject has received one or more treatments with one or more different antibiotic compounds and such treatment(s) resulted in no improvement or a worsening of symptoms.

In some embodiments, the gastrointestinal disease, disorder or condition is diarrhea caused by *C. difficile* including recurrent *C. difficile* infection, ulcerative colitis, colitis, Crohn's disease, or irritable bowel disease. Beneficially, the therapeutic composition is administered only once prior to improvement of the disease, disorder or condition. In some embodiments the therapeutic composition is administered at intervals greater than two days, such as once every three, four, five or six days, or every week or less frequently than every week. Or the preparation may be administered intermittently according to a set schedule, e.g., once a day, once weekly, or once monthly, or when the subject relapses from the primary illness. In another embodiment, the preparation may be administered on a long-term basis to subjects who are at risk for infection with or who may be carriers of these pathogens, including subjects who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

In embodiments, the bacterial composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy). The bacterial composition may be administered to at least one region of the gastrointestinal tract, including the mouth, esophagus, stomach, small intestine, large intestine, and rectum. In some embodiments it is administered to all regions of the gastrointestinal tract. The bacterial compositions may be administered orally in the form of medicaments such as powders, capsules, tablets, gels or liquids. The bacterial compositions may also be administered in gel or liquid form by the oral route or through a nasogastric tube, or by the rectal route in a gel or liquid form, by enema or instillation through a colonoscope or by a suppository.

If the composition is administered colonoscopically and, optionally, if the bacterial composition is administered by other rectal routes (such as an enema or suppository) or even if the subject has an oral administration, the subject may have a colon-cleansing preparation. The colon-cleansing preparation can facilitate proper use of the colonoscope or other administration devices, but even when it does not serve a mechanical purpose it can also maximize the proportion of the bacterial composition relative to the other organisms previously residing in the gastrointestinal tract of the subject. Any ordinarily acceptable colon-cleansing preparation may be used such as those typically provided when a subject undergoes a colonoscopy.

Dosages and Schedule for Administration

In some embodiments the bacteria and bacterial compositions are provided in a dosage form. In some embodiments the dosage form is designed for administration of at least one OTU or combination thereof disclosed herein, wherein the total amount of bacterial composition administered is selected from 0.1 ng to 10 g, 10 ng to 1 g, 100 ng to 0.1 g, 0.1 mg to 500 mg, 1 mg to 100 mg, or from 10-15 mg. In some embodiments the bacterial composition is consumed at a rate of from 0.1 ng to 10 g a day, 10 ng to 1 g a day, 100 ng to 0.1 g a day, 0.1 mg to 500 mg a day, 1 mg to 100 mg a day, or from 10-15 mg a day, or more.

In some embodiments the treatment period is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, or at least 1 year. In some embodiments the treatment period is from 1 day to 1 week, from 1 week to 4 weeks, from 1 month, to 3 months, from 3 months to 6 months, from 6 months to 1 year, or for over a year.

In one embodiment, from $10^5$ and 10 microorganisms total may be administered to the patient in a given dosage form. In one mode, an effective amount may be provided in from 1 to 500 ml or from 1 to 500 grams of the bacterial composition having from $10^7$ to $10^{11}$ bacteria per ml or per gram, or a capsule, tablet or suppository having from 1 mg to 1000 mg lyophilized powder having from $10^7$ to $10^{11}$ bacteria. Those receiving acute treatment may receive higher doses than those who are receiving chronic administration (such as hospital workers or those admitted into long-term care facilities).

Any of the preparations described herein may be administered once on a single occasion or on multiple occasions, such as once a day for several days or more than once a day on the day of administration (including twice daily, three times daily, or up to five times daily). Or the preparation may be administered intermittently according to a set schedule, e.g., once weekly, once monthly, or when the patient relapses from the primary illness. In another embodiment, the preparation may be administered on a long-term basis to individuals who are at risk for infection with or who may be carriers of these pathogens, including individuals who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

Patient Selection

Particular bacterial compositions may be selected for individual patients or for patients with particular profiles. For example, 16S sequencing may be performed for a given patient to identify the bacteria present in his or her microbiota. The sequencing may either profile the patient's entire microbiome using 16S sequencing (to the family, genera, or species level), a portion of the patient's microbiome using 16S sequencing, or it may be used to detect the presence or absence of specific candidate bacteria that are biomarkers for health or a particular disease state, such as markers of multi-drug resistant organisms or specific genera of concern such as *Escherichia*. Based on the biomarker data, a particular composition may be selected for administration to a patient to supplement or complement a patient's microbiota in order to restore health or treat or prevent disease. In another embodiment, patients may be screened to determine the composition of their microbiota to determine the likelihood of successful treatment.

Combination Therapy

The bacterial compositions may be administered with other agents in a combination therapy mode, including anti-microbial agents and prebiotics. Administration may be sequential, over a period of hours or days, or simultaneous.

In one embodiment, the bacterial compositions are included in combination therapy with one or more anti-microbial agents, which include anti-bacterial agents, anti-fungal agents, anti-viral agents and anti-parasitic agents.

Anti-bacterial agents include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

A prebiotic is a selectively fermented ingredient that allows specific changes, both in the composition and/or activity in the gastrointestinal microbiota that confers benefits upon host well-being and health. Prebiotics may include complex carbohydrates, amino acids, peptides, or other essential nutritional components for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Methods for Characterization of Bacterial Compositions

In certain embodiments, provided are methods for testing certain characteristics of bacterial compositions. For example, the sensitivity of bacterial compositions to certain environmental variables is determined, e.g., in order to select for particular desirable characteristics in a given composition, formulation and/or use. For example, the constituents in the bacterial composition may be tested for pH resistance, bile acid resistance, and/or antibiotic sensitivity, either individually on a constituent-by-constituent basis or collectively as a bacterial composition comprised of multiple bacterial constituents (collectively referred to in this section as bacterial composition).

pH Sensitivity Testing. If a bacterial composition will be administered other than to the colon or rectum (i.e., through, for example, but not limited to, an oral route), optionally testing for pH resistance enhances the selection of bacterial compositions that will survive at the highest yield possible through the varying pH environments of the distinct regions of the GI tract. Understanding how the bacterial compositions react to the pH of the GI tract also assists in formulation, so that the number of bacteria in a dosage form can be increased if beneficial and/or so that the composition may be administered in an enteric-coated capsule or tablet or with a buffering or protective composition. As the pH of the stomach can drop to a pH of 1 to 2 after a high-protein meal for a short time before physiological mechanisms adjust it to a pH of 3 to 4 and often resides at a resting pH of 4 to 5, and as the pH of the small intestine can range from a pH of 6 to 7.4, bacterial compositions can be prepared that survive these varying pH ranges (specifically wherein at least 1%, 5%, 10%, 15%, 20%, 25%, 30%, 40%, 50%, 60%, 70%, 80%, 90%, or as much as 100% of the bacteria can survive gut transit times through various pH ranges). This may be tested by exposing the bacterial composition to varying pH ranges for the expected gut transit times through those pH ranges. Therefore, as a nonlimiting example only, 18-hour cultures of bacterial compositions may be grown in standard media, such as gut microbiota medium ("GMM", see Goodman et al., Extensive personal human gut microbiota culture collections characterized and manipulated in gnotobiotic mice, PNAS 108(15):6252-6257 (2011)) or another animal-products-free medium, with the addition of pH adjusting agents for a pH of 1 to 2 for 30 minutes, a pH of 3 to 4 for 1 hour, a pH of 4 to 5 for 1 to 2 hours, and a pH of 6 to 7.4 for 2.5 to 3 hours. An alternative method for testing stability to acid is described in U.S. Pat. No. 4,839,281. Survival of bacteria may be determined by culturing the bacteria and counting colonies on appropriate selective or non-selective media.

Bile Acid Sensitivity Testing. Additionally, in some embodiments, testing for bile-acid resistance enhances the selection of bacterial compositions that will survive exposures to bile acid during transit through the GI tract. Bile acids are secreted into the small intestine and can, like pH, affect the survival of bacterial compositions. This may be tested by exposing the bacterial compositions to bile acids for the expected gut exposure time to bile acids. For example, bile acid solutions may be prepared at desired concentrations using 0.05 mM Tris at pH 9 as the solvent. After the bile acid is dissolved, the pH of the solution may be adjusted to 7.2 with 10% HCl. Bacterial compositions may be cultured in 2.2 ml of a bile acid composition mimicking the concentration and type of bile acids in the patient, 1.0 ml of 10% sterile-filtered feces media and 0.1 ml of an 18-hour culture of the given strain of bacteria. Incubations may be conducted for from 2.5 to 3 hours or longer. An alternative method for testing stability to bile acid is described in U.S. Pat. No. 4,839,281. Survival of bacteria may be determined by culturing the bacteria and counting colonies on appropriate selective or non-selective media.

Antibiotic Sensitivity Testing. As a further optional sensitivity test, bacterial compositions may be tested for sensitivity to antibiotics. In one embodiment, bacterial compositions may be chosen so that the bacterial constituents are sensitive to antibiotics such that if necessary they can be eliminated or substantially reduced from the patient's gastrointestinal tract by at least one antibiotic targeting the bacterial composition.

Adherence to Gastrointestinal Cells. The bacterial compositions may optionally be tested for the ability to adhere to gastrointestinal cells. A method for testing adherence to gastrointestinal cells is described in U.S. Pat. No. 4,839,281.

The specification is most thoroughly understood in light of the teachings of the references cited within the specification. The embodiments within the specification provide an illustration of embodiments and should not be construed to limit the scope. The skilled artisan readily recognizes that many other embodiments are encompassed. All publications and patents cited in this disclosure are incorporated by reference in their entirety. To the extent the material incorporated by reference contradicts or is inconsistent with this specification, the specification will supersede any such material. The citation of any references herein is not an admission that such references are prior art.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. Examples of the techniques and protocols described herein with regard to therapeutic compositions can be found in, e.g., Remington's Pharmaceutical Sciences, 16th edition, Osol, A. (ed), 1980.

Example 1. Construction of Binary Pairs in a High-Throughput 96-Well Format

To allow high-throughput screening of binary pairs, vials of −80° C. glycerol stock banks were thawed and diluted to 1e8 CFU/mL. Each strain was then diluted 10× (to a final concentration of 1e7 CFU/mL of each strain) into 200 uL of PBS+15% glycerol in the wells of a 96-well plate. Plates were then frozen at −80° C. When needed, plates were removed from −80° C. and thawed at room temperature under anaerobic conditions when testing in a CivSim with *Clostridium difficile*.

Example 2. Construction of Ternary Combinations in a High-Throughput 96-Well Format To allow high-throughput screening of ternary combinations, vials of −80° C. glycerol stock banks were thawed and diluted to 1e8 CFU/mL. Each strain was then diluted 10× (to a final concentration of 1e7 CFU/mL of each strain) into 200 uL of PBS+15% glycerol in the wells of a 96-well plate. Plates were then frozen at −80° C. When needed for the assay, plates were removed from −80° C. and thawed at room temperature under anaerobic conditions when testing in a CivSim with *Clostridium difficile*.

Example 3. Construction of a CivSim Assay to Screen for Ecobiotic™ Compositions Inhibitory to the Growth of *Clostridium difficile*

An overnight culture of *Clostridium difficile* was grown under anaerobic conditions in SweetB-FosIn or other suitable media for the growth of *C. difficile*. SweetB-FosIn is a complex media composed of brain heart infusion, yeast extract, cysteine, cellobiose, maltose, soluble starch, and fructooligosaccharides/inulin, and hemin, and is buffered with MOPs. After 24 hr of growth the culture was diluted 100,000 fold into a complex media such as SweetB-FosIn which is suitable for the growth of a wide variety of anaerobic bacterial species. The diluted *C. difficile* mixture was then aliquoted to wells of a 96-well plate (180 uL to each well). 20 uL of a unique binary pair of potential inhibitory species was then added to each well at a final concentration of 1e6 CFU/mL of each species. Alternatively the assay can be tested with binary pairs at different initial concentrations (1e9 CFU/mL, 1e8 CFU/mL, 1e7 CFU/mL, 1e5 CFU/mL, 1e4 CFU/mL, 1e3 CFU/mL, 1e2 CFU/mL). Control wells only inoculated with *C. difficile* were included for a comparison to the growth of *C. difficile* without inhibition. Additional wells were used for controls that either inhibit or do not inhibit the growth of *C. difficile*. One example of a positive control that inhibits growth was a combination of *Blautia producta, Clostridium bifermentans* and *Escherichia coli*. One example of a control that shows reduced inhibition of *C. difficile* growth as a combination of *Bacteroides* thetaiotaomicron, *Bacteroides ovatus* and *Bacteroides vulgatus*. Plates were wrapped with parafilm and incubated for 24 hr at 37° C. under anaerobic conditions. After 24 hr the wells containing *C. difficile* alone were serially diluted and plated to determine titer. The 96-well plate was then frozen at −80 C before quantifying *C. difficile* by qPCR assay.

Example 4. Construction of a CivSim Assay to Screen for Bacterial Compositions that Produce Diffusible Products Inhibitory to the Growth of *Clostridium difficile* Using a Filter Insert The CivSim assay described above was modified by using a 0.22 uM filter insert (Millipore™ MultiScreen™ 96-Well Assay Plates—Item MAGVS2210) in 96-well format to physically separate *C. difficile* from the bacterial compositions. The *C. difficile* was aliquoted into the 96-well plate while the bacterial compositions were aliquoted into media on the filter overlay. The nutrient media as in contact on both sides of the 0.22 uM filter, allowing exchange of nutrients, small molecules and many macromolecules (e.g., bacteriocins, cell-surface proteins, or polysaccharides) by diffusion. In this embodiment, after 24 hr incubation, the filter insert containing the bacterial compositions was removed. The plate containing *C. difficile* was then transferred to a 96-well plate reader suitable for measuring optical density (OD) at 600 nm. The growth of *C. difficile* in the presence of different bacterial compositions was compared based on the OD measurement.

Example 5. Construction of a CivSim Assay to Screen for Bacterial Compositions Inhibitory to the Growth of *Clostridium difficile* Using *Clostridium difficile* Selective Media for Quantification The CivSim assay described above can be modified to determine final *C. difficile* titer by serially diluting and plating to *C. difficile* selective media (Bloedt et al 2009) such as CCFA (cycloserine cefoxitin fructose agar, Anaerobe Systems), CDSA (*Clostridium difficile* selective agar, which is cycloserine cefoxitin mannitol agar, Becton Dickinson).

Example 6. Quantification of *C. difficile* Using Quantitative PCR (qPCR) Standard Curve Preparation The standard curve was generated from a well on each assay plate containing only pathogenic *C. difficile* grown in SweetB+FosIn media as provided herein and quantified by selective spot plating. Serial dilutions of the culture were performed in sterile phosphate-buffered saline. Genomic DNA was extracted from the standard curve samples along with the other wells.

Genomic DNA Extraction

Genomic DNA was extracted from 5 µl of each sample using a dilution, freeze/thaw, and heat lysis protocol. 5 µL of thawed samples were added to 45 µL of UltraPure water (Life Technologies, Carlsbad, Calif.) and mixed by pipetting. The plates with diluted samples were frozen at −20° C. until use for qPCR which includes a heated lysis step prior to amplification. Alternatively the genomic DNA could be isolated using the Mo Bio Powersoil®-htp 96 Well Soil DNA Isolation Kit (Mo Bio Laboratories, Carlsbad, Calif.), Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions.

qPCR Composition and Conditions

The qPCR reaction mixture contained 1× SsoAdvanced Universal Probes Supermix, 900 nM of Wr-tcdB-F primer (AGCAGTTGAATATAGTGGTTTAGTTAGAGTTG (SEQ ID NO: 1916), IDT, Coralville, Iowa), 900 nM of Wr-tcdB-R primer (CATGCTTTTTAGTTTCTGGATTGAA (SEQ ID NO: 1917), IDT, Coralville, Iowa), 250 nM of Wr-tcdB-P probe (6FAM-CATCCAGTCTCAAT-TGTATATGTTTCTCCA-MGB (SEQ ID NO: 1918), Life Technologies, Grand Island, N.Y.), and Molecular Biology Grade Water (Mo Bio Laboratories, Carlsbad, Calif.) to 18 µl (Primers adapted from: Wroblewski, D. et al., Rapid Molecular Characterization of *Clostridium difficile* and Assessment of Populations of *C. difficile* in Stool Specimens, Journal of Clinical Microbiology 47:2142-2148 (2009)). This reaction mixture was aliquoted to wells of a Hard-shell Low-Profile Thin Wall 96-well Skirted PCR Plate (BioRad, Hercules, Calif.). To this reaction mixture, 2 µl of diluted, frozen, and thawed samples were added and the plate sealed with a Microseal 'B' Adhesive Seal (BioRad, Hercules, Calif.). The qPCR was performed on a BioRad C1000™ Thermal Cycler equipped with a CFX96™ Real-Time System (BioRad, Hercules, Calif.). The thermocycling conditions were 95° C. for 15 minutes followed by 45 cycles of 95° C. for 5 seconds, 60° C. for 30 seconds, and fluorescent readings of the FAM channel. Alternatively, the qPCR could be performed with other standard methods known to those skilled in the art.

Data Analysis

The Cq value for each well on the FAM channel was determined by the CFX Manager™ 3.0 software. The $\log_{10}$ (cfu/mL) of *C. difficile* each experimental sample was calculated by inputting a given sample's Cq value into a linear regression model generated from the standard curve comparing the Cq values of the standard curve wells to the known $\log_{10}$ (cfu/mL) of those samples. The log inhibition was calculated for each sample by subtracting the $\log_{10}$ (cfu/mL) of *C. difficile* in the sample from the $\log_{10}$ (cfu/mL) of *C. difficile* in the sample on each assay plate used for the generation of the standard curve that has no additional bacteria added. The mean log inhibition was calculated for all replicates for each composition.

A histogram of the range and standard deviation of each composition was plotted. Ranges or standard deviations of the log inhibitions that were distinct from the overall distribution were examined as possible outliers. If the removal of a single log inhibition datum from one of the binary pairs that were identified in the histograms would bring the range or standard deviation in line with those from the majority of the samples, that datum was removed as an outlier, and the mean log inhibition was recalculated.

The pooled variance of all samples evaluated in the assay was estimated as the average of the sample variances weighted by the sample's degrees of freedom. The pooled standard error was then calculated as the square root of the pooled variance divided by the square root of the number of samples. Confidence intervals for the null hypothesis were determined by multiplying the pooled standard error to the z score corresponding to a given percentage threshold. Mean log inhibitions outside the confidence interval were considered to be inhibitory if positive or stimulatory if negative with the percent confidence corresponding to the interval used. Samples with mean log inhibition greater than the 99% confidence interval (C.I) of the null hypothesis are reported as ++++, those with a 95%<C.I.<99% as +++, those with a 90%<C.I.<95% as ++, those with a 80%<C.I.<90% as + while samples with mean log inhibition less than the 99% confidence interval (C.I) of the null hypothesis are reported as ----, those with a 95%<C.I.<99% as ---, those with a 90%<C.I.<95% as --, those with a 80%<C.I.<90% as -.

Many binary pairs inhibit *C. difficile* Table 3. 622 of 989 combinations show inhibition with a confidence interval>80%; 545 of 989 with a C.I.>90%; 507 of 989 with a C.I.>95%; 430 of 989 with a C.I. of >99%. Non-limiting but exemplary binary pairs include those with mean log reduction greater than 0.366, e.g. *Allistipes shahii* paired with *Blautia producta*, *Clostridium hathaweyi*, or *Colinsella aerofaciens*, or *Clostidium mayombei* paired with *C. innocuum*, *C. tertium*, *Colinsella aerofaciens*, or any of the other 424 combinations shown in Table 5. Equally important, the CivSim assay describes binary pairs that do not effectively inhibit *C. difficile*. 188 of 989 combinations promote growth with >80% confidence; 52 of 989 show a lack of inhibition with >90% confidence; 22 of 989 show a lack of inhibition with >95% confidence; 3 of 989, including *B. producta* combined with *Coprococcus catus*, *Alistipes shahii* combined with *Dorea formicigenerans*, and *Eubacterium rectale* combined with *Roseburia intestinalis*, show a lack of inhibition with >99% confidence. 249 of 989 combinations are neutral in the assay, meaning they neither promote nor inhibit *C. difficile* growth to the limit of measurement.

Ternary combinations with mean log inhibition greater than 0.312 are reported as ++++ (≥99% confidence interval (C.I.) of the null hypothesis), those with mean log inhibition between 0.221 and 0.312 as +++ (95%<C.I.<99%), those with mean log inhibition between 0.171 and 0.221 as ++ (90%<C.I.<95%), those with mean log inhibition between 0.113 and 0.171 as + (80%<C.I.<90%), those with mean log inhibition between −0.113 and −0.171 as − (80%<C.I.<90%), those with mean log inhibition between −0.171 and −0.221 as −− (90%<C.I.<95%), those with mean log inhibition between −0.221 and −0.312 as −−− (95%<C.I.<99%), and those with mean log inhibition less than −0.312 as −−−− (99%<C.I.).

The CivSim shows that many ternary combinations inhibit *C. difficile*. 39 of 56 combinations show inhibition with a confidence interval>80%; 36 of 56 with a C.I.>90%; 36 of 56 with a C.I.>95%; 29 of 56 with a C.I. of >99%. Non-limiting but exemplary ternary combinations include those with mean log reduction greater than 0.171, e.g. any combination shown in Table 4 with a score of ++++, such as *Colinsella aerofaciens, Coprococcus comes*, and *Blautia producta*. Equally important, the CivSim assay describes ternary combinations that do not effectively inhibit *C. difficile*. 5 of 56 combinations promote growth with >80% confidence; 2 of 56 promote growth with >90% confidence; 1 of 56, *Coprococcus comes, Clostridium symbiosum* and *Eubacterium rectale*, promote growth with >95% confidence. 12 of 56 combinations are neutral in the assay, meaning they neither promote nor inhibit *C. difficile* growth to the limit of measurement.

Example P1. Full 16S Sequencing to Determine Operational Taxonomic Unit (OTU) Genomic DNA Extraction Genomic DNA is extracted from pure microbial cultures using a hot alkaline lysis method. 2 µl of microbial culture is added to 18 µl of Lysis Buffer (25 mM NaOH, 0.2 mM EDTA) and the mixture is incubated at 95° C. for 30 minutes. Subsequently, the samples are cooled to 4° C. and neutralized by the addition of 20 µl of Neutralization Buffer (40 mM Tris-HCl) and then diluted 10-fold in Elution Buffer (10 mM Tris-HCl). Alternatively, genomic DNA is extracted from pure microbial cultures using commercially available kits such as the Mo Bio Ultraclean® Microbial DNA Isolation Kit (Mo Bio Laboratories, Carlsbad, Calif.) or by standard methods known to those skilled in the art.

PCR

To amplify bacterial 16S rDNA, 2 µl of extracted gDNA is added to a 20 µl final volume PCR reaction. The PCR reaction also contains 1× HotMasterMix (5PRIME, Gaithersburg, Md.), 250 nM of 27f primer (AGRGTTT-GATCMTGGCTCAG (SEQ ID NO: 1919), IDT, Coralville, Iowa), and 250 nM of 1492r primer (TACGGYTACCTTGT-TAYGACTT (SEQ ID NO: 1920), IDT, Coralville, Iowa), with Molecular Biology Grade Water (Mo Bio Laboratories, Carlsbad, Calif.) for the balance of the volume. Alternatively, other universal bacterial primers or thermostable polymerases known to those skilled in the art are used.

The PCR performed on commercially available thermocyclers such as a BioRad MyCycler™ Thermal Cycler (BioRad, Hercules, Calif.). The reactions are run at 94° C. for 2 minutes followed by 30 cycles of 94° C. for 30 seconds, 51° C. for 30 seconds, and 68° C. for 1 minute 30 seconds, followed by a 7 minute extension at 72° C. and an indefinite hold at 4° C. Following PCR, gel electrophoresis of a portion of the reaction products is used to confirm successful amplification of a ~1.5 kb product.

PCR Cleanup

To remove nucleotides and oligonucleotides from the PCR products, 1 µl of HT ExoSap-IT (Affymetrix, Santa Clara, Calif.) is added to 2.5 µl of PCR product followed by a 15 minute incubation at 37° C. and then a 15 minute inactivation at 80° C.

Sanger Sequencing

For each sample, two sequencing reactions are performed, one using each primer: 27f and 1492r. 40 ng of ExoSap-IT-cleaned PCR products are mixed with 25 pmol of sequencing primer and Molecular Biology Grade Water (Mo Bio Laboratories, Carlsbad, Calif.) to 15 µl total volume. This reaction is submitted to a commercial sequencing organization such as Genewiz (South Plainfield, N.J.) for Sanger sequencing.

Example P2. V4 16S Sequencing to Determine Operational Taxonomic Unit (OTU) Genomic DNA Extraction Genomic DNA is extracted from pure microbial cultures using a hot alkaline lysis method. 2 µl of microbial culture is added to 18 µl of Lysis Buffer (25 mM NaOH, 0.2 mM EDTA) and the mixture is incubated at 95° C. for 30 minutes. Subsequently, the samples are cooled to 4° C. and neutralized by the addition of 18 µl of Neutralization Buffer (40 mM Tris-HCl) and then diluted 10-fold in Elution Buffer (10 mM Tris-HCl). Alternatively, genomic DNA is extracted from pure microbial cultures using commercially available kits such as the Mo Bio Ultraclean® Microbial DNA Isolation Kit (Mo Bio Laboratories, Carlsbad, Calif.) or by standard methods known to those in skilled in the art.

PCR

To amplify the V4 region of bacterial 16S rDNA, 2 µl of extracted gDNA is added to a 20 µl final volume PCR reaction. The PCR reaction also contains 1× HotMasterMix (5PRIME, Gaithersburg, Md.), 200 nM of V4_515f_adapt (AATGATACGGCGACCACCGAGATCTACAC-TATGGTAATTGTGTGCCAGCMGCCGCG GTAA (SEQ ID NO: 1921), IDT, Coralville, Iowa), and 200 nM of barcoded 806rbc (CAAGCAGAAGACGGCATACGAGAT (SEQ ID NO: 1922)_12bpGolayBarcode_AGTCAGTCAGCCGGACTACHVGGGTWTCTAAT (SEQ ID NO: 1923), IDT, Coralville, Iowa), with Molecular Biology Grade Water (Mo Bio Laboratories, Carlsbad, Calif.) for the balance of the volume. These primers incorporate adapters for Illumina sequencing by synthesis. Optionally, identical replicate, triplicate, or quadruplicate reactions may be performed. Alternatively other universal bacterial primers or thermostable polymerases known to those skilled in the art are used.

The PCR performed on commercially available thermocyclers such as a BioRad MyCycler™ Thermal Cycler (BioRad, Hercules, Calif.). The reactions are run at 94° C. for 3 minutes followed by 25 cycles of 94° C. for 45 seconds, 50° C. for 1 minute, and 72° C. for 1 minute 30 seconds, followed by a 10 minute extension at 72° C. and a indefinite hold at 4° C. Following PCR, gel electrophoresis of a portion of the reaction products is used to confirm successful amplification of a ~0.4 kb product.

PCR Cleanup

To remove nucleotides and oligonucleotides from the PCR products, the entire remaining volume of the PCR, or of the multiple PCRs, is cleaned up using the Mo Bio Ultraclean®-htp 96 Well PCR Clean-up Kit (Mo Bio Laboratories, Carlsbad, Calif.) according to the manufacturer's instructions or other commercially available kits such as the QIAquick 96 PCR Purification Kit (QIAGEN, Valencia, Calif.).

DNA Quantification & Pooling

The cleaned PCR products are quantified using the Quant-iT™ PicoGreen® dsDNA Assay Kit (Life Technologies, Grand Island, N.Y.) according to the manufacturer's instructions. Following quantification, the barcoded cleaned PCR products are combined such that each distinct PCR product is at an equimolar ratio to create a prepared Illumina library.

Illumina Sequencing

The prepared library is sequenced on Illumina HiSeq or MiSeq sequencers (Illumina, San Diego, Calif.) with cluster generation, template hybridization, iso-thermal amplification, linearization, blocking and denaturization and hybridization of the sequencing primers performed according to the manufacturer's instructions. 16SV4SeqFw (TATGGTAATTGTGTGCCAGCMGCCGCGGTAA (SEQ ID NO: 1924)), 16SV4SeqRev (AGTCAGTCAGCCGGACTACHVGGGTWTCTAAT (SEQ ID NO: 1923)), and 16SV4Index (ATT-AGAWACCCBDGTAGTCCGGCTGACTGACT (SEQ ID NO: 1925)) (IDT, Coralville, Iowa) are used for sequencing. This sequencing can optionally be performed by a contract research organization such as Metanome (Houston, Tex.), Ambry Genetics (Aliso Viejo, Calif.), Edge Bio (Gaithersburg, Md.), or Covance (Princeton, N.J.).

Taxonomic Assignment to Sequence Read Data

Nucleic acid sequences are analyzed and taxonomic and phylogenetic assignments of specific OTUs are made using sequence similarity and phylogenetic methods that are well known to those skilled in the art, including but not limited to maximum likelihood phylogenetic reconstruction (see e.g. Liu K, Linder C R, and Warnow T. 2011. RAxML and FastTree: Comparing Two Methods for Large-Scale Maximum Likelihood Phylogeny Estimation. *PLoS ONE* 6: e27731. McGuire G, Denham M C, and Balding D J. 2001. Models of sequence evolution for DNA sequences containing gaps. *Mol. Biol. Evol* 18: 481-490. Wróbel B. 2008. Statistical measures of uncertainty for branches in phylogenetic trees inferred from molecular sequences by using model-based methods. *J. Appl. Genet.* 49: 49-67.) From these taxonomic assignments OTUs in the dataset are defined. The certainty of the OTU call is defined based on the OTU's sequence similarity to a reference nucleic acid sequence and the proximity of the OTU sequence relative to one or more reference sequences in the phylogeny. The specificity of an OTU's taxonomic and phlylogenetic assignment determines whether the match is assigned at the level of Family, Genus, Species, or Strain, and the confidence of this assignment is determined based on the position of bootstrap supported branches in the reference phylogenetic tree relative to the placement of the OTU sequence being interrogated.

Example P3. Construction of an In Vitro Assay to Screen for Combinations of Microbes Inhibitory to the Growth of Pathogenic *E. coli*

The in vitro assay is used to screen for combinations of bacteria inhibitory to the growth of *E. coli* by modifying the media used for growth of the pathogen inoculum. One of several choices of media is used for growth of the pathogen such as Reinforced Clostridial Media (RCM), Brain Heart Infusion Broth (BHI) or Luria Bertani Broth (LB) (also known as Lysogeny Broth). *E. coli* is quantified by using alternative selective media specific for *E. coli* or using qPCR probes specific for the pathogen. For example, aerobic growth on MacConkey lactose medium selects for enteric Gram negatives, including *E. coli*. qPCR is conducted using probes specific for the shiga toxin of pathogenic *E. coli*.

Example P4. Construction of an In Vitro Assay to Screen for Combinations of Microbes Inhibitory to the Growth of Vancomycin-Resistant *Enterococcus* (VRE)

The in vitro assay is used to screen for combinations of bacteria inhibitory to the growth of Vancomycin-Resistant *Enterococcus* spp. (VRE) by modifying the media used for growth of the pathogen inoculum. Several choices of media are used for growth of the pathogen such as Reinforced Clostridial Media (RCM), Brain Heart Infusion Broth (BHI) or Luria Bertani Broth (LB). VRE is quantified by using alternative selective media specific for VRE or using qPCR probes specific for the pathogen. For example, m-*Enterococcus* agar containing sodium azide is selective for *Enterococcus* spp. and a small number of other species. Probes specific to the van genes conferring vancomycin resistance are used in the qPCR.

Example P5. Testing of Bacterial Composition Against *Salmonella*

The in vitro assay is used to screen for combinations of bacteria inhibitory to the growth of *Salmonella* spp. by modifying the media used for growth of the pathogen inoculum. Several choices of media are used for growth of the pathogen such as Reinforced Clostridial Media (RCM), Brain Heart Infusion Broth (BHI) or Luria Bertani Broth (LB). *Salmonella* spp. are quantified by using alternative selective media specific for *Salmonella* spp. or using qPCR probes specific for the pathogen. For example, MacConkey agar is used to select for *Salmonella* spp. and the invA gene is targeted with qPCR probes; this gene encodes an invasion protein carried by many pathogenic *Salmonella* spp. and is used in invading eukaryotic cells.

Example P6. Method of Preparing the Bacterial Composition for Administration to a Subject Two strains for the bacterial composition are independently cultured and mixed together before administration. Both strains are independently be grown at 37° C., pH 7, in a GMM or other animal-products-free medium, pre-reduced with 1 g/L cysteine☐HCl. After each strain reaches a sufficient biomass, it is preserved for banking by adding 15% glycerol and then frozen at −80° C. in 1 ml cryotubes.

Each strain is then be cultivated to a concentration of $10^{10}$ CFU/mL, then concentrated 20-fold by tangential flow microfiltration; the spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder ($10^8$ to $10^{11}$ bacteria), 160 mg microcrystalline cellulose, 77.5 mg gelatin, and 2.5 mg magnesium stearate.

Example P7. Method of Treating a Subject with a Bacterial Composition

A patient has suffered from recurrent bouts of *C. difficile*. In the most recent acute phase of illness, the patient is treated with an antibiotic sufficient to ameliorate the symptoms of the illness. In order to prevent another relapse of *C. difficile*, the patient is administered one of the present bacterial compositions. Specifically, the patient is administered *Bacillus circulans* and *Roseburia inulinivorans* at a dose of $10^8$ bacteria total in a lyophilized form, specifically in a 250 mg gelatin capsule containing 10 mg of lyophilized bacteria, 160 mg microcrystalline cellulose, 77.5 mg gelatin, and 2.5 mg magnesium stearate. The patient takes the capsule by mouth and resumes a normal diet after 4, 8, 12, or 24 hours. In another embodiment, the patient may take the capsule by mouth before, during, or immediately after a meal.

Feces is collected before and at 1 day, 3 days, 1 week, and 1 month after administration. The presence of *C. difficile* is found in the feces before administration of the bacterial composition, but feces collections after administration show reducing (such as at least 50% less, 60%, 70%, 80%, 90%, or 95%) to no detectable levels of *C. difficile*, as measured by qPCR, as described above. ELISA for toxin protein or traditional microbiological identification techniques may also be used.

As another measure of patient success, a positive response may be defined as absence of diarrhea, which itself is defined as 3 or more loose or watery stools per day for at least 2 consecutive days or 8 or more loose or watery stools in 48 hours, or persisting diarrhea (due to other causes) with repeating (three times) negative stool tests for toxins of *C. difficile*.

Treatment failure is defined as persisting diarrhea with a positive *C. difficile* toxin stool test or no reduction in levels of *C. difficile*, as measured by qPCR sequencing. ELISA or traditional microbiological identification techniques may also be used.

Example P8. Method of Treating a Subject with a Bacterial Composition

A patient has suffered from recurrent bouts of *C. difficile*. In the most recent acute phase of illness, the patient is treated with an antibiotic sufficient to ameliorate the symptoms of the illness. In order to prevent another relapse of *C. difficile*, the patient is administered one of the present bacterial compositions. Specifically, the patient is administered a bacterial composition containing two bacterial types from Table 1 or SEQ ID NOs. 1-1,864, or a combination from Table 2, at a dose of $10^8$ bacteria total in a lyophilized form formulated in an enteric coated capsule. Example of the patient or samples derived from the patient is expected to demonstrate at least one measure of success as described herein (reducing levels of *C. difficile* as measured by qPCR, ELISA, or traditional microbiological identification; absence of diarrhea; persisting diarrhea with repeating (three times) negative stool tests for toxins of *C. difficile*.

Other embodiments will be apparent to those skilled in the art from consideration of the specification and practice of the embodiments. Consider the specification and examples as exemplary only, with a true scope and spirit being indicated by the following claims.

Lengthy table referenced here

US11464812-20221011-T00001

Please refer to the end of the specification for access instructions.

Lengthy table referenced here

US11464812-20221011-T00002

Please refer to the end of the specification for access instructions.

Lengthy table referenced here

US11464812-20221011-T00003

Please refer to the end of the specification for access instructions.

Lengthy table referenced here

US11464812-20221011-T00004

Please refer to the end of the specification for access instructions.

Lengthy table referenced here

US11464812-20221011-T00005

Please refer to the end of the specification for access instructions.

Lengthy table referenced here

US11464812-20221011-T00006

Please refer to the end of the specification for access instructions.

Lengthy table referenced here

US11464812-20221011-T00007

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11464812B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11464812B2). An electronic copy of the "Sequence Listing" will also be available from the USPTO upon request and payment of the fee set forth in 37 CFR 1.19(b)(3).

What is claimed is:

1. A composition comprising a first species of isolated bacterium and a second species of isolated bacterium and a capsule, which encapsulates the first species, the second species, or both the first and second species of isolated bacterium, wherein the first species is Lachnospiraceae_bacterium_ 5_1_57FAA and the second species is *Clostridium disporicum*, wherein the Lachnospiraceae_bacterium_ 5_1_57FAA FAA comprises a 16S rDNA sequence that is at least 97% identical to the 16S rDNA sequence set forth in SEQ ID NO: 979, and wherein the first species and the second species are capable of inhibiting *Clostridium difficile* (*C. difficile*) growth as measured by a CivSim assay.

2. The composition of claim 1, which further comprises an enteric coating.

3. The composition of claim 1, wherein the first species and the second species are capable of inhibiting *C. difficile* growth in the CivSim assay with a confidence interval of >99% (++++).

4. The composition of claim 1, wherein the first species, the second species, or both are in the form of spores.

5. The composition of claim 1, which is formulated for populating the gastrointestinal tract of the subject.

6. The composition of claim 1, wherein the first species, the second species, or both are lyophilized.

7. A kit comprising in one or more containers the composition of claim 1.

8. A pharmaceutical formulation comprising the composition of claim 1.

9. The pharmaceutical formulation of claim 8, further comprising an additional agent.

10. The pharmaceutical formulation of claim 9, wherein the additional agent is selected from an anti-bacterial agent, anti-fungal agent, anti-viral agent, anti-parasitic agent, or combinations thereof.

11. The composition of claim 1, wherein the Lachnospiraceae_bacterium_ 5_1_57FAA comprises a 16S rDNA sequence that is at least 98% identical to SEQ ID NO: 979.

12. The composition of claim 1, wherein the Lachnospiraceae_bacterium_ 5_1_57FAA comprises a 16S rDNA sequence that is at least 99% identical to SEQ ID NO: 979.

13. The composition of claim 1, wherein the *Clostridium disporicum* comprises a 16S rDNA sequence that is at least 97% identical to SEQ ID NO: 518.

14. The composition of claim 1, wherein the *Clostridium disporicum* comprises a 16S rDNA sequence that is at least 98% identical to SEQ ID NO: 518.

15. The composition of claim 1, wherein the *Clostridium disporicum* comprises a 16S rDNA sequence that is at least 99% identical to SEQ ID NO: 518.

16. The pharmaceutical formulation of claim 8, which further comprises a pharmaceutically acceptable excipient.

17. The pharmaceutical formulation of claim 8, which is formulated for oral administration.

18. The composition of claim 1, which further comprises glycerol.

19. The composition of claim 1, wherein the Lachnospiraceae_bacterium_ 5_1_57FAA comprises the 16S rDNA sequence set forth in SEQ ID NO: 979.

20. The composition of claim 1, wherein the *Clostridium disporicum* comprises the 16S rDNA sequence set forth in SEQ ID NO: 518.

* * * * *